United States Patent
Crawford et al.

(10) Patent No.: US 9,115,152 B2
(45) Date of Patent: *Aug. 25, 2015

(54) ALKYLATED PIPERAZINE COMPOUNDS

(71) Applicant: Genentech, Inc., South San Francisco, CA (US)

(72) Inventors: James John Crawford, San Francisco, CA (US); Wendy B. Young, San Mateo, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/566,920

(22) Filed: Dec. 11, 2014

(65) Prior Publication Data

US 2015/0094302 A1     Apr. 2, 2015

Related U.S. Application Data

(63) Continuation of application No. 14/246,471, filed on Apr. 7, 2014, which is a continuation of application No. 13/667,114, filed on Nov. 2, 2012, now Pat. No. 8,729,072.

(60) Provisional application No. 61/555,395, filed on Nov. 3, 2011.

(51) Int. Cl.
| | |
|---|---|
| *C07D 513/04* | (2006.01) |
| *A61K 31/496* | (2006.01) |
| *A61K 45/06* | (2006.01) |
| *A61K 31/5386* | (2006.01) |
| *C07D 487/04* | (2006.01) |
| *A61K 31/4985* | (2006.01) |
| *C07D 498/08* | (2006.01) |
| *C07D 471/14* | (2006.01) |
| *A61K 31/5025* | (2006.01) |
| *C07D 471/04* | (2006.01) |
| *C07D 495/04* | (2006.01) |
| *C07D 519/00* | (2006.01) |

(52) U.S. Cl.
CPC ............ *C07D 513/04* (2013.01); *A61K 31/496* (2013.01); *A61K 31/4985* (2013.01); *A61K 31/5025* (2013.01); *A61K 31/5386* (2013.01); *A61K 45/06* (2013.01); *C07D 471/04* (2013.01); *C07D 471/14* (2013.01); *C07D 487/04* (2013.01); *C07D 495/04* (2013.01); *C07D 498/08* (2013.01); *C07D 519/00* (2013.01)

(58) Field of Classification Search
USPC .......... 514/230.5, 253.03, 248, 250; 544/361, 544/234, 344, 105
See application file for complete search history.

(56) References Cited

U.S. PATENT DOCUMENTS

| | | | |
|---|---|---|---|
| 7,683,064 B2 | 3/2010 | Dewdney et al. | |
| 7,838,523 B2 | 11/2010 | Blomgren et al. | |
| 7,884,108 B2 | 2/2011 | Bloomgren et al. | |
| 7,902,194 B2 | 3/2011 | Dewdney et al. | |
| 7,906,509 B2 | 3/2011 | Kennedy-Smith et al. | |
| 7,947,835 B2 | 5/2011 | Brittelli et al. | |
| 8,058,446 B2 | 11/2011 | Blomgren et al. | |
| 8,124,604 B2 | 2/2012 | Dewdney et al. | |
| 8,618,107 B2 * | 12/2013 | Barbosa et al. | 514/252.01 |
| 8,716,274 B2 * | 5/2014 | Crawford et al. | 514/210.21 |
| 8,729,072 B2 * | 5/2014 | Crawford et al. | 514/230.5 |
| 8,921,353 B2 * | 12/2014 | Crawford et al. | 514/210.21 |
| 2008/0125417 A1 | 5/2008 | Currie et al. | |

(Continued)

FOREIGN PATENT DOCUMENTS

| | | |
|---|---|---|
| CN | 103038233 A | 4/2013 |
| WO | 2009/039397 A2 | 3/2009 |

(Continued)

OTHER PUBLICATIONS

Cancer [online], [retrieved on Jul. 6, 2007] Retrieved from the Internet, URL: http://www.nlm.nih.gov/medlineplus/cancer.html.*

(Continued)

*Primary Examiner* — Kristin Vajda
(74) *Attorney, Agent, or Firm* — Mark D. Kafka

(57) ABSTRACT

Alkylated piperazine compounds of Formula I are provided, including stereoisomers, tautomers, and pharmaceutically acceptable salts thereof, useful for inhibiting Btk kinase, and for treating cancer mediated by Btk kinase. Methods of using compounds of Formula I for in vitro, in situ, and in vivo diagnosis, and treatment of cancer in mammalian cells, or associated pathological conditions, are disclosed.

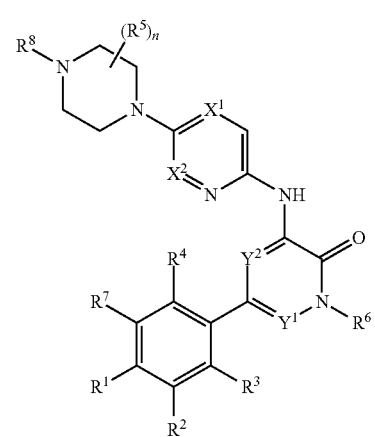

4 Claims, 11 Drawing Sheets

(56) References Cited

U.S. PATENT DOCUMENTS

| | | | |
|---|---|---|---|
| 2009/0186898 A1 | 7/2009 | Dewdney et al. | |
| 2010/0004231 A1 | 1/2010 | Dewdney et al. | |
| 2010/0016301 A1 | 1/2010 | Dewdney et al. | |
| 2011/0118233 A1 | 5/2011 | Blomgren et al. | |
| 2011/0301145 A1 | 12/2011 | Barbosa et al. | |
| 2012/0010191 A1 | 1/2012 | Barbosa et al. | |
| 2012/0040949 A1 | 2/2012 | Berthel et al. | |
| 2012/0295885 A1 | 11/2012 | Billedeau et al. | |
| 2013/0045965 A1 | 2/2013 | Brotherton-Pleiss et al. | |
| 2014/0057896 A1* | 2/2014 | Barbosa et al. | 514/210.21 |
| 2014/0221365 A1* | 8/2014 | Crawford et al. | 514/230.5 |
| 2014/0378432 A1* | 12/2014 | Crawford et al. | 514/210.21 |

FOREIGN PATENT DOCUMENTS

| | | |
|---|---|---|
| WO | 2010/000633 A1 | 1/2010 |
| WO | 2010/122038 A1 | 10/2010 |
| WO | 2011/140488 A1 | 11/2011 |
| WO | 2012/030990 A1 | 3/2012 |
| WO | 2012/031004 | 3/2012 |

OTHER PUBLICATIONS

Lala et al., Role of nitric oxide in tumor progression: Lessons from experimental tumors, Cancer and Metastasis Reviews (1998), 17, 91-106.*

Golub et al., Molecular Classification of Cancer: Class Discovery and Class Prediction by Gene Expression Monitoring, Science (1999), vol. 286, 531-537.*

Di Paolo et al., "Specific Btk inhibition suppresses B-cell- and myeloid cell-mediated arthritis" Nat Chem Biol. 7(1):41-50 (2011).

Liu et al., "Antiarthritis effect of a novel Bruton's tyrosine kinase (BTK) inhibitor in rat collagen-induced arthritis and mechanism-based pharmacokinetic/pharmacodynamic modeling: relationships between inhibition of BTK phosphorylation and efficacy" J Pharmacol Exp Ther. 338(1):154-63 (2011).

First Office Action issued in Chinese Patent Application No. 201280065838.8, dated Apr. 21, 2015, with English Translation (total in 13 pages).

* cited by examiner

ALKYLATED PIPERAZINE COMPOUNDS

CROSS REFERENCE TO RELATED APPLICATIONS

This application is a continuing application of U.S. Ser. No. 14/246,471 filed 7 Apr. 2014, which is a continuing application of U.S. Ser. No. 13/667,114 filed 2 Nov. 2012, now U.S. Pat. No. 8,729,072 issued 20 May 2014, under 37 CFR §1.53(b), also claims the benefit under 35 USC §119(e) of U.S. Provisional Application Ser. No. 61/555,395 filed 3 Nov. 2011, which are incorporated by reference in their entirety.

FIELD OF THE INVENTION

The invention relates generally to compounds for treating disorders mediated by Bruton's Tyrosine Kinase (Btk) including inflammation, immunological, and cancer, and more specifically to compounds which inhibit Btk activity. The invention also relates to methods of using the compounds for in vitro, in situ, and in vivo diagnosis or treatment of mammalian cells, or associated pathological conditions.

BACKGROUND OF THE INVENTION

Protein kinases, the largest family of human enzymes, encompass well over 500 proteins. Bruton's Tyrosine Kinase (Btk) is a member of the Tec family of tyrosine kinases, and is a regulator of early B-cell development as well as mature B-cell activation, signaling, and survival.

B-cell signaling through the B-cell receptor (BCR) can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation. Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice can also be resistant to developing collagen-induced arthritis and can be less susceptible to *Staphylococcus*-induced arthritis. A large body of evidence supports the role of B-cells and the humoral immune system in the pathogenesis of autoimmune and/or inflammatory diseases. Protein-based therapeutics (such as Rituxan) developed to deplete B-cells, represent an approach to the treatment of a number of autoimmune and/or inflammatory diseases. Because of Btk's role in B-cell activation, inhibitors of Btk can be useful as inhibitors of B-cell mediated pathogenic activity (such as autoantibody production). Btk is also expressed in osteoclasts, mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases such as: SLE, rheumatoid arthritis, multiple vasculitides, idiopathic thrombocytopenic purpura (ITP), myasthenia gravis, allergic rhinitis, and asthma (Di Paolo et al (2011) Nature Chem. Biol. 7(1):41-50; Liu et al (2011) Jour. of Pharm. and Exper. Ther. 338(1):154-163). In addition, Btk has been reported to play a role in apoptosis; thus, inhibition of Btk activity can be useful for cancer, as well as the treatment of B-cell lymphoma, leukemia, and other hematological malignancies. Moreover, given the role of Btk in osteoclast function, the inhibition of Btk activity can be useful for the treatment of bone disorders such as osteoporosis. Specific Btk inhibitors have been reported (Liu (2011) Drug Metab. and Disposition 39(10):1840-1849; U.S. Pat. No. 7,884,108, WO 2010/056875; U.S. Pat. No. 7,405,295; U.S. Pat. No. 7,393,848; WO 2006/053121; U.S. Pat. No. 7,947,835; US 2008/0139557; U.S. Pat. No. 7,838,523; US 2008/0125417; US 2011/0118233; PCT/US2011/050034 "PYRIDINONES/PYRAZINONES, METHOD OF MAKING, AND METHOD OF USE THEREOF", filed 31 Aug. 2011; PCT/US2011/050013 "PYRIDAZINONES, METHOD OF MAKING, AND METHOD OF USE THEREOF", filed 31 Aug. 2011; U.S. Ser. No. 13/102,720 "PYRIDONE AND AZA-PYRIDONE COMPOUNDS AND METHODS OF USE", filed 6 May 2011).

SUMMARY OF THE INVENTION

The invention relates generally to Formula I, alkylated piperazine pyridone compounds with Bruton's Tyrosine Kinase (Btk) modulating activity.

Formula I compounds have the structures:

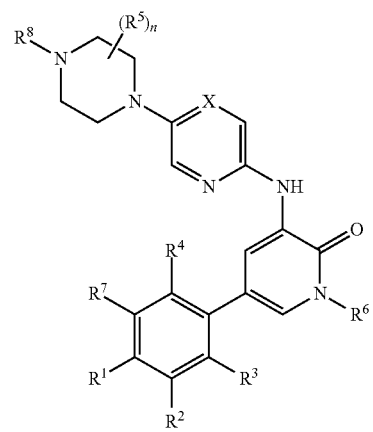

including stereoisomers, tautomers, or pharmaceutically acceptable salts thereof. The various substituents are defined herein below.

One aspect of the invention is a pharmaceutical composition comprised of a Formula I compound and a pharmaceutically acceptable carrier, glidant, diluent, or excipient. The pharmaceutical composition may further comprise a second therapeutic agent.

Another aspect of the invention is a process for making a pharmaceutical composition which comprises combining a Formula I compound with a pharmaceutically acceptable carrier.

The invention includes a method of treating a disease or disorder which method comprises administering a therapeutically effective amount of a Formula I compound to a patient with a disease or disorder selected from immune disorders, cancer, cardiovascular disease, viral infection, inflammation, metabolism/endocrine function disorders and neurological disorders, and mediated by Bruton's tyrosine kinase.

The invention includes a kit for treating a condition mediated by Bruton's tyrosine kinase, comprising: a) a first pharmaceutical composition comprising a Formula I compound; and b) instructions for use.

The invention includes a Formula I compound for use as a medicament, and for use in treating a disease or disorder selected from immune disorders, cancer, cardiovascular disease, viral infection, inflammation, metabolism/endocrine function disorders and neurological disorders, and mediated by Bruton's tyrosine kinase.

The invention includes use of a Formula I compound in the manufacture of a medicament for the treatment of immune disorders, cancer, cardiovascular disease, viral infection, inflammation, metabolism/endocrine function disorders and neurological disorders, and where the medicament mediates Bruton's tyrosine kinase.

The invention includes methods of making a Formula I compound.

BRIEF DESCRIPTION OF THE DRAWINGS

FIG. 1 shows the preparation of (S)-2-(5-Fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)-phenyl)-3,4,6,7,8,9-hexahydropyrido[3,4-b]indolizin-1(2H)-one 101, starting with intermediate 2,6-Dibromo-4-fluorobenzaldehyde 101a.

FIG. 2 shows the preparation of (S)-5-[5-fluoro-2-(hydroxymethyl)-3(1-methyl-5-(5-(2-methyl-4-(oxetan-3-yl)piperazin-1-yl)pyridin-2-ylamino)-6-oxo-1,6-dihydropyridin-3-yl)phenyl]-8-thia-4,5-diazatricyclo[7.4.0.02,7]trideca-1(9),2(7),3-trien-6-one 102, starting with intermediate (S)-[4-fluoro-2-(1-methyl-5-(5-(2-methyl-4-(oxetan-3-yl)-piperazin-1-yl)pyridin-2-ylamino)-6-oxo-1,6-dihydropyridin-3-yl)-6-{6-oxo-8-thia-4,5-diazatricyclo[7.4.0.02,7]trideca-1(9),2(7),3-trien-5-yl}phenyl]methyl acetate 102a.

FIG. 3 shows the preparation of (2S)-10-[5-fluoro-2-(hydroxymethyl)-3-[1-methyl-5-({5-[2-methyl-4-(oxetan-3-yl)piperazin-1-yl]pyridine-2-yl}amino)-6-oxo-1,6-dihydropyridin-3-yl]-phenyl]-4,4-dimethyl-1,10-diazatricyclo[6.4.0.0$^{2,6}$]dodeca-2(6),7-dien-9-one 103, starting with intermediate (E)-Ethyl 3-(2-Chloro-4,4-dimethylcyclopent-1-enyl)acrylate 103a.

FIG. 4a shows the preparation of 2-(3-(5-(5-((2S,5R)-2,5-Dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 104, starting with intermediate (2R,5S)-tert-Butyl2,5-dimethyl-4-(6-nitropyridin-3-yl)piperazine-1-carboxylate 104a.

FIG. 5 shows the preparation of (S)-2-(3-(5-(5-(2-Ethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 105, starting with intermediate (S)-2-(5-(5-(2-Ethyl-4-(oxetan-3-yl)piperazin-1-yl)pyridin-2-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl acetate 105a.

FIG. 6 shows the preparation of (S)-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one 106, starting with intermediate (S)-4-fluoro-2-(1-methyl-5-(5-(2-methyl-4-(oxetan-3-yl)piperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate 106a.

FIG. 7 shows the preparation of (S)-2-(3-(5-(5-(3,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 107, starting with intermediate (S)-tert-Butyl 2-Methyl-4-(6-nitropyridin-3-yl)piperazine-1-carboxylate 107a.

FIG. 8 shows the preparation of (R)-2-(3-(5-(5-(3,4-dimethylpiperazin-1-yl)pyridin-2-ylamino)-1-methyl-6-oxo-1,6-dihydropyridin-3-yl)-5-fluoro-2-(hydroxymethyl)-phenyl)-3,4,6,7,8,9-hexahydropyrazino[1,2-a]indol-1(2H)-one 108, starting with intermediate (R)-tert-Butyl 2-Methyl-4-(6-nitropyridin-3-yl) piperazine-1-carboxylate 108a FIG. 9 shows the preparation of (R)-2-(3-(5-(5-(2,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 109, starting with intermediate (R)-tert-Butyl 3-Methyl-4-(6-nitropyridin-3-yl)piperazine-1-carboxylate 109a.

FIG. 10 shows the preparation of (S)-2-(3-(5-(5-(2,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 110, starting with intermediate (S)-5-Bromo-3-(5-(2,4-dimethylpiperazin-1-yl)pyridin-2-ylamino)-1-methylpyridin-2(1H)-one 110a.

FIG. 11 shows the preparation of 2-(5-Fluoro-3-(5-(5-(3-(fluoromethyl)-4-methylpiperazin-1-yl)pyridin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 111, starting with intermediate 1-tert-Butyl 2-Methyl 4-benzylpiperazine-1,2-dicarboxylate 111a.

FIG. 12 shows the preparation of 2-(5-Fluoro-2-(hydroxymethyl)-3-(1-methyl-5-(5-(9-methyl-7-oxa-3,9-diazabicyclo[3.3.1]nonan-3-yl)pyridin-2-ylamino)-6-oxo-1,6-dihydropyridin-3-yl)phenyl)-3,4,6,7,8,9-hexahydropyrazino[1,2-a]indol-1(2H)-one 112, starting with intermediate N,N-Dibromobenzenesulfonamide 112a.

FIG. 13 shows the preparation of (S)-2-(7,7-Difluoro-1-oxo-3,4,6,7,8,9-hexahydropyrazino[1,2-a]indol-2(1H)-yl)-4-fluoro-6-(1-methyl-5-(5-(2-methyl-4-(oxetan-3-yl)piperazin-1-yl)pyridin-2-ylamino)-6-oxo-1,6-dihydropyridin-3-yl)benzyl Acetate 113q starting with intermediate (3S)-tert-Butyl 3-Methyl-4-(6-nitropyridin-3-yl)piperazine-1-carboxylate 113a.

DETAILED DESCRIPTION OF EXEMPLARY EMBODIMENTS

Figure 1:
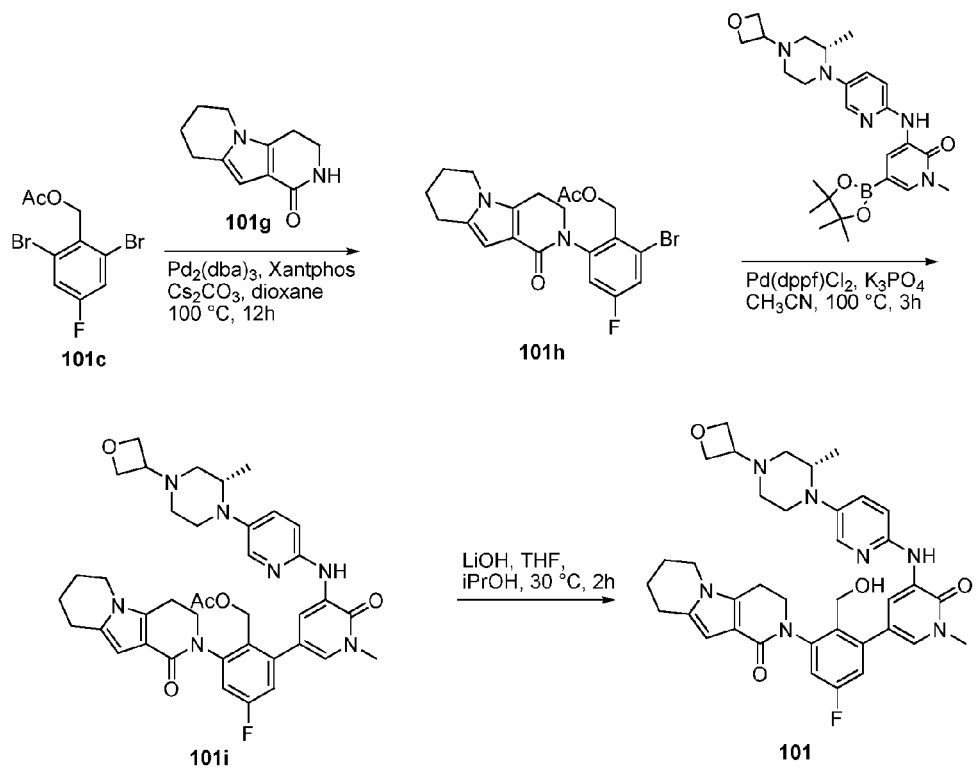
Figure 2:
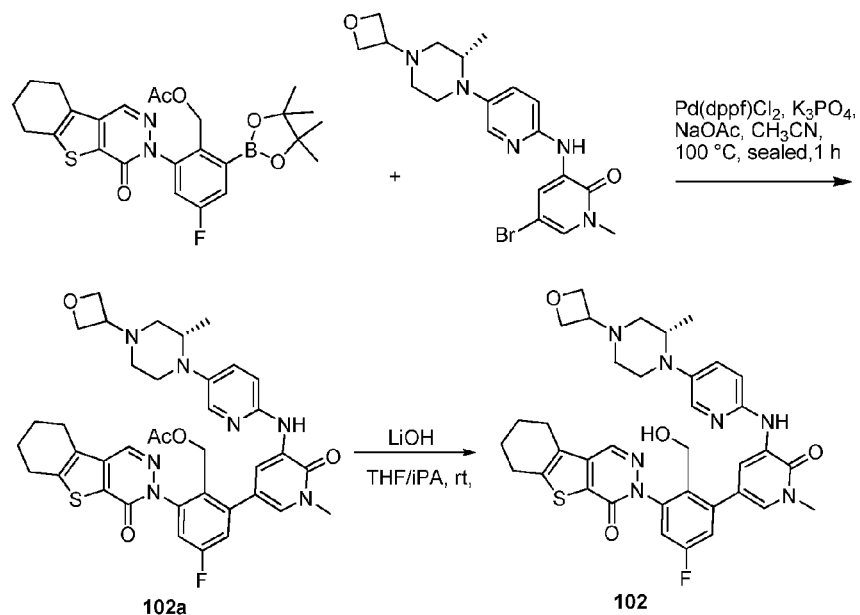
Figure 3:
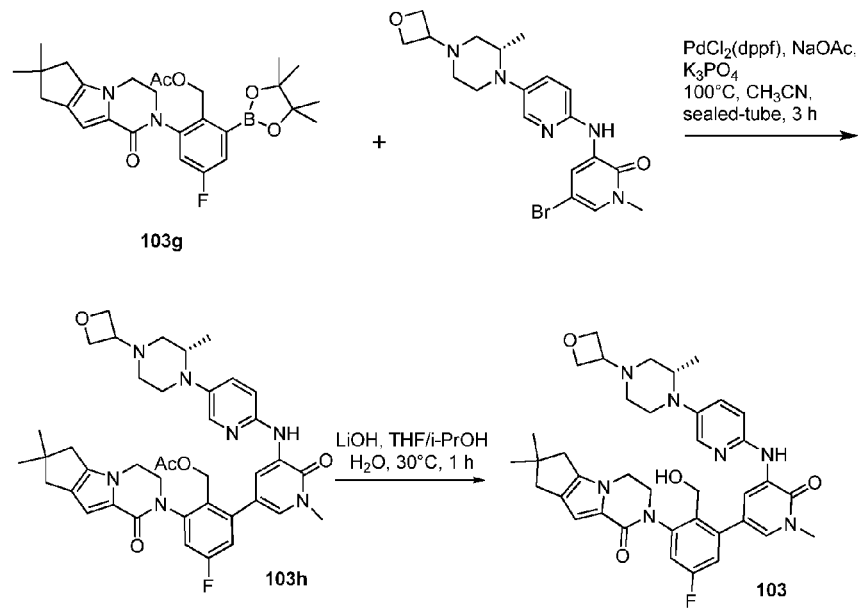
Figure 4A:
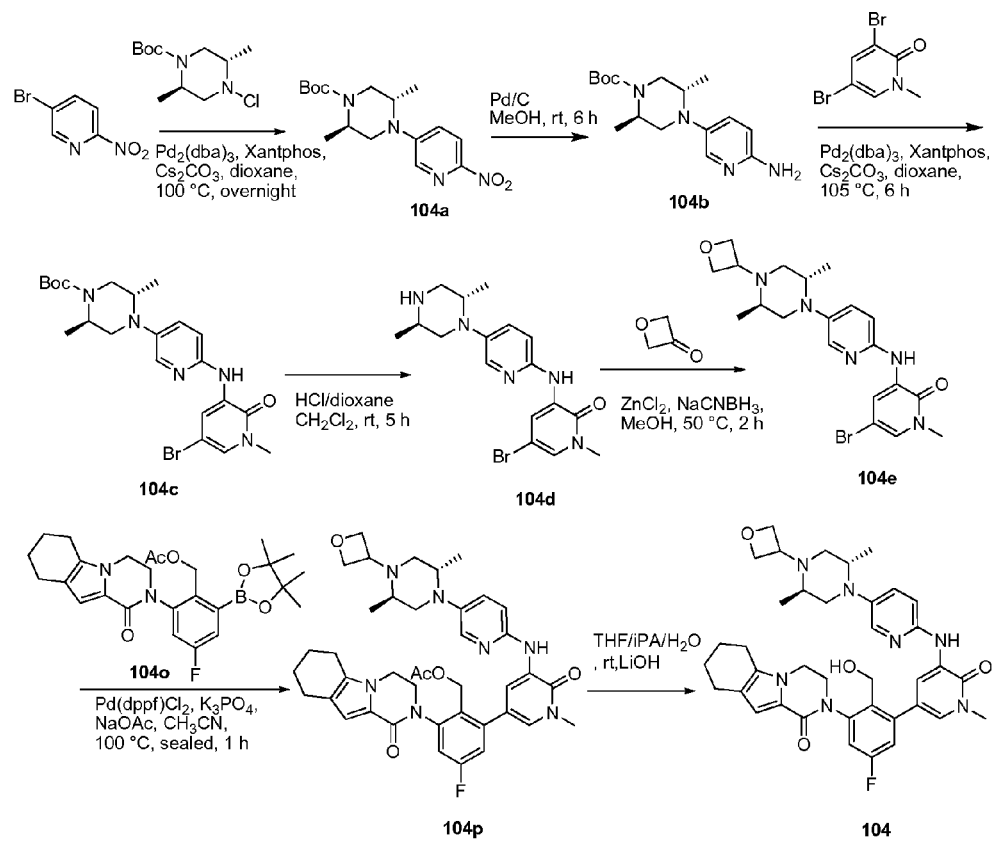
Figure 4B:
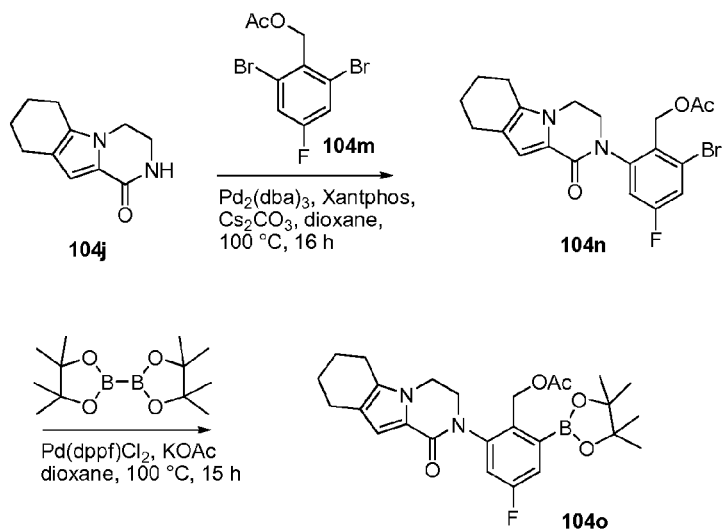
FIG. 4b shows the preparation of 4-Fluoro-2-(1-oxo-3,4,6,7,8,9-hexahydro-pyrazino[1,2-a]indol-2(1H)-yl)-6-(4,4,5,5-tetramethyl-1,3,2-dioxaborolan-2-yl)benzyl acetate 104o from 3,4,6,7,8,9-Hexahydropyrazino[1,2-a]indol-1(2H)-one 104j.
Figure 5:
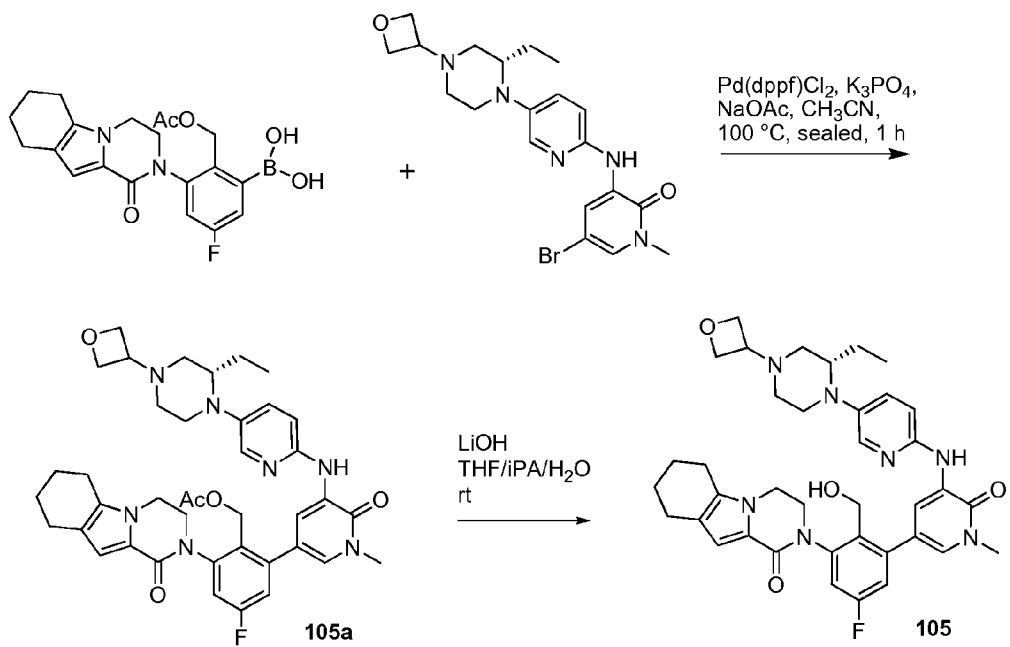
Figure 6:
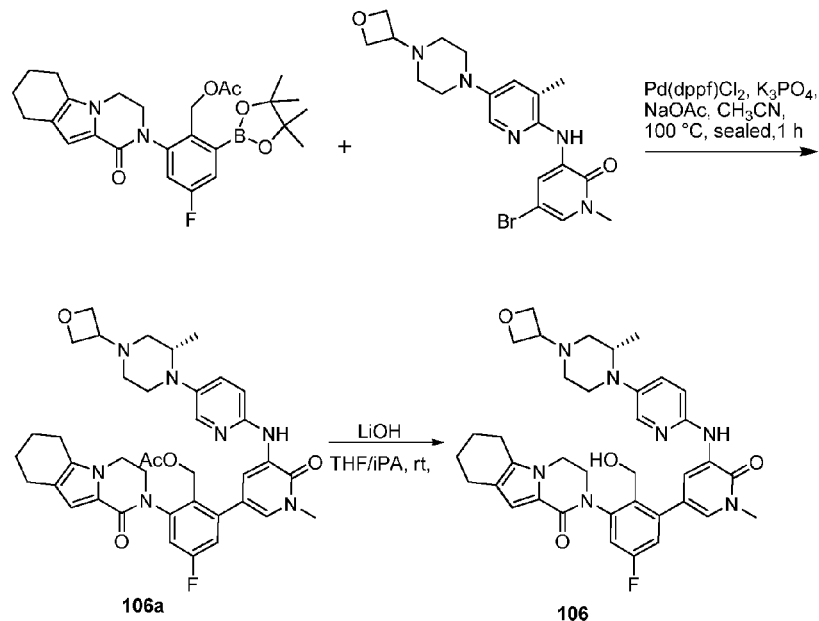
Figure 7:
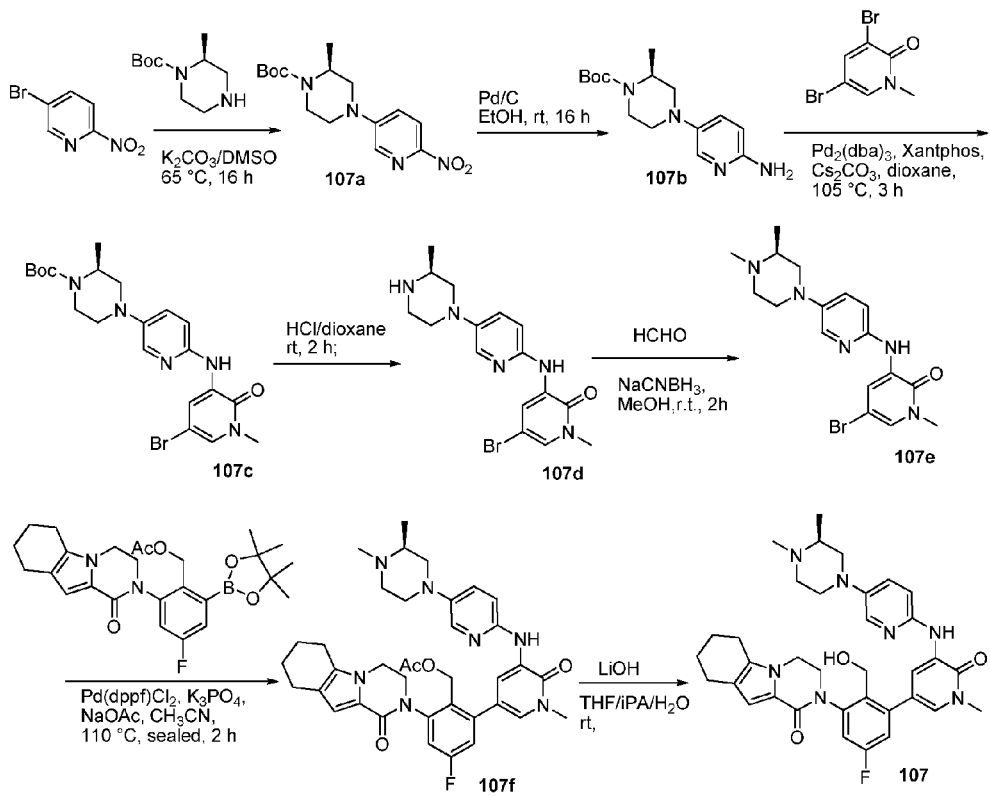
Figure 8:
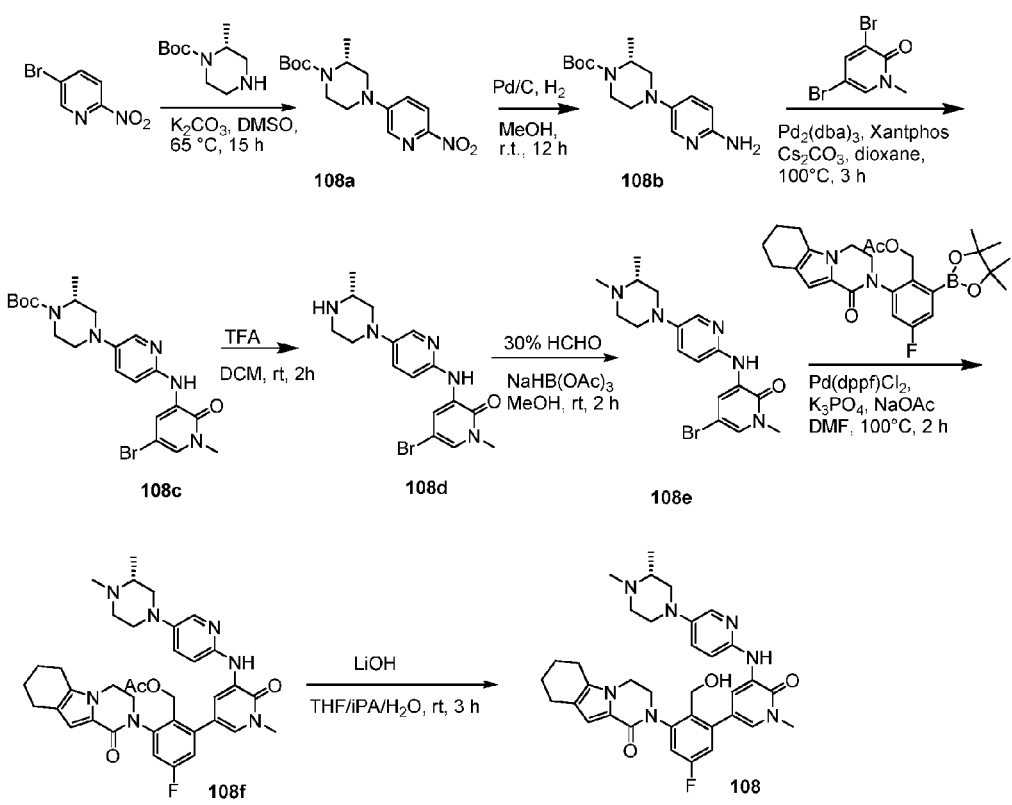
Figure 9:
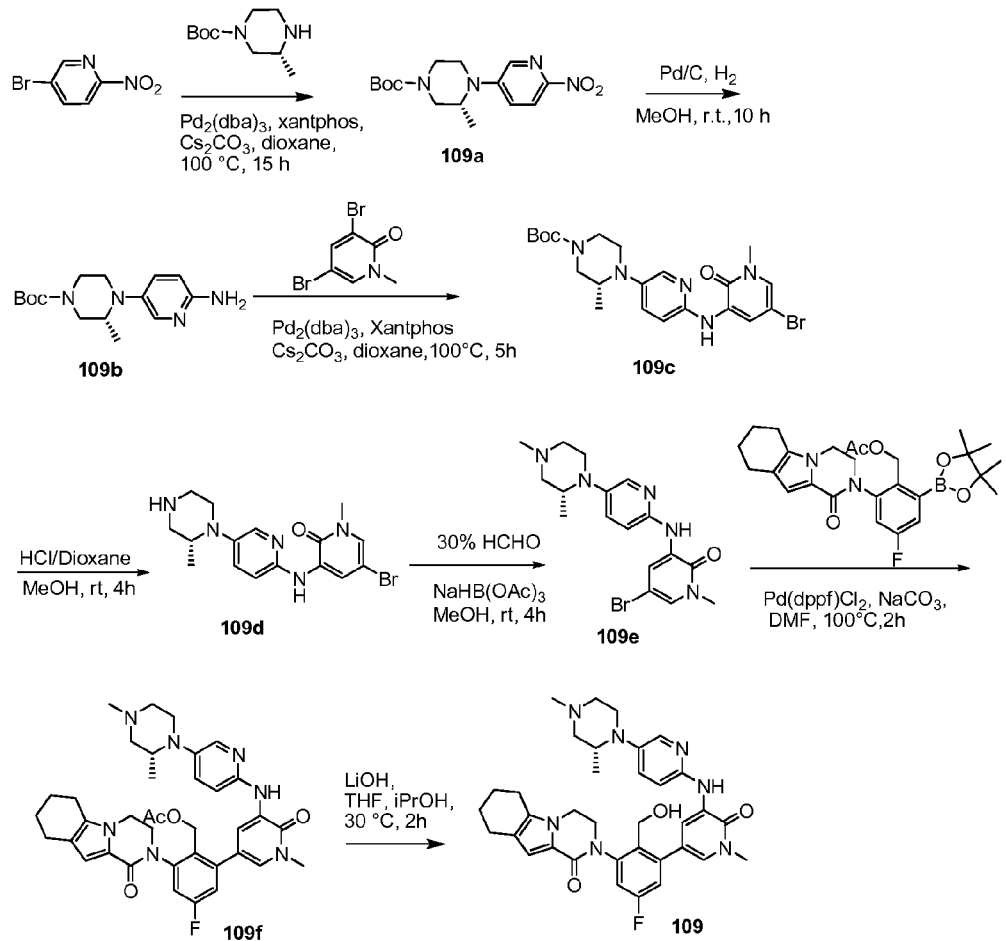
Figure 10:
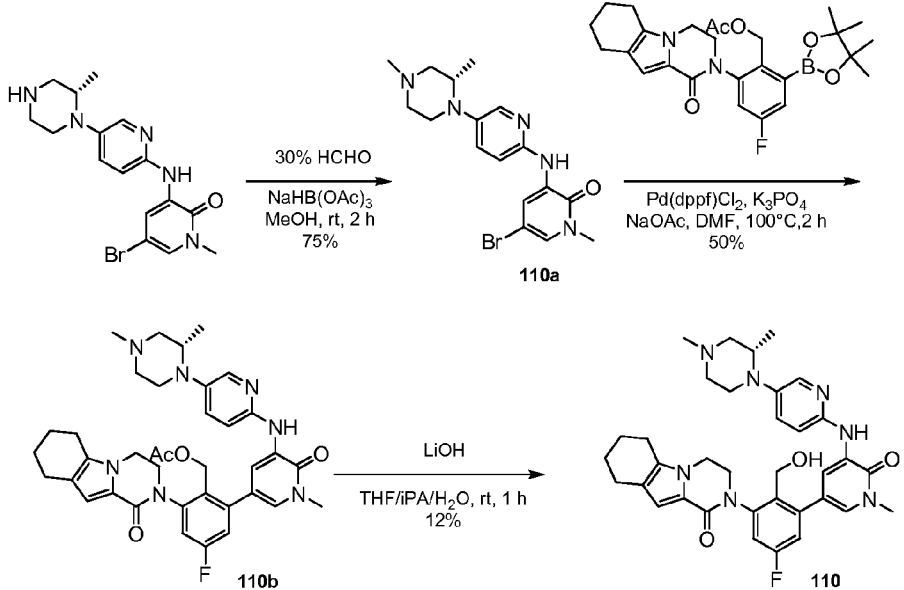
Figure 11:
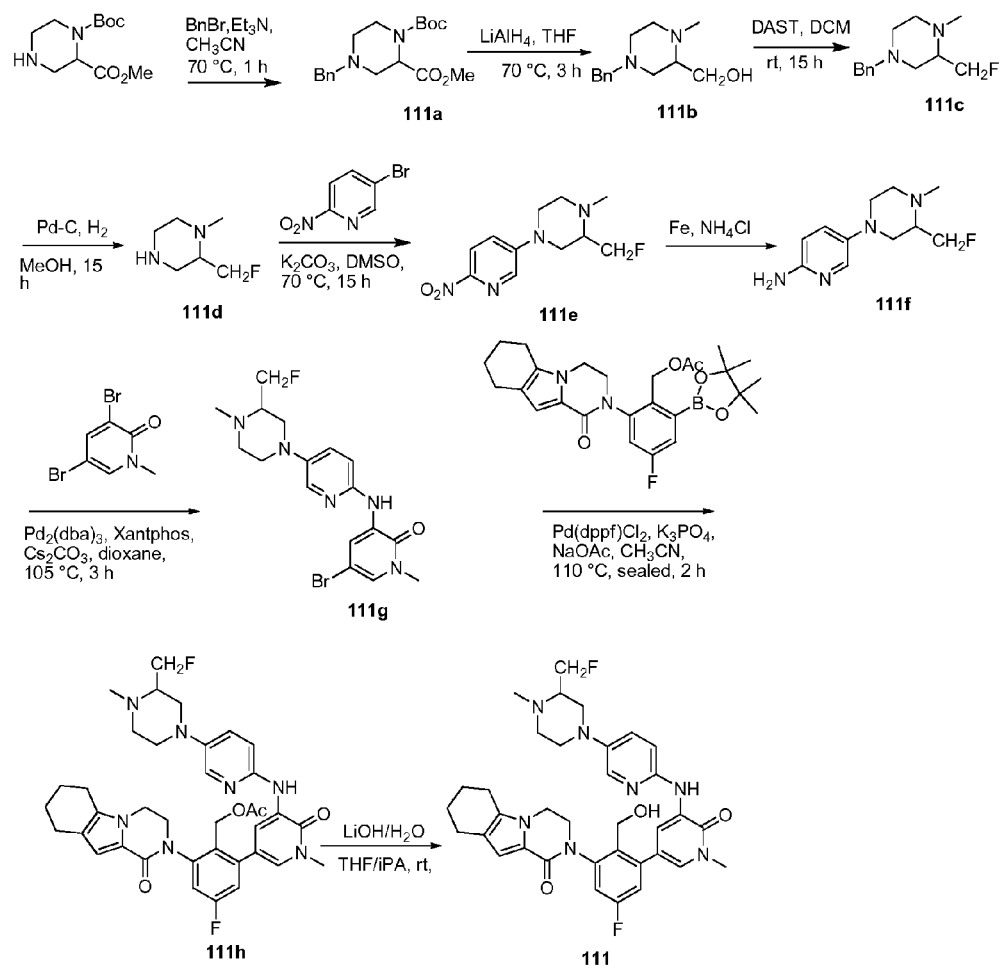

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this application is based on IUPAC systematic nomenclature, unless indicated otherwise.

DEFINITIONS

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo

[2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms ("cancer"), and they are generally treated by specialists in hematology and/or oncology. In some centers "Hematology/oncology" is a single subspecialty of internal medicine while in others they are considered separate divisions (there are also surgical and radiation oncologists). Not all hematological disorders are malignant ("cancerous"); these other blood conditions may also be managed by a hematologist. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (all subtypes).

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR®, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA®, Johnson & Johnson), ABRAXANE® (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the Btk inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Table 1 structures for illustrative purposes, while stereochemical determination awaits, such as x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., may be calculated.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Alkylated Piperazine Compounds

The present invention provides alkylated piperazine compounds of Formula I, and pharmaceutical formulations thereof, which are potentially useful in the treatment of diseases, conditions and/or disorders modulated by Btk kinase Exemplary embodiments of Formula I compounds include

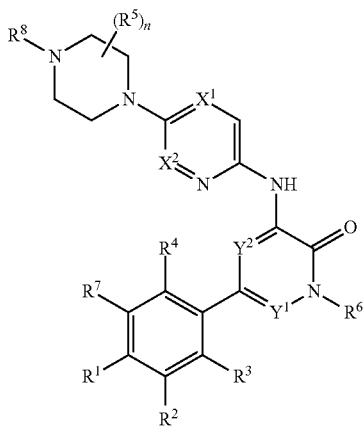

I or stereoisomers, tautomers, or pharmaceutically acceptable salts thereof, wherein:

$R^1$, $R^2$ and $R^3$ are independently selected from H, F, Cl, —$NH_2$, —$NHCH_3$, —$N(CH_3)_2$, —OH, —$OCH_3$, —$OCH_2CH_3$, —$OCH_2CH_2OH$, and $C_1$-$C_3$ alkyl;

$R^4$ is selected from H, F, Cl, CN, —$CH_2OH$, —$CH(CH_3)OH$, —$C(CH_3)_2OH$, —$CH(CF_3)OH$, —$CH_2F$, —$CHF_2$, —$CH_2CHF_2$, —$CF_3$, —$C(O)NH_2$, —$C(O)NHCH_3$, —$C(O)N(CH_3)_2$, —$NH_2$, —$NHCH_3$, —$N(CH_3)_2$, —$NHC(O)CH_3$, —OH, —$OCH_3$, —$OCH_2CH_3$, —$OCH_2CH_2OH$, cyclopropyl, cyclopropylmethyl, 1-hydroxycyclopropyl, imidazolyl, pyrazolyl, 3-hydroxy-oxetan-3-yl, oxetan-3-yl, and azetidin-1-yl;

$R^5$ is selected from —$CH_3$, —$CH_2CH_3$, —$CH_2OH$, —$CH_2F$, —$CHF_2$, —$CF_3$, —CN, and —$CH_2CH_2OH$;

or two $R^5$ groups form a 3-, 4-, 5-, or 6-membered carbocyclic or heterocyclic ring;

or an $R^5$ group and an $R^8$ group form a 3-, 4-, 5-, or 6-membered carbocyclic or heterocyclic ring;

n is 1, 2, 3, or 4

$R^6$ is selected from H, F, —$CH_3$, —$CH_2CH_3$, —$CH_2CH_2OH$, —$NH_2$, and —OH;

$R^7$ is selected from the structures:

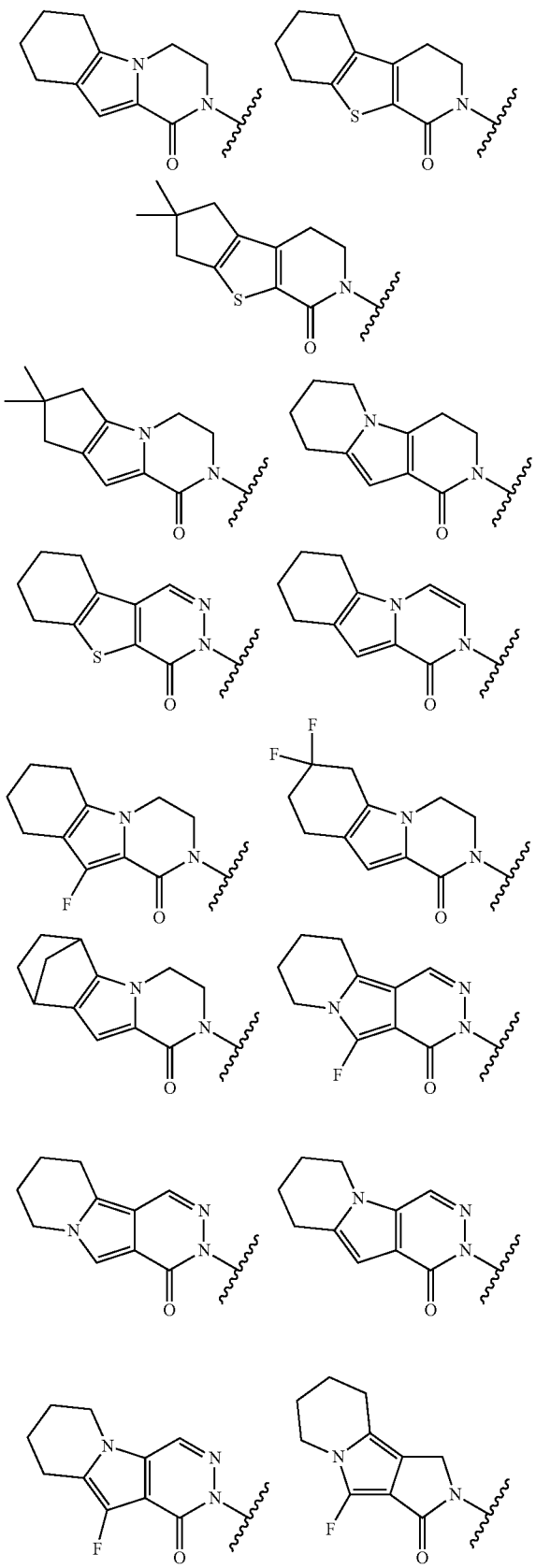

-continued

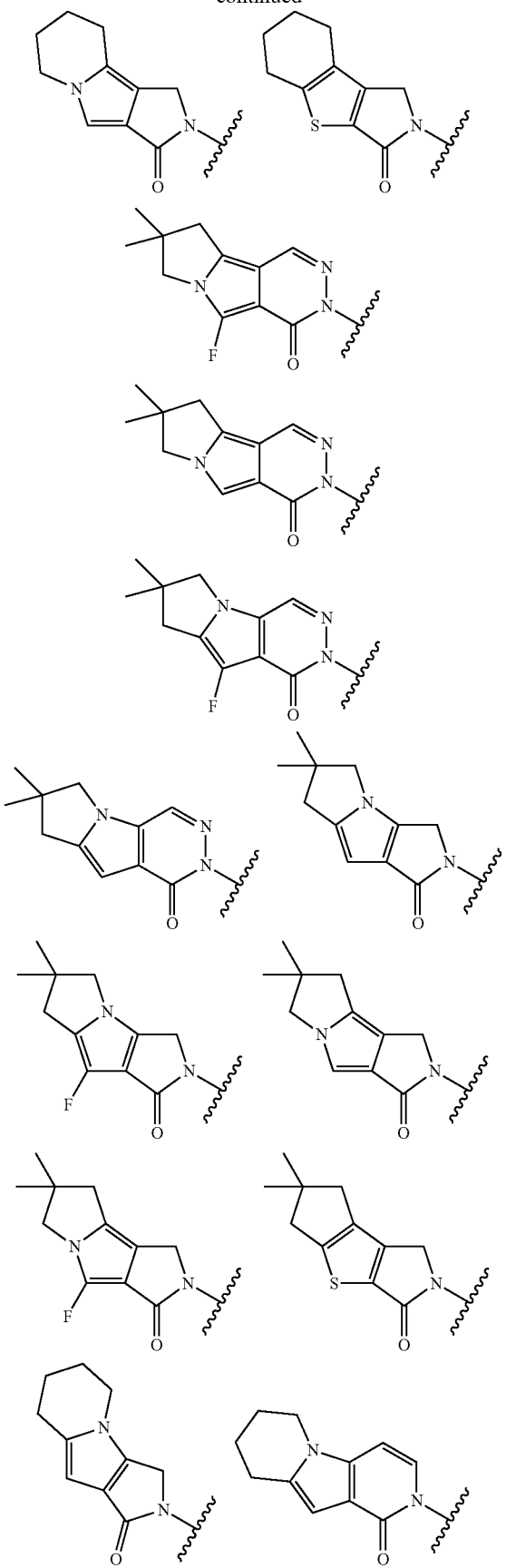
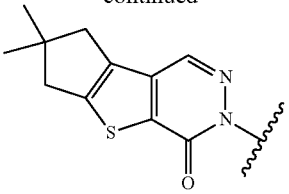

where the wavy line indicates the site of attachment;

$R^8$ is selected from —$CH_3$, —$S(O)_2CH_3$, cyclopropyl, azetidin-3-yl, oxetan-3-yl, and morpholin-4-yl;

$X^1$ is $CR^9$ or N, where $R^9$ is selected from H, F, Cl, —$CH_3$, —$CH_2CH_3$, —$CH_2CH_2OH$, —$NH_2$, —$NHCH_3$, —$N(CH_3)_2$, —OH, —$OCH_3$, —$OCH_2CH_3$, and —$OCH_2CH_2OH$;

$X^2$ is $CR^{10}$ or N, where $R^{10}$ is selected from H, —$CH_3$, —$CH_2CH_3$, and —$CH_2CH_2OH$; and $Y^1$ and $Y^2$ are independently selected from CH and N, where $Y^1$ and $Y^2$ are not each N.

Exemplary embodiments of Formula I compounds include wherein X is $CR^9$, and $R^9$ is H.

Exemplary embodiments of Formula I compounds include wherein X is N.

Exemplary embodiments of Formula I compounds include wherein $R^4$ is —$CH_2OH$.

Exemplary embodiments of Formula I compounds include wherein $R^2$ is F.

Exemplary embodiments of Formula I compounds include wherein $R^1$ and $R^3$ are H.

Exemplary embodiments of Formula I compounds include wherein $R^6$ is $CH_3$.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all diastereomers, including cis-trans (geometric) and conformational isomers. For example, if a Formula I compound incorporates a double bond or a fused ring, the cis- and trans-forms, as well as mixtures thereof, are embraced within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Formula I compounds were tested by a standard biochemical Btk Kinase Assay (Example 901).

A general procedure for a standard cellular Btk Kinase Assay that can be used to test Formula I compounds is a Ramos Cell Btk Assay (Example 902).

A standard cellular B-cell proliferation assay can be used to test Formula I compounds with B-cells purified from spleen of Balb/c mice (Example 903).

A standard T cell proliferation assay can be used to test Formula I compounds with T-cells purified from spleen of Balb/c mice (Example 904).

A CD86 Inhibition assay can be conducted on Formula I compounds for the inhibition of B cell activity using total mouse splenocytes purified from spleens of 8-16 week old Balb/c mice (Example 905).

A B-ALL Cell Survival Assay can be conducted on Formula I compounds to measure the number of viable B-ALL cells in culture (Example 906).

A CD69 Whole Blood Assay can be conducted on Formula I compounds to determine the ability of compounds to inhibit the production of CD69 by B lymphocytes in human whole blood activated by crosslinking surface IgM with goat F(ab')2 anti-human IgM (Example 907). CD69 is a type II C-type lectin involved in lymphocyte migration and cytokine secretion. CD69 expression represents one of the earliest available indicators of leukocyte activation and its rapid induction occurs through transcriptional activation (Vazquez et al (2009) Jour. of Immunology Published Oct. 19, 2009, doi: 10.4049/jimmunol.0900839). Concentration-dependent inhibition of antigen receptor stimulation by selective Btk inhibitors induces cell surface expression of the lymphocyte activation marker CD69 (Honigberg et al (2010) Proc. Natl. Acad. Sci. 107(29):13075-13080). Thus, CD69 inhibition by selective Btk inhibitors may be correlated with therapeutic efficacy of certain B-cell disorders. The CD69 Hu Blood FACS IC70 values are displayed for exemplary Formula I compounds in Tables 1 and 2.

The cytotoxic or cytostatic activity of Formula I exemplary compounds can be measured by: establishing a proliferating mammalian tumor cell line in a cell culture medium, adding a Formula I compound, culturing the cells for a period from about 6 hours to about 5 days; and measuring cell viability (Example 908). Cell-based in vitro assays are used to measure viability, i.e. proliferation ($IC_{50}$), cytotoxicity ($EC_{50}$), and induction of apoptosis (caspase activation) and may be useful in predicting clinical efficacy against hematological malignancies and solid tumors.

The in vitro potency of the combinations of Formula I compounds with chemotherapeutic agents can be measured by the cell proliferation assay of Example 908; the CellTiter-Glo® Luminescent Cell Viability Assay, commercially available from Promega Corp., Madison, Wis. This homogeneous assay method is based on the recombinant expression of Coleoptera luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602, 677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiterGlo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative efficacy of Formula I exemplary compounds and combinations with chemotherapeutic agents are measured by the CellTiter-Glo® Assay (Example 908) against certain hematological tumor cell lines. $EC_{50}$ values are established for the tested compounds and combinations.

Exemplary Formula I compounds in Tables 1 and 2 were made, characterized, and tested for inhibition of Btk according to the methods of this invention, and have the following structures and corresponding names (ChemDraw Ultra, Version 9.0.1, and ChemBioDraw, Version 11.0, CambridgeSoft Corp., Cambridge Mass.). Where more than one name is associated with a Formula I compound or intermediate, the chemical structure shall define the compound.

TABLE 1

| No. | Structure | IUPAC Name | Mol Weight | CD69 Hu Blood FACS IC70 (μM) |
|---|---|---|---|---|
| 101 | 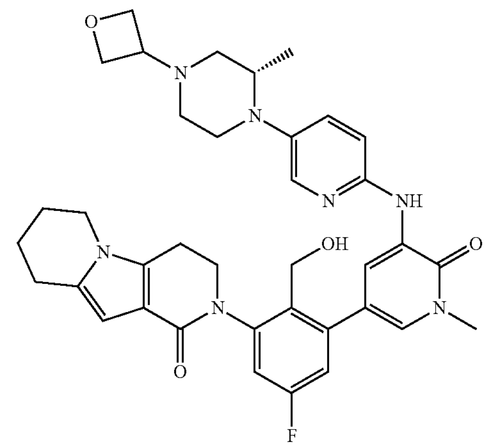 [SMILES: C[C@H]1CN(C2COC2)CCN1c1ccc(Nc2cc(-c3cc(F)cc(N4CCc5c(cc6n5CCCC6)C4=O)c3CO)cn(C)c2=O)nc1] | (S)-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrido[3,4-b]indolizin-1(2H)-one | 669 | 0.0338 |
| 102 | 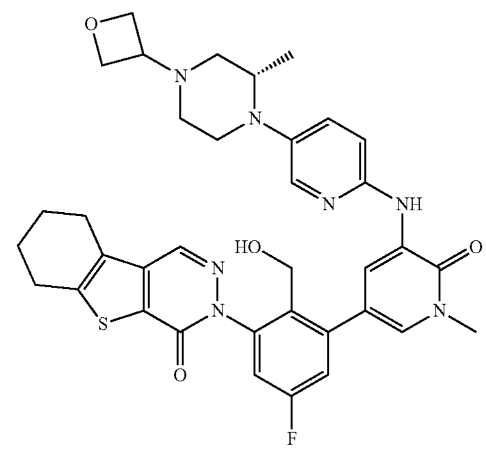 [SMILES: C[C@H]1CN(C2COC2)CCN1c1ccc(Nc2cc(-c3cc(F)cc(-n4ncc5c6c(sc5c4=O)CCCC6)c3CO)cn(C)c2=O)nc1] | (S)-5-[5-fluoro-2-(hydroxymethyl)-3(1-methyl-5-(5-(2-methyl-4-(oxetan-3-yl)piperazin-1-yl)pyridin-2-ylamino)-6-oxo-1,6-dihydropyridin-3-yl)phenyl]-8-thia-4,5-diazatricyclo[7.4.0.02,7]trideca-1(9),2(7),3-trien-6-one | 684 | 0.031 |
| 103 | 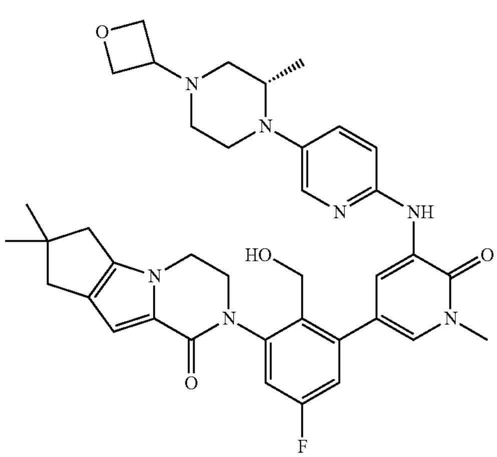 | (2S)-10-[5-fluoro-2-(hydroxymethyl)-3-[1-methyl-5-({5-[2-methyl-4-(oxetan-3-yl)piperazin-1-yl]pyridine-2-yl}amino)-6-oxo-1,6-dihydropyridin-3-yl]phenyl]-4,4-dimethyl-1,10-diazatricyclo[6.4.0.02,6]dodeca-2(6),7-dien-9-one | 682 | 0.0145 |

TABLE 1-continued

| No. | Structure | IUPAC Name | Mol Weight | CD69 Hu Blood FACS IC70 (μM) |
|-----|-----------|------------|------------|-------------------------------|
| 104 | 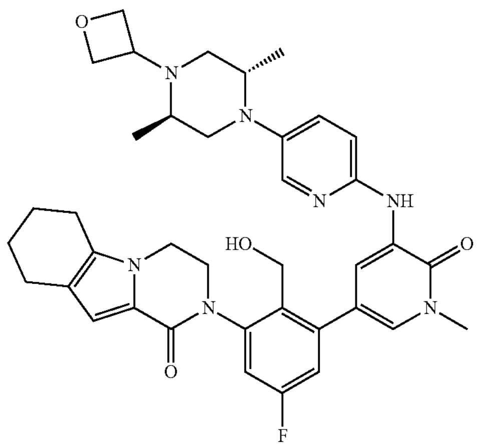 [SMILES: C[C@@H]1CN(c2ccc(Nc3cc(-c4cc(F)cc(N5CCn6c(cc7c6CCCC7)C5=O)c4CO)cn(C)c3=O)nc2)[C@@H](C)CN1C1COC1] | 2-(3-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one | 682 | 0.015 |
| 105 | 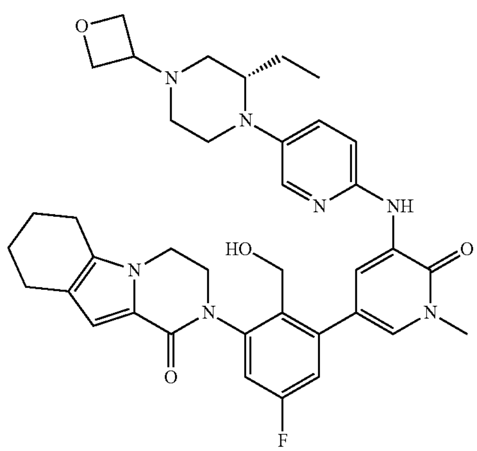 [SMILES: CC[C@H]1CN(C2COC2)CCN1c1ccc(Nc2cc(-c3cc(F)cc(N4CCn5c(cc6c5CCCC6)C4=O)c3CO)cn(C)c2=O)nc1] | (S)-2-(3-(5-(5-(2-ethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one | 682 | 0.008 |
| 106 | 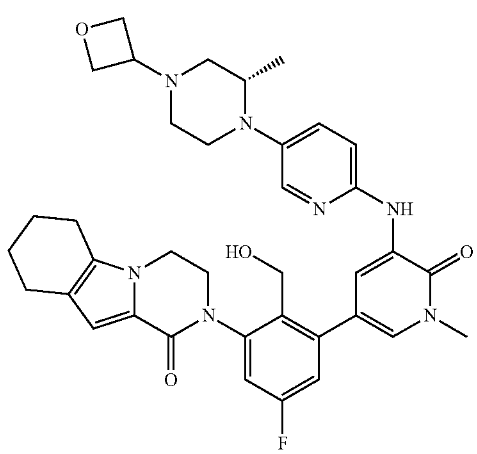 [SMILES: C[C@H]1CN(C2COC2)CCN1c1ccc(Nc2cc(-c3cc(F)cc(N4CCn5c(cc6c5CCCC6)C4=O)c3CO)cn(C)c2=O)nc1] | (S)-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one | 668 | 0.019 |

TABLE 1-continued

| No. | Structure | IUPAC Name | Mol Weight | CD69 Hu Blood FACS IC70 (μM) |
|---|---|---|---|---|
| 107 | 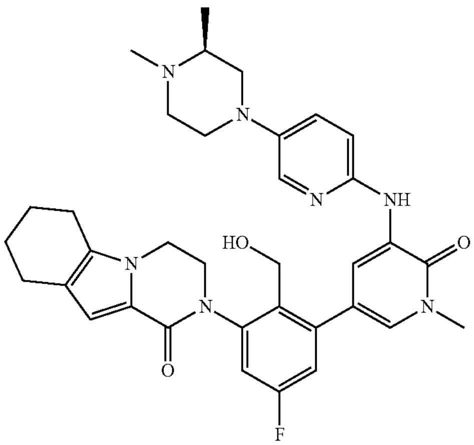 [SMILES: C[C@H]1CN(c2ccc(Nc3cc(-c4cc(F)cc(N5CCn6c(cc7c6CCCC7)C5=O)c4CO)cn(C)c3=O)nc2)CCN1C] | (S)-2-(3-(5-(5-(3,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one | 626 | 0.044 |
| 108 | 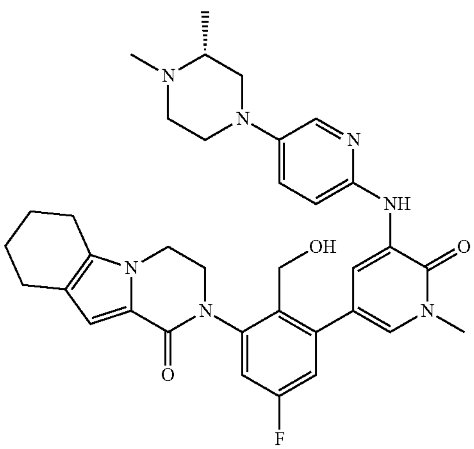 [SMILES: C[C@@H]1CN(c2ccc(Nc3cc(-c4cc(F)cc(N5CCn6c(cc7c6CCCC7)C5=O)c4CO)cn(C)c3=O)nc2)CCN1C] | (R)-2-(3-(5-(5-(3,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one | 626 | 0.023 |
| 109 | 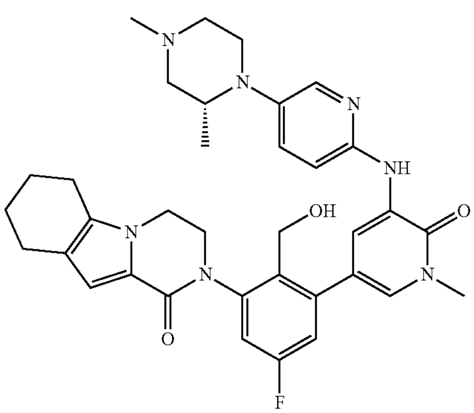 [SMILES: C[C@@H]1CN(C)CCN1c1ccc(Nc2cc(-c3cc(F)cc(N4CCn5c(cc6c5CCCC6)C4=O)c3CO)cn(C)c2=O)nc1] | (R)-2-(3-(5-(5-(2,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one | 626 | 0.029 |

TABLE 1-continued

| No. | Structure | IUPAC Name | Mol Weight | CD69 Hu Blood FACS IC70 (μM) |
|---|---|---|---|---|
| 110 | 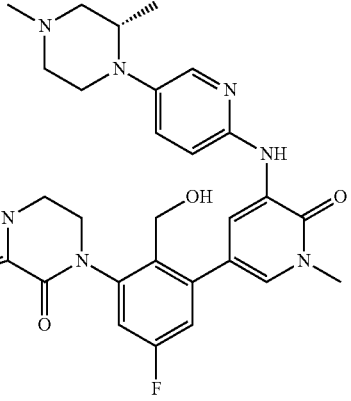 | (S)-2-(3-(5-(5-(2,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one | 626 | 0.006 |
| 111 | 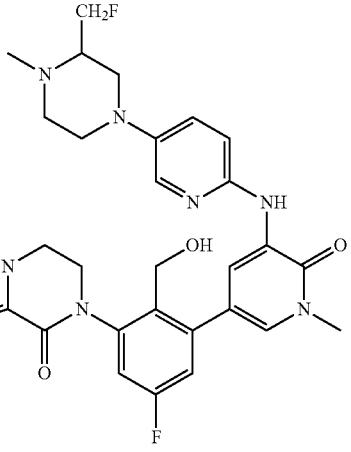 | 2-(5-fluoro-3-(5-(5-(3-(fluoromethyl)-4-methylpiperazin-1-yl)pyridin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one | 644 | 0.092 |
| 112 | 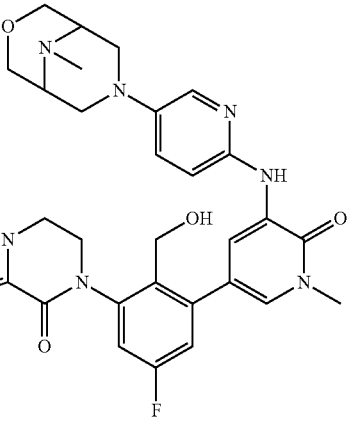 | 2-(5-fluoro-2-(hydroxymethyl)-3-(1-methyl-5-(5-(9-methyl-7-oxa-3,9-diaza-bicyclo[3.3.1]nonan-3-yl)pyridin-2-ylamino)-6-oxo-1,6-dihydropyridin-3-yl)phenyl)-3,4,6,7,8,9-hexahydropyrazino[1,2-a]indol-1(2H)-one | 654 | 0.17 |

TABLE 1-continued

| No. | Structure | IUPAC Name | Mol Weight | CD69 Hu Blood FACS IC70 (μM) |
|---|---|---|---|---|
| 113 | 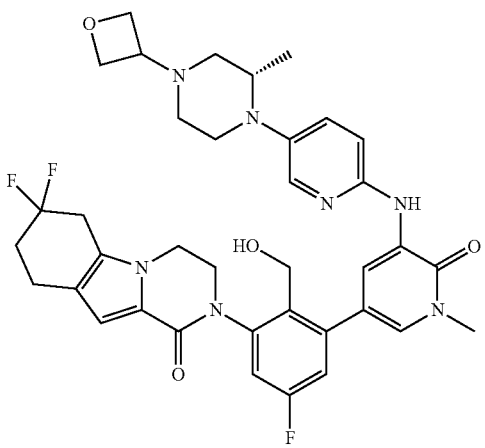 [SMILES: C[C@H]1CN(C2COC2)CCN1c1ccc(Nc2cc(-c3cc(F)cc(N4CCn5c(cc6c5CC(F)(F)CC6)C4=O)c3CO)cn(C)c2=O)nc1] | (S)-7,7-difluoro-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one | 703.75 | |
| 114 | 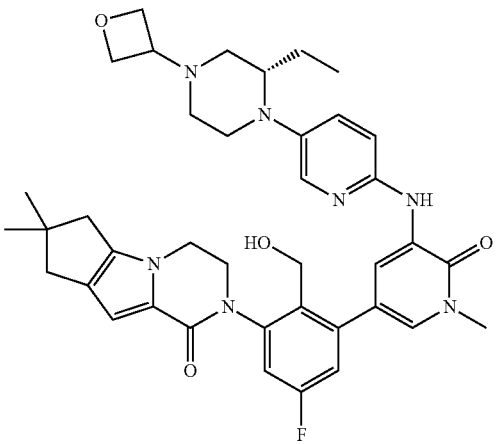 | 2-(3-{5-[5-((S)-2-Ethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-7,7-dimethyl-3,4,7,8-tetrahydro-2H,6H-cyclopenta[4,5]pyrrolo[1,2-a]pyrazin-1-one | 695.83 | |
| 115 | 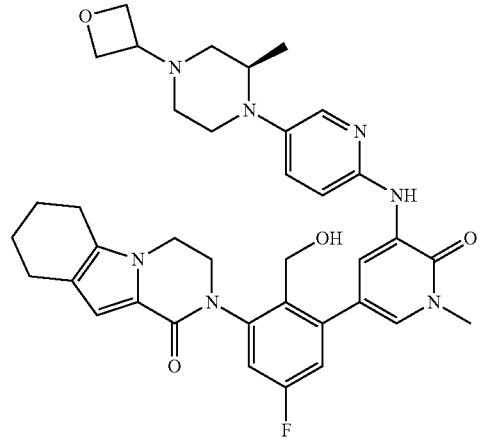 [SMILES: C[C@@H]1CN(C2COC2)CCN1c1ccc(Nc2cc(-c3cc(F)cc(N4CCn5c(cc6c5CCCC6)C4=O)c3CO)cn(C)c2=O)nc1] | (R)-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one | 667.77 | |

TABLE 1-continued

| No. | Structure | IUPAC Name | Mol Weight | CD69 Hu Blood FACS IC70 (µM) |
|---|---|---|---|---|
| 116 | 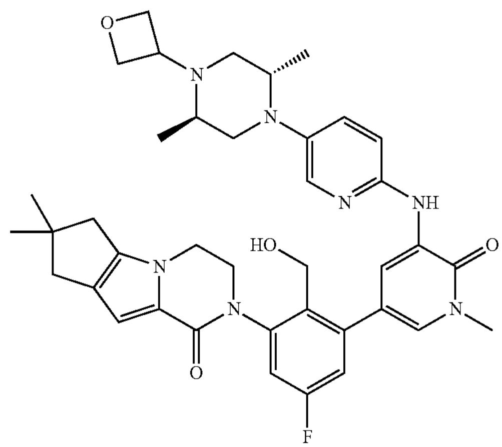 | 2-(3-{5-[5-((2S,5R)-2,5-Dimethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-7,7-dimethyl-3,4,7,8-tetrahydro-2H,6H-cyclopenta[4,5]pyrrolo[1,2-a]pyrazin-1-one | 695.83 | |
| 117 | 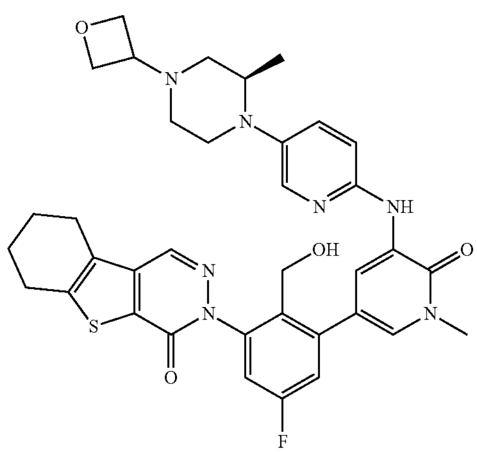 [SMILES: C[C@@H]1CN(C2COC2)CCN1c1ccc(Nc2cc(-c3cc(F)cc(-n4ncc5c6c(sc5c4=O)CCCC6)c3CO)cn(C)c2=O)nc1] | 3-(5-Fluoro-2-hydroxymethyl-3-{1-methyl-5-[5-((R)-2-methyl-4-oxetan-3-yl-piperazin-1-yl)-pyridin-2-ylamino]-6-oxo-1,6-dihydro-pyridin-3-yl}-phenyl)-6,7,8,9-tetrahydro-3H-benzo[4,5]thieno[2,3-d]pyridazin-4-one | 683.79 | |
| 118 | 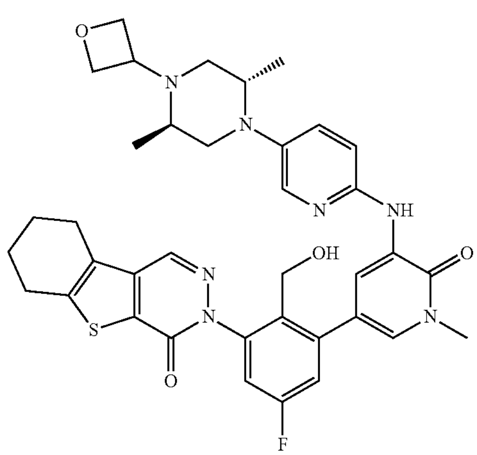 [SMILES: C[C@@H]1CN(c2ccc(Nc3cc(-c4cc(F)cc(-n5ncc6c7c(sc6c5=O)CCCC7)c4CO)cn(C)c3=O)nc2)[C@@H](C)CN1C1COC1] | 3-(3-{5-[5-((2S,5R)-2,5-Dimethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-6,7,8,9-tetrahydro-3H-benzo[4,5]thieno[2,3-d]pyridazin-4-one | 697.82 | |

TABLE 1-continued

| No. | Structure | IUPAC Name | Mol Weight | CD69 Hu Blood FACS IC70 (μM) |
|---|---|---|---|---|
| 119 | 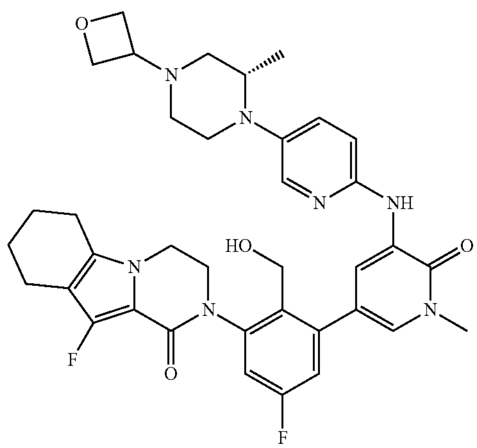 [SMILES: C[C@H]1CN(C2COC2)CCN1c1ccc(Nc2cc(-c3cc(F)cc(N4CCn5c6c(c(F)c5C4=O)CCCC6)c3CO)cn(C)c2=O)nc1] | (S)-10-fluoro-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one | 685.76 | |
| 120 | 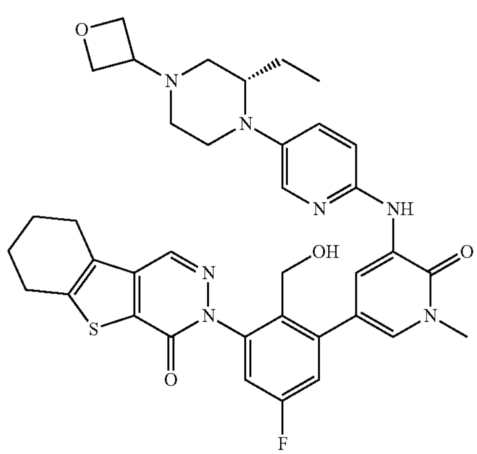 [SMILES: CC[C@H]1CN(C2COC2)CCN1c1ccc(Nc2cc(-c3cc(F)cc(-n4ncc5c6c(sc5c4=O)CCCC6)c3CO)cn(C)c2=O)nc1] | 3-(3-{5-[5-((S)-2-Ethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-6,7,8,9-tetrahydro-3H-benzo[4,5]thieno[2,3-d]pyridazin-4-one | 697.82 | |
| 121 | 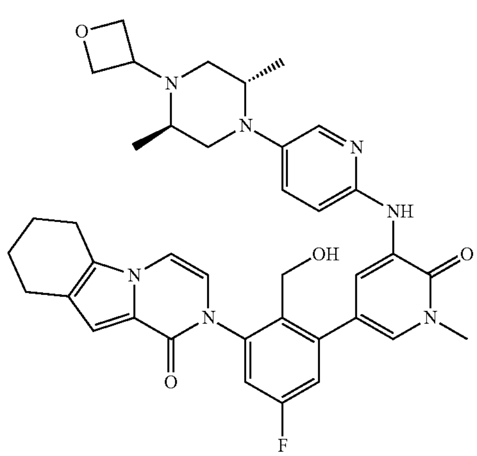 [SMILES: C[C@@H]1CN(c2ccc(Nc3cc(-c4cc(F)cc(-n5ccn6c7c(cc6c5=O)CCCC7)c4CO)cn(C)c3=O)nc2)[C@@H](C)CN1C1COC1] | 2-(3-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-6,7,8,9-tetrahydropyrazino[1,2-a]indol-1(2H)-one | 679.78 | |

TABLE 1-continued

| No. | Structure | IUPAC Name | Mol Weight | CD69 Hu Blood FACS IC70 (μM) |
|---|---|---|---|---|
| 122 | 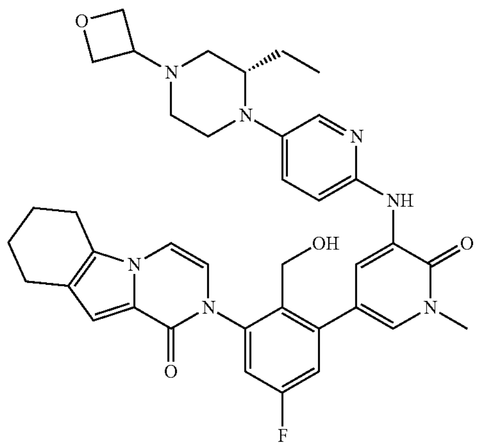 [SMILES: CC[C@H]1CN(C2COC2)CCN1c1ccc(Nc2cc(-c3cc(F)cc(-n4ccn5c6c(cc5c4=O)CCCC6)c3CO)cn(C)c2=O)nc1] | (S)-2-(3-(5-(5-(2-ethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-6,7,8,9-tetrahydropyrazino[1,2-a]indol-1(2H)-one | 680.78 | |
| 123 | 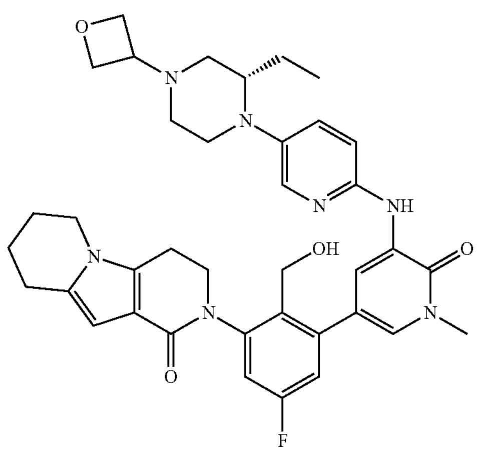 [SMILES: CC[C@H]1CN(C2COC2)CCN1c1ccc(Nc2cc(-c3cc(F)cc(N4CCc5c(cc6n5CCCC6)C4=O)c3CO)cn(C)c2=O)nc1] | (S)-2-(3-(5-(5-(2-ethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrido[3,4-b]indolizin-1(2H)-one | 681.80 | |
| 124 | 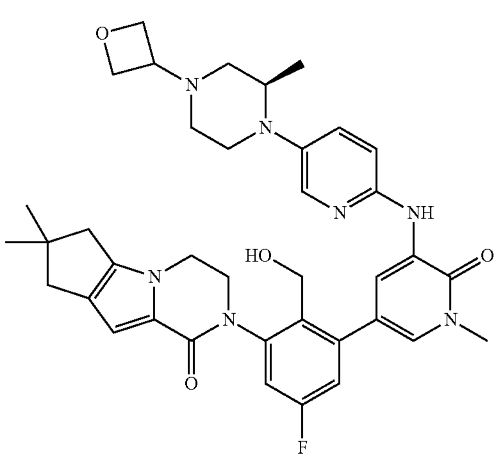 | 2-(5-Fluoro-2-hydroxymethyl-3-{1-methyl-5-[5-((R)-2-methyl-4-oxetan-3-yl-piperazin-1-yl)-pyridin-2-ylamino]-6-oxo-1,6-dihydro-pydin-3-yl}-phenyl)-7,7-dimethyl-3,4,7,8-tetrahydro-2H,6H-cyclopenta[4,5]pyrrolo[1,2-a]pyrazin-1-one | 681.80 | |

TABLE 1-continued

| No. | Structure | IUPAC Name | Mol Weight | CD69 Hu Blood FACS IC70 (μM) |
|---|---|---|---|---|
| 125 | 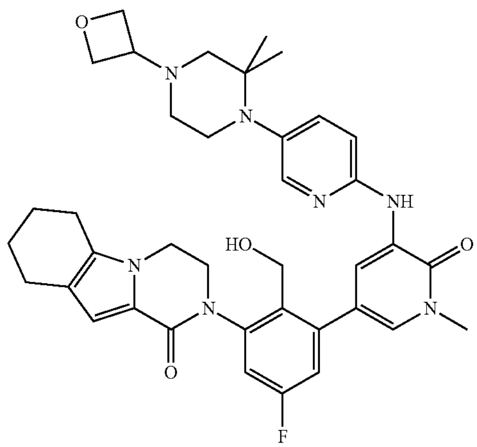 [SMILES: Cn1cc(-c2cc(F)cc(N3CCn4c(cc5c4CCCC5)C3=O)c2CO)cc(Nc2ccc(N3CCN(C4COC4)CC3(C)C)cn2)c1=O] | 2-(3-(5-(5-(2,2-dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one | 681.80 | |

TABLE 2

| No. | Structure | IUPAC Name | CD69 Hu Blood FACS (IC70) |
|---|---|---|---|
| 126 | 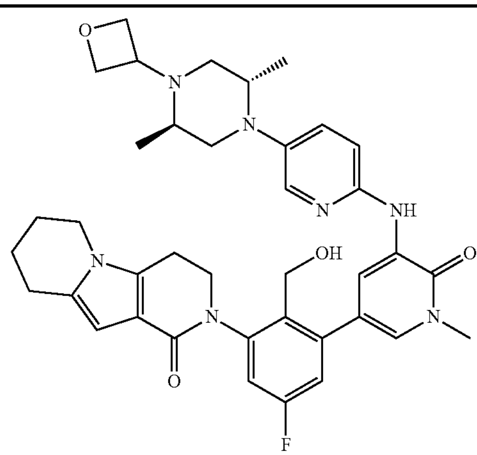 | 2-[3-[5-[[5-[(2S,5R)-2,5-dimethyl-4-(oxetan-3-yl)piperazin-1-yl]-2-pyridyl]amino]-1-methyl-6-oxo-3-pyridyl]-5-fluoro-2-(hydroxymethyl)phenyl]-3,4,6,7,8,9-hexahydropyrido[3,4-b]indolizin-1-one | 0.0571 |
| 127 | 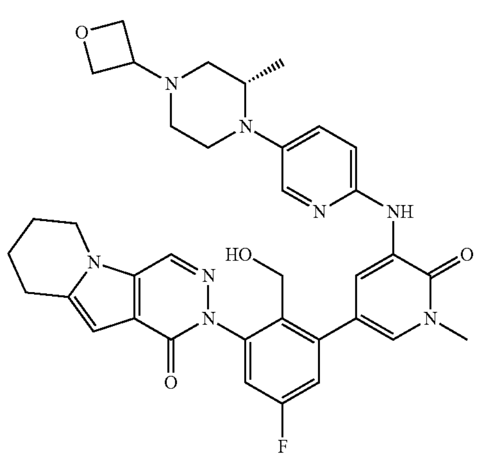 [SMILES: C[C@H]1CN(C2COC2)CCN1c1ccc(Nc2cc(-c3cc(F)cc(-n4ncc5c(cc6n5CCCC6)c4=O)c3CO)cn(C)c2=O)nc1] | 2-[5-fluoro-2-(hydroxymethyl)-3-[1-methyl-5-[[5-[(2S)-2-methyl-4-(oxetan-3-yl)piperazin-1-yl]-2-pyridyl]amino]-6-oxo-3-pyridyl]phenyl]-6,7,8,9-tetrahydropyridazino[4,5-b]indolizin-1-one | 0.051 |

TABLE 2-continued

| No. | Structure | IUPAC Name | CD69 Hu Blood FACS (IC70) |
|---|---|---|---|
| 128 | 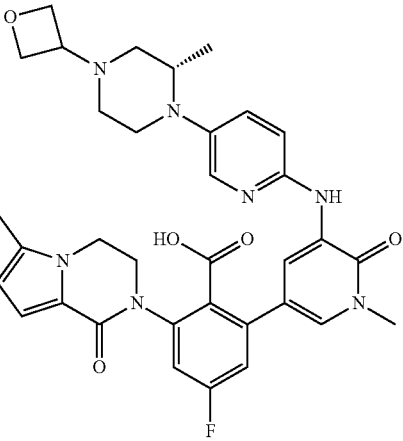 | 2-(7,7-dimethyl-4-oxo-1,2,6,8-tetrahydrocyclopenta[3,4]pyrrolo[3,5-b]pyrazin-3-yl)-4-fluoro-6-[1-methyl-5-[[5-[(2S)-2-methyl-4-(oxetan-3-yl)piperazin-1-yl]-2-pyridyl]amino]-6-oxo-3-pyridyl]benzoic acid | 5 |
| 129 | 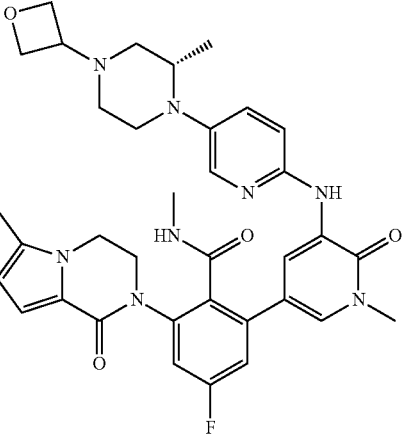 | 2-(7,7-dimethyl-4-oxo-1,2,6,8-tetrahydrocyclopenta[3,4]pyrrolo[3,5-b]pyrazin-3-yl)-4-fluoro-N-methyl-6-[1-methyl-5-[[5-[(2S)-2-methyl-4-(oxetan-3-yl)piperazin-1-yl]-2-pyridyl]amino]-6-oxo-3-pyridyl]benzamide | 0.472 |
| 130 | 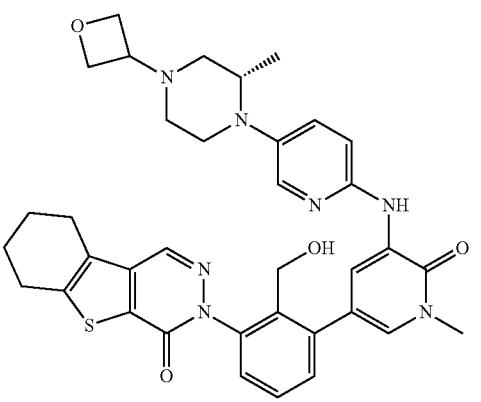 [SMILES: C[C@H]1CN(C2COC2)CCN1c1ccc(Nc2cc(-c3cccc(-n4ncc5c6c(sc5c4=O)CCCC6)c3CO)cn(C)c2=O)nc1] | 3-[2-(hydroxymethyl)-3-[1-methyl-5-[[5-[(2S)-2-methyl-4-(oxetan-3-yl)piperazin-1-yl]-2-pyridyl]amino]-6-oxo-3-pyridyl]phenyl]-6,7,8,9-tetrahydrobenzothiopheno[2,3-d]pyridazin-4-one | 0.0354 |

TABLE 2-continued

| No. | Structure | IUPAC Name | CD69 Hu Blood FACS (IC70) |
|---|---|---|---|
| 131 | 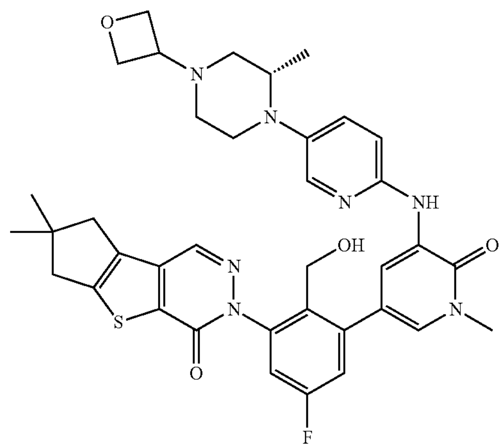 | 3-[5-fluoro-2-(hydroxymethyl)-3-[1-methyl-5-[[5-[(2S)-2-methyl-4-(oxetan-3-yl)piperazin-1-yl]-2-pyridyl]amino]-6-oxo-3-pyridyl]phenyl]-7,7-dimethyl-6,8-dihydrocyclopenta[3,4]thieno[1,3-d]pyridazin-4-one | 0.0349 |

Administration of Formula I Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with Btk kinase such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Methods of the invention also include treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjogren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

The methods of the invention can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of Btk activity may result in reduced amounts of reperfusion injury in such situations.

Pharmaceutical Formulations

In order to use a compound of this invention for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, solvate, metabolite, or pharmaceutically acceptable salt or prodrug thereof, and the use of at least one other cancer treatment method. The amounts of the compound(s) of Formula I and the other pharmaceutically active therapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The Figures and Examples provide exemplary methods for preparing Formula I compounds. Those skilled in the art will appreciate that other synthetic routes may be used to synthesize the Formula I compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Experimental procedures, intermediates and reagents useful for useful for the preparation of Formula I compounds may be found in U.S. Ser. No. 13/102,720, "PYRIDONE AND AZA-PYRIDONE COMPOUNDS AND METHODS OF USE", filed 6 May 2011, which is incorporated by reference in its entirety.

FIGS. 1-12 describe the synthesis of exemplary embodiments of Formula I compounds 101-125, more fully described in Examples 101-112, and may be useful for the preparation of other Formula I compounds.

General Preparative Procedures

General Procedure: Suzuki Coupling

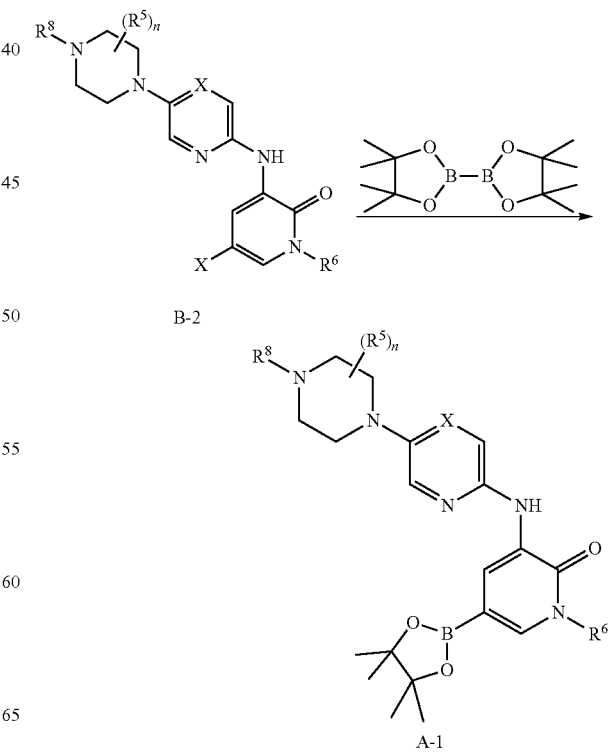

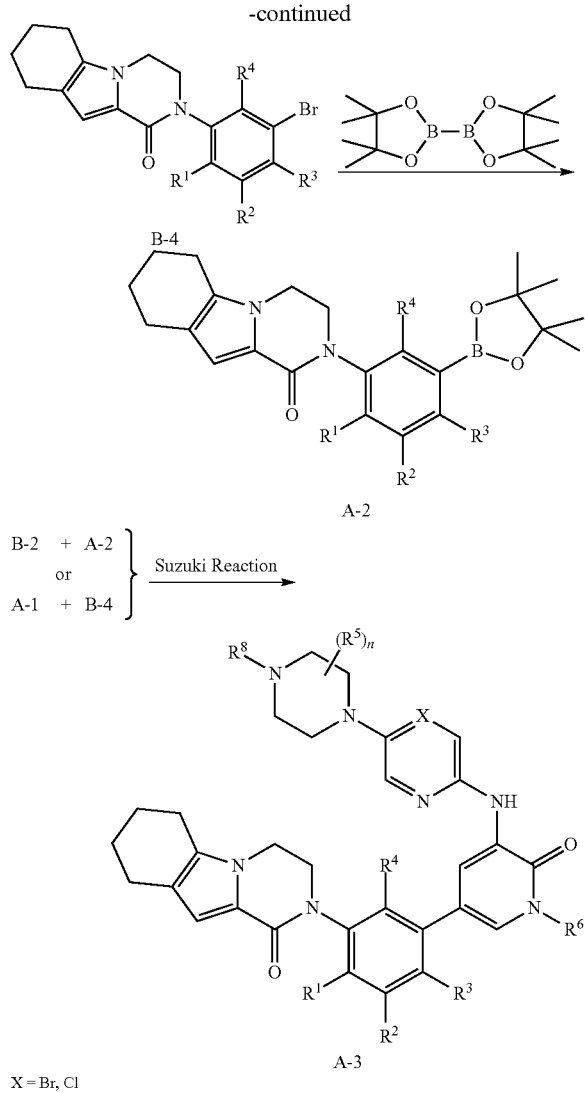

X = Br, Cl

The Suzuki-type coupling reaction is useful to form carbon-carbon bonds to attach the rings of Formula I compounds and intermediates such as A-3 (Suzuki (1991) Pure Appl. Chem. 63:419-422; Miyaura and Suzuki (1979) Chem. Reviews 95(7):2457-2483; Suzuki (1999) J. Organometal. Chem. 576:147-168). Suzuki coupling is a palladium mediated cross coupling reaction of an arylhalide, such as B-2 or B-4, with a boronic acid such as A-1 or A-2. For example, B-2 may be combined with about 1.5 equivalents of 4,4,4',4',5,5,5',5'-octamethyl-2,2'-bi(1,3,2-dioxaborolane), and dissolved in about 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. In some cases potassium acetate is used in place of sodium carbonate to adjust the pH of the aqueous layer. The reaction is then heated to about 140-150° C. under pressure in a microwave reactor (Biotage AB, Uppsala, Sweden) for 10 to 30 minutes. The contents are extracted with ethyl acetate, or another organic solvent. After evaporation of the organic layer the boron ester A-1 may be purified on silica or by reverse phase HPLC. Substituents are as defined, or protected forms or precursors thereof. Likewise, bromide intermediate B-4 can be boronylated to give A-2.

Suzuki coupling of B-2 and A-2, or of A-1 and B-4, gives Formula I compound or intermediate A-3. Boronic ester (or acid) (1.5 eq) A-1 or A-2, and a palladium catalyst such as bis(triphenylphosphine)palladium(II) chloride (0.05 eq) is added to a mixture of halo intermediate (1 eq) B-2 or B-4 in acetonitrile and 1 M of sodium carbonate aqueous solution (equal volume as acetonitrile). The reaction mixture is heated to about 150° C. in a microwave for about 15 min. LC/MS indicates when the reaction is complete. Water is added to the mixture, and the precipitated product is filtered and purified by HPLC to yield the product A-3. Substituents are as defined, or protected forms or precursors thereof.

A variety of palladium catalysts can be used during the Suzuki coupling step. Various low valent, Pd(II) and Pd(0) catalysts may be used in the Suzuki coupling reaction, including PdCl2(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd[P(o-tol)$_3$]$_2$, Pd$_2$(dba)$_3$/P(o-tol)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Cl$_2$Pd[P(4-COOH-Ph)(Ph)$_2$]$_2$, and encapsulated catalysts Pd EnCat™30, Pd EnCat™ TPP30, and Pd(II)EnCat™ BINAP30 (US 2004/0254066).

General Procedure: Buchwald Reaction

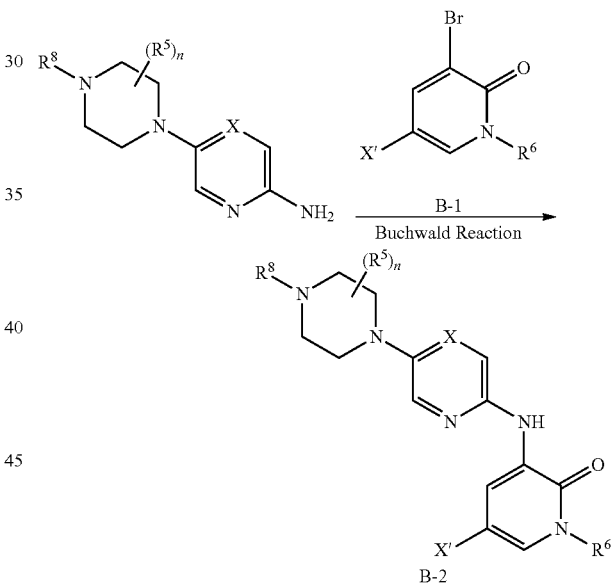

X = N, CR$^9$
X' = Br, Cl

The Buchwald reaction is useful to aminate 6-bromo intermediates B-1 (Wolf and Buchwald (2004) Org. Synth Coll. Vol. 10:423; Paul et al (1994) Jour. Amer. Chem. Soc. 116: 5969-5970). To a solution of 3,5-dihalo-pyridone intermediate B-1 in DMF is added the appropriate 5-(piperazin-1-yl) pyridin-2-amine, e.g. 104b, or 5-(piperazin-1-yl)pyrazin-2-amine (200 mol %), Cs$_2$CO$_3$ (50 mol %), Pd$_2$(dba)$_3$ (5 mol %), and 4,5-bis(diphenylphosphino)-9,9-dimethylxanthene (Xantphos, CAS Reg. No. 161265-03-8, 10 mol %). The reaction is heated to about 110° C. under pressure in a microwave reactor (Biotage AB, Uppsala, Sweden) for about 30 min. The resulting solution is concentrated in vacuo to give B-2. Other palladium catalysts and phosphine ligands may be useful.

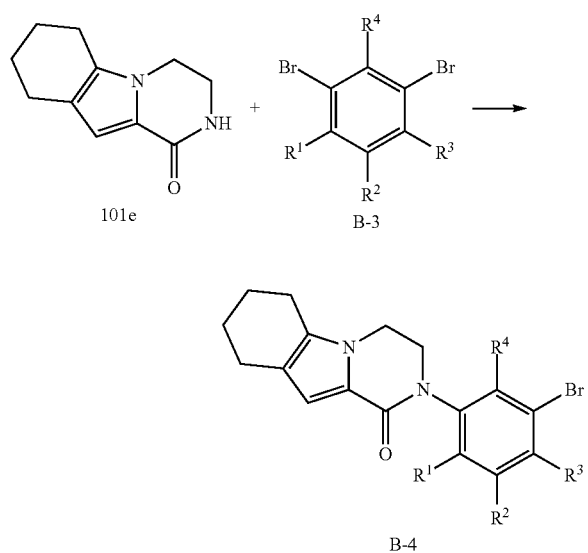

N-Aryl amide intermediates B-4 can also be prepared under Buchwald conditions with cyclic amide intermediates (R[7]) such as 3,4,6,7,8,9-hexahydropyrazino[1,2-a]indol-1 (2H)-one 101e and aryl bromides B-3.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

EXAMPLES

Example 101a 2,6-Dibromo-4-fluorobenzaldehyde 101a

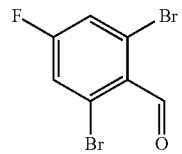

101a

A solution of 1,3-dibromo-5-fluoro-2-iodobenzene (50 g, 132 mmol) in anhydrous toluene (300 mL) was cooled to −35° C. A solution of isopropylmagnesium chloride (84 mL, 171 mmol, 2.0 M in diethyl ether) over a period of 30 minutes while maintaining the internal temperature below −25° C. See FIG. 1. A clear brown solution was obtained. Stirring was continued for 1.5 h. Then anhydrous DMF (34 mL, 436 mmol) was added over a period of 30 minutes. The temperature of the reaction mixture increased to −19° C. The reaction mixture was warmed to 10° C. (room temperature) over 1 h and stirred at this temperature for 1.5 h. The reaction was quenched with saturated aqueous $NH_4Cl$ (100 mL), filtered and evaporated under reduced pressure. The residue was purified by silica-gel column chromatography (eluting with petroleum ether/ethyl acetate: from 50:1 to 20:1) to give 101a (20 g, yield 54%) as a yellow solid.

Example 101b 2,6-Dibromo-4-fluorophenyl)methanol 101b

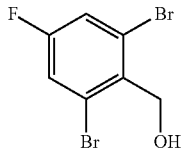

101b

A solution of 2,6-dibromo-4-fluorobenzaldehyde 101a (20 g, 71 mmol) in ethanol (500 mL) was added $NaBH_4$ (10 g, 284 mmol). The mixture was stirred at room temperature (10° C.) for 4 h. TLC showed the start material disappeared. The reaction was qunched with HCl solution (150 mL, 1 M). Most of ethanol was evaporated at reduced pressure. The residue was extracted by ethyl acetate (3×500 mL). The organic layers was combined and dried with anhy. $Na_2SO_4$, evaporated in vacuo. The residue was purified by silica-gel column chromatography (eluting with petroleum ether/ethyl acetate: from 50:1 to 20:1) to give 101b (15 g, yield 75%) as a white solid.

Example 101c 2,6-Dibromo-4-fluorobenzyl acetate 101c

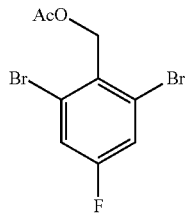

101c

A 500-mL single-neck round-bottomed flask equipped with a magnetic stirrer and nitrogen inlet was charged with 101b (23.0 g, 81.0 mmol), triethyl amine (25.0 g, 247 mmol) in anhydrous methylene chloride (100 mL). Acetic anhydride (10.0 g, 98.0 mmol) was added and this mixture was stirred at room temperature for 16 h. After this time, the mixture was diluted with methylene chloride (100 mL) and washed with saturated aqueous sodium bicarbonate (100 mL). The layers were separated and the aqueous layer was extracted with methylene chloride (2×20 mL). The organic extracts were combined and dried over sodium sulfate. The drying agent was removed by filtration. The filtrate was concentrated under reduced pressure, and the resulting residue was purified by flash column chromatography (silica, 0% to 50% ethyl acetate/hexanes) to afford 101c in 87% yield (23.0 g) as a white solid.

Example 101d

Methyl 5,6,7,8-Tetrahydroindolizine-2-carboxylate 112d

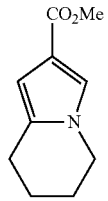

101d

A 500-mL round-bottomed flask equipped with a magnetic stirrer and nitrogen inlet was purged with nitrogen and charged with 5,6,7,8-tetrahydroindolizine-2-carboxylic acid (30.4 g, 184 mmol), DMF (1.00 g, 13.6 mmol) and methylene chloride (300 mL). The solution was cooled to 0° C. using an ice bath. Oxalyl chloride (28.0 g, 221 mmol) was added dropwise, and the reaction mixture was warmed to room temperature over 30 min and stirred for 5 h. After this time, the resulting solution was concentrated to afford a brown solid. This solid was dissolved in anhydrous methanol (400 mL), and the solution was cooled to 0° C. Triethylamine (57 g, 552 mmol) was added to the reaction mixture, and it was stirred for a further 2 h at room temperature. After this time, the reaction mixture was concentrated to dryness under reduced pressure. The residue was diluted with methylene chloride (300 mL) and washed with water (200 mL) and saturated aqueous sodium bicarbonate (200 mL). The organic layer was dried over sodium sulfate, filtered and concentrated under reduced pressure. The resulting residue was titrated with hexane (200 mL) to afford 101d in 58% yield (19.1 g) as a white solid: mp 72-74° C.; $^1$H NMR (300 MHz, DMSO-$d_6$) δ 7.13 (s, 1H), 6.23 (s, 1H), 3.93 (t, 2H, J=6.0 Hz), 3.77 (s, 3H), 2.75 (t, 2H, J=6.0 Hz), 1.93 (m, 2H), 1.80 (m, 2H); (APCI+) m/z 180.1 (M+H)

Example 101e

Methyl 3-(Cyanomethyl)-5,6,7,8-tetrahydroindolizine-2-carboxylate 101e

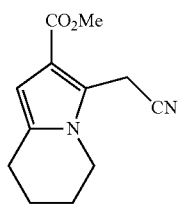

A 500-mL three-neck round-bottomed flask equipped with an addition funnel, thermometer and charged with methyl 5,6,7,8-tetrahydroindolizine-2-carboxylate 101d (6.70 g, 37.4 mmol), iodoacetonitrile (12.5 g, 74.9 mmol), iron (II) sulfate heptahydrate (5.20 g, 18.7 mmol) and dimethyl sulfoxide (250 mL). Hydrogen peroxide (35%, 18.2 g, 187 mmol) was added dropwise to the mixture in 1 h through a syringe pump at room temperature using a water bath. Iron (II) sulfate heptahydrate (2 to 3 equivalent) was added to the reaction mixture in portions to keep the temperature between 25° C. to 35° C., until the color of the reaction mixture is deep red. If TLCs show the reaction not completed, then more hydrogen peroxide (2-3 equivalent) and more iron (II) sulfate heptahydrate (1-2 equivalent) were added in the same manner until the reaction is completed. After that time, the reaction mixture was partitioned between aqueous saturated sodium bicarbonate solution (200 mL) and ethyl acetate (400 mL). The organic layer was separated, and the aqueous layer was extracted with ethyl acetate (2×100 mL). The combined organic layers were washed with saturated Sodium thiosulfate solution (50 mL), dried over sodium sulfate and concentrated under reduced pressure. The residue was purified by column chromatography to afford a 78% yield (6.40 g) of 101e as a yellow oil: $^1$H NMR (500 MHz, CDCl$_3$) δ 6.23 (s, 1H), 4.23 (s, 2H), 3.94 (t, 2H, J=6.5 Hz), 3.81 (s, 3H), 2.74 (t, 2H, J=6.5 Hz), 2.00 (m, 2H), 1.83 (m, 2H); (APCI+) m/z 219.3 (M+H)

Example 101f

Methyl 3-(2-Aminoethyl)-5,6,7,8-tetrahydroindolizine-2-carboxylate Hydrogen Chloride Salt 101f

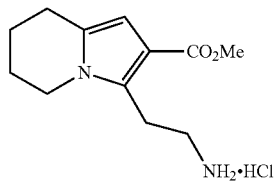

Methyl 3-(Cyanomethyl)-5,6,7,8-tetrahydroindolizine-2-carboxylate 101e was hydrogenated with platinum oxide catalyst under 50 psi of hydrogen in ethanol and ethyl acetate in the presence of hydrogen chloride overnight at room temperature to give 101f (380 mg, 1.74 mmol) which was used in directly in the next step.

Example 101g 3,4,6,7,8,9-Hexahydropyrido[3,4-b]indolizin-1(2H) one 101g

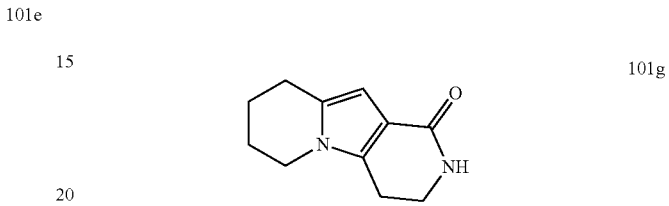

A 100-mL single-neck round-bottomed flask equipped with a magnetic stirrer and nitrogen inlet was purged with nitrogen and charged with methyl 3-(2-aminoethyl)-5,6,7,8-tetrahydroindolizine-2-carboxylate hydrogen chloride salt 101f (prepared above, estimated 1.74 mmol, presuming quantitative yield), sodium ethoxide (354 mg, 5.22 mmol) and ethanol (20 mL). The mixture was stirred at 55° C. for 5 h. After that time, the reaction mixture was concentrated under reduced pressure and the residue was partitioned between ethyl acetate (200 mL) and water (100 mL). The organic layer was separated, and the aqueous layer was extracted with ethyl acetate (2×100 mL). The combined organic layers were washed with brine, dried over sodium sulfate and concentrated under reduced pressure. The residue was purified by column chromatography to afford a 67% yield (220 mg) of 101g as a white solid: mp 195-197° C.; $^1$H NMR (500 MHz, DMSO-$d_6$) δ 6.76 (s, 1H), 5.89 (s, 1H), 3.78 (t, 2H, J=6.5 Hz), 3.35 (m, 2H), 2.66 (m, 4H), 1.87 (m, 2H), 1.72 (m, 2H); (APCI+) m/z 191.3 (M+H)

Example 101h

2-Bromo-4-fluoro-6-(1-oxo-3,4,6,7,8,9-hexahydropyrido[3,4-b]-indolizin-2(1H)-yl)benzyl acetate 101h

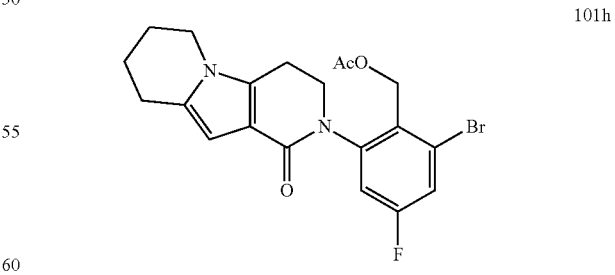

A 100-mL single-neck round-bottomed flask equipped with a magnetic stirrer and reflux condenser was charged with 1,4-dioxane (60 mL), 101c (1.9 g, 6.0 mmol), 101g (400 mg, 2.0 mmol), and cesium carbonate (1.3 g, 4.0 mmol). After bubbling nitrogen through the resulting mixture for 30 minutes, Xantphos (120 mg, 0.2 mmol) and tris(dibenzylideneacetone)dipalladium(0) (180 mg, 0.2 mmol) were added, and the reaction mixture was heated at 100° C. for 12 h. After this time the reaction was cooled to room temperature, partitioned between ethyl acetate (40 mL) and water (40 mL), and filtered. The aqueous layer was separated and extracted with ethyl acetate (70 mL×3). The combined organic layer was washed with brine (30 mL) and dried over sodium sulfate. The drying agent was removed by filtration and the filtrate was concentrated under reduced pressure. The residue was purified on flash column eluting with 2:1 PE/EA to afford 101h (421 mg, 46%) as yellow solid. MS: [M+H]+ 435. 1H NMR (500 MHz, MeOD) δ 7.52-7.50 (m, 1H), 7.20-7.23 (m, 1H), 6.14 (s, 1H), 5.10-5.20 (m, 2H), 4.06-4.12 (m, 1H), 3.92-3.97 (m, 1H), 3.83-3.88 (m, 1H), 3.75-3.79 (m, 1H), 3.03-3.10 (m, 1H), 2.94-2.99 (m, 1H), 2.75-2.83 (m, 2H), 2.00-2.05 (m, 5H), 1.83-1.88 (m, 2H)

Example 101i (S)-4-Fluoro-2-(1-methyl-5-(5-(2-methyl-4-(oxetan-3-yl)piperazin-1-yl)pyridin-2-ylamino)-6-oxo-1,6-dihydropyridin-3-yl)-6-(1-oxo-3,4,6,7,8,9-hexahydropyrido[3,4-b]indolizin-2(1H)-yl)benzyl acetate 101i

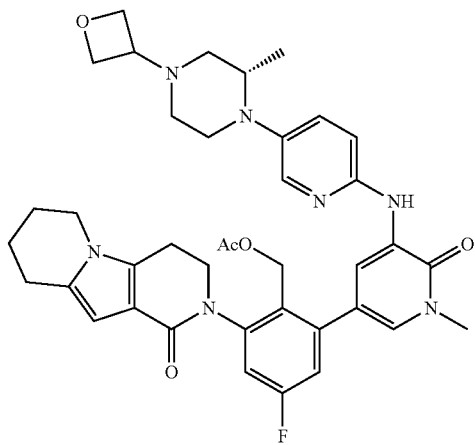

A mixture of 101h (300 mg, 0.70 mmol), (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one (332 mg, 0.70 mmol), CH3COONa (114 mg, 1.4 mmol), K3PO4 (368 mg, 1.4 mmol), PdCl2(dppf) (56 mg, 0.07 mmol), CH3CN (25 mL), and H2O (1 mL) was heated at 100° C. for 3 hours. It was then evaporated and the residue was purified by silical-gel column eluting with methylene chloride/methanol (30:1) to afford 101i (293 mg, yield 41%) as a brown solid. MS: (M+H)+ 710.

Example 101

(S)-2-(5-Fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)-phenyl)-3,4,6,7,8,9-hexahydropyrido[3,4-b]indolizin-1(2H)-one 101

To a solution of 101i (270 mg, 0.38 mmol) in propan-2-ol (8 mL), tetrahydrofuran (8 mL), and water (1.5 mL) was added LiOH (914 mg, 38 mmol). The mixture was stirred at 30° C. for 2 h. It was evaporated and the residue was purified by reverse-phase prep-HPLC to give 101 (127 mg, yield 50%) as a white solid. MS: (M+H)+ 669. 1H NMR (500 MHz, DMSO) δ 8.58 (t, J=2.5, 1H), 8.40 (s, 1H), 7.85 (d, J=3.0, 1H), 7.35-7.38 (m, 2H), 7.22-7.25 (m, 2H), 7.13-7.16 (m, 1H), 6.01 (s, 1H), 4.76 (s, 1H), 4.57-4.54 (m, 2H), 4.47 (t, J=6.0, 1H), 4.42 (t, J=6.5, 1H), 4.29 (s, 2H), 3.98-4.04 (m, 1H), 3.89-3.94 (m, 1H), 3.78-3.83 (m, 2H), 3.67 (s, 1H), 3.58 (s, 3H), 3.37-3.42 (m, 1H), 3.00-3.10 (m, 2H), 2.90-2.95 (m, 2H), 2.71 (t, J=6.0, 2H), 2.52-2.55 (m, 1H), 2.28-2.35 (m, 2H), 2.18 (t, J=8.5, 1H), 1.89-1.94 (m, 2H), 1.72-1.78 (m, 2H), 0.93 (t, J=6.5, 3H)

Example 102a (S)-[4-fluoro-2-(1-methyl-5-(5-(2-methyl-4-(oxetan-3-yl)-piperazin-1-yl)pyridin-2-ylamino)-6-oxo-1,6-dihydropyridin-3-yl)-6-{6-oxo-8-thia-4,5-diazatricyclo[7.4.0.0^{2,7}]trideca-1(9),2(7),3-trien-5-yl}phenyl] methyl acetate 102a

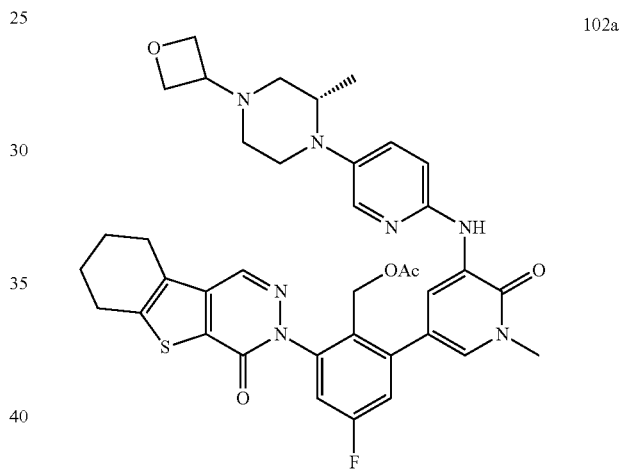

Following the procedures as described for 101i and starting with (4-fluoro-2-{6-oxo-8-thia-4,5-diazatricyclo[7.4.0.0^{2,7}]trideca-1(9),2(7),3-trine-5-yl}-6-(tetra-methyl-1,3,2-dioxaborolan-2-yl)phenyl)methyl acetate (250 mg) and 5-bromo-1-methyl-3-(3-methyl-5-(4-(oxetan-3-yl)piperazin-1-yl)pyridin-2-ylamino)pyridin-2(1H)-one (218 mg), afforded 102a as a yellow solid (225 mg, 62%). LCMS: [M+H]+ 726. See FIG. 2.

Example 102

(S)-5-[5-fluoro-2-(hydroxymethyl)-3(1-methyl-5-(5-(2-methyl-4-(oxetan-3-yl)piperazin-1-yl)pyridin-2-ylamino)-6-oxo-1,6-dihydropyridin-3-yl)phenyl]-8-thia-4,5-diazatricyclo[7.4.0.0^{2,7}]trideca-1(9),2(7),3-trien-6-one 102

Following the procedures as described for 101, hydrolysis of 102a (210 mg, 0.29 mmol) with lithium hydroxide afforded 102 as a white solid (117 mg, 85%). LCMS: [M+H]+ 684. 1H NMR (500 MHz, CDCl3) δ 8.61 (d, J=2.5, 1H), 8.26 (s 1H), 7.99 (d, J=2.5, 1H), 7.83 (s, 1H), 7.46 (d, J=2.0, 1H), 7.29-7.32 (m, 2H), 7.11 (dd, J=2.0, 8.0, 1H), 6.82 (d, J=9.0, 1H), 4.62-4.73 (m, 4H), 4.31 (d, J=6.5, 2H), 4.02 (t, J=6.5, 1H), 3.71 (s, 3H), 3.52-3.55 (m, 1H), 3.45-3.49 (m, 1H), 3.09 (t, J=4.5, 2H), 2.99 (t, J=4.5, 2H), 2.87 (t, J=4.5, 2H), 2.56 (dd, J=3.0, 11.0, 1H), 2.46-2.49 (m, 2H), 2.19-2.25 (m, 1H), 1.96-2.01 (m, 4H), 1.00 (d, J=6.0, 3H)

Example 103a (E)-Ethyl 3-(2-Chloro-4,4-dimethylcyclopent-1-enyl)acrylate 103a

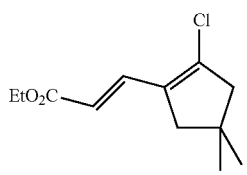

103a

The following two procedures were adapted from *Organic Preparations and Procedures Int.*, 29 (4), 471-498. A 500-mL single neck round bottomed flask equipped with a magnetic stirrer and nitrogen inlet was charged with 2-chloro-4,4-dimethylcyclopent-1-enecarbaldehyde (38 g, 240 mmol) in benzene (240 mL). See FIG. 3. To the solution was added ethoxycarbonylmethylene triphenylphosphorane (84 g, 240 mmol). The mixture was stirred for 14 h. After that time, the solvent was evaporated and the residue was triturated with hexanes (2 L) to extract the product away from the PPh₃ by-products. The organic layer was dried over sodium sulfate and concentrated in vacuo. The residue was purified by column chromatography using a 100% hexane—1:1 hexane/ethyl acetate gradient to afford a 37% yield (20 g) of 103a.

Example 103b

Ethyl 5,5-Dimethyl-1,4,5,6-tetrahydrocyclopenta[b]pyrrole-2-carboxylate 103b

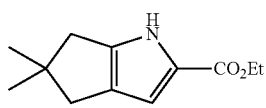

103b

A 250-mL single neck round bottomed flask equipped with a magnetic stirrer and nitrogen inlet was charged with 103a (17 g, 74 mmol) in DMSO (100 mL). To the solution was added sodium azide (9.6 g, 150 mmol). The mixture was then heated to 75° C. and stirred for 8 h. After cooling to rt, H₂O (100 mL) and CH₂Cl₂ (200 mL) were added and the organic layer was separated. The aqueous layer was extracted with CH₂Cl₂ (50 mL). The combined organic layers were washed with brine, dried over sodium sulfate and concentrated in vacuo. The residue was purified by column chromatography using a 100% hexane—1:1 hexane/ethyl acetate gradient to afford a 37% yield (5.7 g) of 103b.

Example 103c

Ethyl 1-(Cyanomethyl)-5,5-dimethyl-1,4,5,6-tetrahydrocyclopenta[b]pyrrole-2-carboxylate 103c

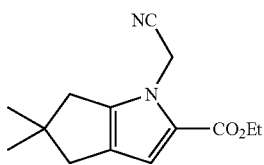

103c

A 250-mL single neck round bottomed flask equipped with a magnetic stirrer and nitrogen inlet was charged with 103b) (6.2 g, 30 mmol) in DMF (57 mL). To the solution was added NaH (80% dispersion in mineral oil, 1.26 g, 42.1 mmol). The resulting mixture was stirred at rt for 90 min. After that time, bromoacetonitrile (2.94 mL, 42 mmol) was added. The mixture was stirred for 14 h. After that time, water (100 mL) and ethyl acetate (200 mL) were added and the organic layer was separated. The aqueous layer was extracted with ethyl acetate (2×50 mL). The combined organic layers were washed with brine, dried over sodium sulfate and concentrated in vacuo. The residue was purified by column chromatography to afford a 95% yield (7 g) of 103c.

Example 103d

Ethyl 1-(2-Aminoethyl)-5,5-dimethyl-1,4,5,6-tetrahydrocyclopenta[b]pyrrole-2-carboxylate hydrochloride 103d

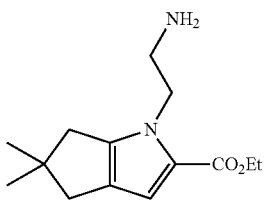

103d

A 500-mL Parr reactor bottle was purged with nitrogen and charged with 10% palladium on carbon (50% wet, 2.0 g dry weight), 103c (4.5 g, 18 mmol), 12% hydrochloric acid (9.2 mL, 37 mmol), ethyl acetate (80 mL) and ethanol (52 mL). The bottle was attached to a Parr hydrogenator, evacuated, charged with hydrogen gas to a pressure of 50 psi and shaken for 6 h. After this time, the hydrogen was evacuated, and nitrogen was charged into the bottle. Diatomaceous earth filtration agent (Celite® 521, 10.0 g) was added, and the mixture was filtered through a pad of Celite 521. The filter cake was washed with ethanol (2×50 mL), and the combined filtrates were concentrated to dryness under reduced pressure. The crude residue 103d was carried onto the next step without further purification.

Example 103e 4,4-Dimethyl-1,10-diazatricyclo[6.4.0.0$^{2,6}$]dodeca-2 (6),7-dien-9-one 103e

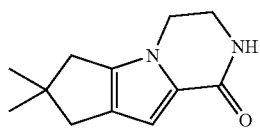

103e

A 100-mL single-neck round-bottomed flask equipped with a magnetic stirrer and nitrogen inlet was purged with nitrogen and charged with crude 103d (~18 mmol), sodium ethoxide (6.2 g, 92 mmol) and ethanol (120 mL). The mixture was stirred at 55° C. over night. After that time, the reaction mixture was concentrated under reduced pressure and the residue was partitioned between ethyl acetate (200 mL) and water (100 mL). The solution was filtered. The solid was washed with ethyl acetate (15 mL) to give 850 mg of desired product 103e. The organic layer was separated, and the aqueous layer was extracted with ethyl acetate (2×100 mL). The combined organic layers were dried over sodium sulfate and concentrated under reduced pressure to near dryness. The solution was filtered and the solid (1.44 g) was washed with ethyl acetate (15 mL). The combined solids were dried under vacuum a afford 61% yield (2.3 g) of 103e.

Example 103f

2-Bromo-4-fluoro-6-(9-oxo-4,4-dimethyl-1,10diazatricyclo[6.4.0.0$^{2,6}$]-dodeca-2(6),7-dien-10-yl)benzyl Acetate 103f

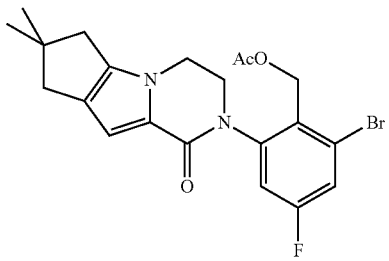

103f

A sealed tube was equipped with a magnetic stirrer and charged with 103e (740 mg, 3.6 mmol), 2,6-dibromo-4-fluorobenzyl acetate 101c (2.4 g, 7.2 mmol) and cesium carbonate (2.6 g, 7.9 mmol) in 1,4-dioxane (36 mL). After bubbling nitrogen through the solution for 30 min, Xantphos (250 mg, 0.43 mmol) and tris(dibenzylideneacetone) dipalladium(0) (260 mg, 0.29 mmol) were added, and the reaction mixture was heated to 100° C. for 16 h. After this time, H$_2$O (50 mL) and ethyl acetate (50 mL) were added. The aqueous layer was separated and extracted with ethyl acetate (2×50 mL). The combined organic extracts were washed with brine (100 mL) and dried over sodium sulfate. The resulting residue was purified by column chromatography eluting with a gradient of 100% hexanes-100% Ethyl acetate to afford a 56% yield (910 mg) of 103f.

Example 103g 2-(4,4,5,5-Tetramethyl-[1,3,2]dioxaborolan-2-yl)-4-fluoro-6-(9-oxo-4,4-dimethyl-1,10diazatricyclo [6.4.0.0$^{2,6}$]-dodeca-2(6),7-dien-10-yl)benzyl Acetate 103g Compound 103f (450 mg, 1.0 mmol), 4,4,4',4',5,5,5',5'-octamethyl-2,2'-bi(1,3,2-dioxaborolane) (635 mg, 2.5 mmol), potassium acetate (393 mg, 4.0 mmol), bis(diphenylphosphino)-ferrocene]dichloropalladium(II) complex with CH$_2$Cl$_2$ (Pd Cl$_2$dppf:CH$_2$Cl$_2$ (1:1), 66 mg, 0.08 mmol) and 1,4-dioxane (20 mL) were mixed and heated at 100° C. for 5 h. The reaction mixture was cooled to room temperature and filtered through a pad of Celite 521. The filter cake was washed with Ethyl Acetate (2×25 mL), and the combined filtrates were concentrated to dryness under reduced pressure to afford 103g (quantitative yield) as black oil, which was used directly for the next step. MS (ESI+) m/z 497.3 (M+H).

Example 103h (2S)-(2-{4,4-dimethyl-9-oxo-1,10-diazatricyclo-[6.4.0.0$^{2,6}$]dodeca-2(6),7-dien-10-yl}-4-fluoro-6-[1-methyl-5-({5-[2-methyl-4-(oxetan-3-yl)piperazin-1-yl]pyridin-2-yl}amino)-6-oxo-1,6-dihydropyridin-3-yl]phenyl)-methyl acetate 103h

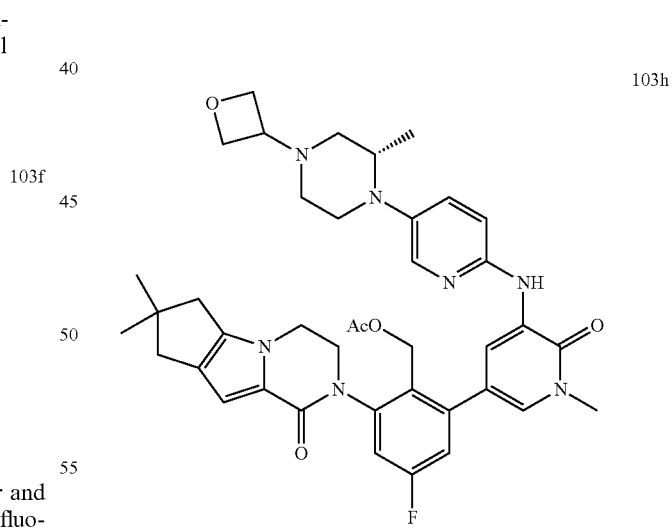

103h

Following the procedures as described for compound 101i, reaction of (2-{4,4-dimethyl-9-oxo-1,10-diazatricyclo [6.4.0.0$^{2,6}$]dodeca-2(6),7-dien-10-yl}-6-(4,4,5,5-tetramethyl-1,3,2-dioxaborolan-2-yl)phenyl)methyl acetate (229 mg, 0.46 mmol) and (S)-5-bromo-1-methyl-3-(5-(2-methyl-4-(oxetan-3-yl)piperazine-1-yl)pyridin-2-ylamino)pyridin-2 (1H)-one (200 mg, 0.46 mmol), afforded 103h as a yellow solid (80 mg, 24%). MS: [M+H]$^+$ 724.

Example 103

(2S)-10-[5-fluoro-2-(hydroxymethyl)-3-[1-methyl-5-({5-[2-methyl-4-(oxetan-3-yl)piperazin-1-yl]pyridine-2-yl}amino)-6-oxo-1,6-dihydropyridin-3-yl]-phenyl]-4,4-dimethyl-1,10-diazatricyclo[6.4.0.0$^{2,6}$]dodeca-2(6),7-dien-9-one 103

Following the procedures as described for 101, intermediate 103h (80 mg, 0.11 mmol) was hydrolyzed with lithium hydroxide to afford 103 as a yellow solid (40 mg, 53%). LCMS: [M+H]$^+$ 682. $^1$H NMR (500 MHz, CDCl$_3$) δ 8.56 (dd, J=2.0, 7.0, 1H), 7.95 (t, J=3.0, 1H), 7.82 (d, J=3.0, 1H), 7.47 (t, J=3.0, 1H), 7.31 (dd, J=3.0, 9.0, 1H), 7.17-7.14 (m, 1H), 6.95 (dd, J=2.5, 9.0, 1H), 6.82-6.80 (m, 2H), 4.71-4.61 (m, 4H), 4.56-4.53 (m, 1H), 4.41-4.37 (m, 1H), 4.33-4.28 (m, 1H), 4.23-4.15 (m, 3H), 3.91-3.86 (m, 1H), 3.70 (s, 3H), 3.55-3.44 (m, 2H), 3.08-3.06 (m, 2H), 2.56-2.46 (m, 7H), 2.21-2.16 (m, 1H), 1.27 (s, 6H), 0.98-0.97 (m, 3H)

Example 104a (2R,5S)-tert-Butyl2,5-dimethyl-4-(6-nitropyridin-3-yl)piperazine-1-carboxylate 104a

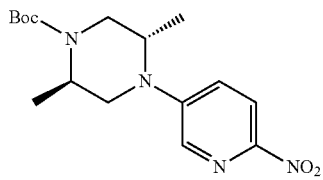

104a

Following the procedures as described for compound 108a, (2R,5S)-tert-butyl 4-chloro-2,5-dimethylpiperazine-1-carboxylate (1.5 g, 6.0 mmol) and 5-bromo-2-nitropyridine (1212 mg, 6.0 mol) were reacted to give 104a as a yellow solid (1500 mg, 75%). LCMS: [M+H]$^+$ 337. See FIG. 4.

Example 104b (2R,5S)-tert-Butyl 4-(6-Aminopyridin-3-yl)-2,5-dimethylpiperazine-1-carboxylate 104b

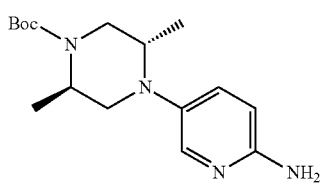

104b

Following the procedures as described for compound 108b, reaction of 104a 1.5 g 4.46 mmol) afforded 104b as a yellow solid (1130 mg, 83%). LCMS: [M+H]$^+$ 307

Example 104c (2R,5S)-tert-Butyl 4-(6-(5-Bromo-1-methyl-2-oxo-1,2-dihydropyridin-3-ylamino)pyridin-3-yl)-2,5-dimethylpiperazine-1-carboxylate 104c

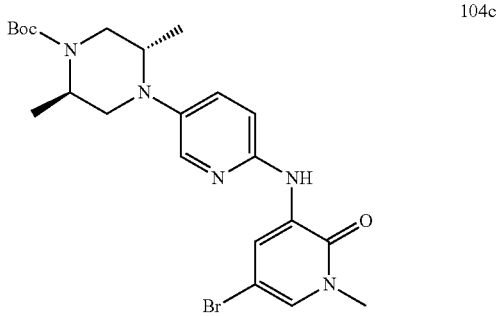

104c

Following the procedures as described for compound 108c, reaction of (2R,5S)-tert-butyl2,5-dimethylpiperazine-1-carboxylate (332 mg, 1.08 mmol) and 3,5-dibromo-1-methylpyridin-2(1H)-one (294 mg, 1.08 mmol afforded 104c as a yellow solid (402 mg, 75%). LCMS: [M+H]$^+$ 492

Example 104d (2R,5S)-tert-Butyl 4-(6-(5-Bromo-1-methyl-2-oxo-1,2-dihydropyridin-3-ylamino)pyridin-3-yl)-2,5-dimethylpiperazine-1-carboxylate 104d

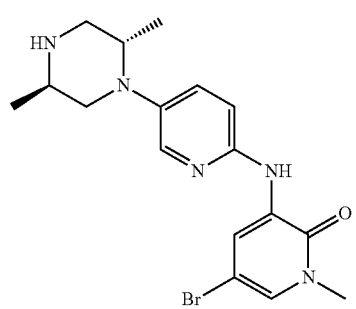

104d

Following the procedures as described for compound 108d, acidic hydrolysis of 104c (402 mg, 0.82 mmol) to remove the boc group afforded 104d as a yellow solid (300 mg, 94%). LCMS: [M+H]$^+$ 392

Example 104e

5-Bromo-3-(5-((2S,5R)-2,5-dimethyl-4-(oxetan-3-yl)piperazin-1-yl)-pyridin-2-ylamino)-1-methylpyridin-2(1H)-one 104e

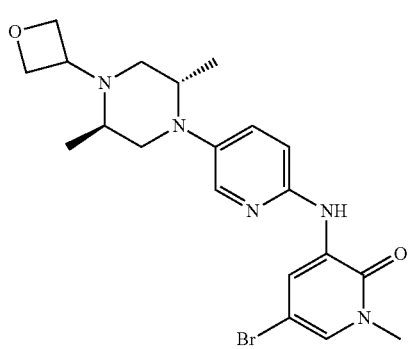

104e

Following the procedures as described for compound 108e and starting with 5-bromo-3-(5-((2S,5R)-2,5-dimethylpiperazin-1-yl)pyridin-2-ylamino)-1-methyl-pyridin-2(H)-one (300 mg, 0.77 mmol) afforded 104e as a yellow solid (320 mg, 93%). LCMS: [M+H]+ 448

Example 104f 2,2,2-Trichloro-1-(4,5,6,7-tetrahydro-1H-indol-2-yl)ethanone 104f

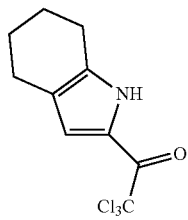

104f

A 100-mL single-neck round-bottomed flask equipped with a magnetic stirrer, condenser and nitrogen inlet was purged with nitrogen and charged with 4,5,6,7-tetrahydro-1H-indole (3.00 g, 24.8 mmol), trichloroacetyl chloride (13.5 g, 74.4 mmol) and 1,2-dichloroethane (50 mL). The solution was stirred at 85° C. for 2 h. After that time, the reaction mixture was concentrated under reduced pressure to afford a 100% yield (6.50 g) of 104f as a black semi-solid: ¹H NMR (500 MHz, DMSO-d₆) δ 11.94 (s, 1H), 7.05 (s, 1H), 2.62 (t, 2H, J=6.0 Hz), 2.47 (t, 2H, J=6.0 Hz), 1.80 (m, 2H), 1.65 (m, 2H); MS (ESI+) m/z 266.0 (M+H)

Example 104g

Ethyl 4,5,6,7-Tetrahydro-1H-indole-2-carboxylate 104g

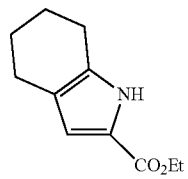

104g

A 100-mL single-neck round-bottomed flask equipped with a magnetic stirrer and nitrogen inlet was purged with nitrogen and charged with 2,2,2-trichloro-1-(4,5,6,7-tetrahydro-1H-indol-2-yl)ethanone 104f (6.50 g, 24.8 mmol), sodium ethoxide (17.0 mg, 0.25 mmol) and ethanol (40 mL). The solution was stirred at room temperature for 1 h. After that time, the reaction mixture was concentrated under reduced pressure. The residue was purified by column chromatography to afford a 100% yield (4.80 g) of ethyl 4,5,6,7-tetrahydro-1H-indole-2-carboxylate 104g as a brown solid: mp 70-72° C.; ¹H NMR (300 MHz, CDCl₃) δ 9.08 (s, 1H), 6.75 (s, 1H), 4.25 (q, 2H, J=7.2 Hz), 2.65 (t, 2H, J=6.0 Hz), 2.56 (t, 2H, J=6.0 Hz), 1.85 (m, 4H), 1.28 (t, 3H, J=7.2 Hz); MS (ESI+) m/z 194.1 (M+H)

Example 104h

Ethyl 1-(Cyanomethyl)-4,5,6,7-tetrahydro-1H-indole-2-carboxylate 104h

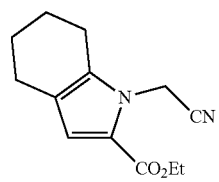

104h

A 125-mL single-neck round-bottomed flask equipped with a magnetic stirrer and nitrogen inlet was purged with nitrogen and charged with ethyl 4,5,6,7-tetrahydro-1H-indole-2-carboxylate 104g (5.76 g, 29.8 mmol) and DMF (50 mL). The solution was cooled to 0° C. using an ice bath. Sodium hydride, NaH (60% dispersion in mineral oil, 1.43 g, 35.8 mmol) was added. The resulting mixture was stirred at room temperature for 1 h. After that time, bromoacetonitrile (1.43 g, 35.8 mmol) was added. The mixture was stirred at room temperature for 14 h. After that time, the reaction mixture was concentrated under reduced pressure and the residue was partitioned between ethyl acetate (150 mL) and water (450 mL). The organic layer was separated, and the aqueous layer was extracted with ethyl acetate (3×150 mL). The combined organic layers were washed with brine, dried over sodium sulfate and concentrated under reduced pressure. The residue was purified by column chromatography to afford a 55% yield (3.80 g) of 104h as a yellow semi-solid: ¹H NMR (300 MHz, CDCl₃) δ 6.66 (s, 1H), 5.29 (s, 2H), 4.28 (q, 2H, J=7.2 Hz), 2.62 (t, 2H, J=6.3 Hz), 2.49 (t, 2H, J=6.3 Hz), 1.92 (m, 2H), 1.75 (m, 2H), 1.33 (t, 3H, J=7.2 Hz); MS (ESI+) m/z 233.1 (M+H)

Example 104i

Ethyl 1-(2-Aminoethyl)-4,5,6,7-tetrahydro-1H-indole-2-carboxylate 104i

104i

A 200-mL Parr reactor bottle was purged with nitrogen and charged with 10% palladium on carbon (50% wet, 1.28 g dry weight), 104h (3.00 g, 12.9 mmol), 12% hydrochloric acid (6.5 mL, 25 mmol), ethyl acetate (60 mL) and ethanol (40 mL). The bottle was attached to a Parr hydrogenator, evacuated, charged with hydrogen gas to a pressure of 50 psi and shaken for 6 h. After this time, the hydrogen was evacuated, and nitrogen was charged into the bottle. Celite 521 (4.0 g)

was added, and the mixture was filtered through a pad of Celite 521. The filter cake was washed with ethanol (2×20 mL), and the combined filtrates were concentrated to dryness under reduced pressure. The residue was partitioned between ethyl acetate (150 mL) and 10% aqueous potassium carbonate (100 mL). The organic layer was separated, and the aqueous layer was extracted with ethyl acetate (3×75 mL). The combined organic layers were dried over sodium sulfate and concentrated under reduced pressure. The residue was triturated with ethanol (5 mL) to afford a 71% yield (1.71 g) of 104i as a white solid: mp 102-104° C.; $^1$H NMR (500 MHz, DMSO-$d_6$) δ 6.61 (s, 1H), 6.22 (br, 2H), 4.15 (m, 4H), 2.77 (m, 2H), 2.59 (t, 2H, J=6.5 Hz), 2.42 (t, 2H, J=6.5 Hz), 1.70 (m, 2H), 1.62 (m, 2H), 1.23 (t, 3H, J=7.0 Hz); MS (APCI+) m/z 237.2 (M+H)

Example 104j 3,4,6,7,8,9-Hexahydropyrazino[1,2-a]indol-1(2H)-one 104j

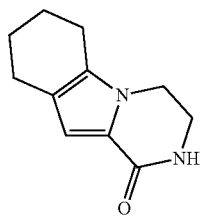

104j

A 100-mL single-neck round-bottomed flask equipped with a magnetic stirrer and nitrogen inlet was purged with nitrogen and charged with 104i (1.80 g, 7.63 mmol), sodium ethoxide (1.55 g, 22.8 mmol) and ethanol (50 mL). The mixture was stirred at 55° C. for 5 h. After that time, the reaction mixture was concentrated under reduced pressure and the residue was partitioned between ethyl acetate (200 mL) and water (100 mL). The organic layer was separated, and the aqueous layer was extracted with ethyl acetate (2×100 mL). The combined organic layers were washed with brine, dried over sodium sulfate and concentrated under reduced pressure. The residue was purified by column chromato-graphy to afford a 42% yield (605 mg) of 104j as a white solid: mp 207-209° C.; $^1$H NMR (500 MHz, DMSO-$d_6$) δ7.41 (s, 1H), 6.36 (s, 1H), 3.84 (t, 2H, J=6.0 Hz), 3.42 (m, 2H), 2.51 (t, 2H, J=6.0 Hz), 2.42 (t, 2H, J=6.0 Hz), 1.76 (m, 2H), 1.65 (m, 2H); (APCI+) m/z 191.3 (M+H)

Example 104k 2,6-Dibromo-4-fluorobenzaldehyde 104k

To a solution of 1,3-dibromo-5-fluoro-2-iodobenzene (50 g, 132 mmol) in anhydrous toluene (300 mL) cooled at −35° C. was added a solution of isopropyl-magnesium chloride (84 mL, 171 mmol, 2.0M in Et$_2$O) over 30 minutes while maintaining the internal temperature below −25° C. A clear brown solution was obtained and the stirring was continued for 1.5 h at −25° C. Then anhydrous DMF (34 mL, 436 mmol) was added over a period of 30 minutes. The reaction mixture was warmed to 10° C. (room temperature) over 1 h and stirred at this temperature for 1.5 h (hours). It was then quenched with 3.0M HCl and followed by the addition of ethyl acetate. The organic layer was separated and evaporated under reduced pressure. The residue was purified by silica-gel column chromatography eluting with petroleum ether/ethyl acetate (from 50:1 to 20:1) to give 104k as a white solid (20 g, 54%). $^1$H NMR (500 MHz, CDCl$_3$) δ 10.23 (s, 1H), 7.48 (d, J=7.5, 2H).

Example 104l (2,6-Dibromo-4-fluorophenyl)methanol 104l

To a solution of 104k (20 g, 71 mmol) in EtOH (500 mL) was added NaBH$_4$ (10 g, 284 mmol). The mixture was stirred at room temperature (10° C.) for 4 h and TLC showed the starting material had disappeared. The reaction was quenched by aqueous HCl solution (150 mL, 1M) and evaporated in vacuo until most of EtOH was distilled. The residue was extracted by ethyl acetate (500 mL×3). The organic layers were combined, dried with Na$_2$SO$_4$, and evaporated in vacuo. The residue was purified by silica-gel column chromatography eluting with petroleum ether/ethyl acetate (from 50:1 to 20:1) to give 104l as a white solid (15g, 75%). MS: [M-OH]$^+$ 267. $^1$H NMR (500 MHz, DMSO-$d_6$) δ 7.68 (d, J=8.5, 2H), 5.23 (s, 1H), 4.71 (s, 2H).

Example 104m 2,6-Dibromo-4-fluorobenzyl Acetate 104m

To a solution of (2,6-dibromo-4-fluorophenyl)methanol (104l) (20 g, 71 mmol) in CH$_2$Cl$_2$ (500 mL) at 0° C. was added pyridine (8.4 g, 107 mmol) and acetyl chloride (8.3 g, 107 mmol). The mixture was stirred at room temperature for 5 h. TLC showed the start material disappeared. The reaction was evaporated in vacuum and the residue was purified by silica-gel column chromatography eluting with petroleum ether/ethyl acetate (from 50:1 to 20:1) to give 104m as a white solid (20g, 87%). MS: [M-Oac]$^+$ 267. $^1$H NMR (500 MHz, CDCl$_3$) δ 7.36 (d, J=7.5, 2H), 5.38 (s, 2H), 2.10 (s, 3H)

Example 104n

2-Bromo-4-fluoro-6-(1-oxo-3,4,6,7,8,9-hexahydro-pyrazino[1,2-a]indol-2(1H)-yl)benzyl acetate 104n A 250-mL single-neck round-bottomed flask equipped with a magnetic stirrer was charged with 104j (3.8 g, 20 mmol), 104m (20 g, 60 mmol), XantPhos (1.2 g, 2 mmol), tris(dibenzylideneacetone)dipalladium(0) (1.8 g, 2 mmol), Cs$_2$CO$_3$ (16 g, 50 mmol), and 1,4-dioxane (120 mL). The system was evacuated and then refilled with N$_2$. A reflux condenser was attached to the flask, and the reaction mixture was heated at 100° C. for 16 h. Then, the mixture was cooled to room temperature and filtered. The filtrate was concentrated under reduced pressure and the resulting residue was purified by flash column chromatography eluting with 5:1 petroleum ether/ethyl acetate to afford 104n as a white solid (5.2 g, 60%). MS: [M+H]$^+$ 435. $^1$H NMR (500 MHz, DMSO-$d_6$) δ 7.70 (dd, J=3, 1H), 7.48 (dd, J=3, 1H), 6.52 (s, 1H), 5.01 (m, 2H), 4.18 (m, 2H), 4.02 (m, 1H), 3.73 (m, 1H), 2.60 (m, 2H), 2.45 (m, 2H), 1.98 (s, 3H), 1.77 (m, 2H), 1.68 (m, 2H).

Example 104o

4-Fluoro-2-(1-oxo-3,4,6,7,8,9-hexahydro-pyrazino [1,2-a]indol-2(1H)-yl)-6-(4,4,5,5-tetramethyl-1,3,2-dioxaborolan-2-yl)benzyl acetate 104o A 250-mL single-neck round-bottomed flask equipped with a magnetic stirrer was charged with 104n (3.8 g, 8.65 mmol), (PinB)₂ (11 g, 43.25 mmol), Pd(dppf)Cl₂ (0.4 g, 0.5 mmol), KOAc (2.5 g, 26 mmol), and 1,4-dioxane (150 mL). The system was evacuated and then refilled with N₂. A reflux condenser was attached to the flask and the reaction mixture was heated at 100° C. for 15 h. Then, the mixture was cooled to room temperature and filtered. The filtrate was concentrated under reduced pressure and the resulting residue was purified by flash column chromatography eluting with 5:1 petroleum ether/ethyl acetate to afford 104o as a yellow solid (3.2 g, 77%). MS: [M+H]⁺ 483.

Example 104p 2-(5-(5-(((2S,5R)-2,5-Dimethyl-4-(oxetan-3-yl)piperazin-1-yl)pyridin-2-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl Acetate 104p

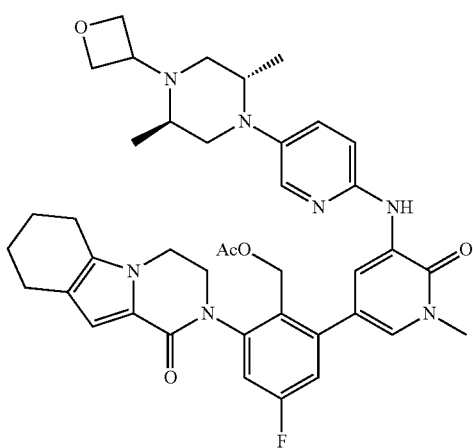

104p

Following the procedures as described for compound 108f, reaction of 104e (268 mg, 0.60 mmol) and 104o (289 mg, 0.60 mmol) afforded 104p as a yellow solid (300 mg, 85%). LCMS: [M+H]⁺ 724

Example 104

2-(3-(5-(5-(((2S,5R)-2,5-Dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 104

Following the procedures in Example 101i, hydrolysis of the acetate ester of 104p (288 mg, 0.40 mmol) with lithium hydroxide afforded 104 as a white solid (80 mg, 25%). LCMS: [M+H]⁺ 682. ¹H NMR (500 MHz, CDCl₃) δ 8.60 (d, J=2.0, 1H), 8.02 (d, J=2.5, 1H), 7.87 (d, J=1.5, 1H), 7.49-7.48 (m, 1H), 7.37 (d, J=9.0, 1H), 7.16 (d, J=9.0, 1H), 6.96 (d, J=8.5, 1H), 6.87 (s, 1H), 6.81 (d, J=9.0, 1H), 4.77-4.61 (m, 4H), 4.54 (d, J=11.5, 1H), 4.39-4.31 (m, 2H), 4.19-4.15 (m, 3H), 3.92-3.91 (m, 1H), 3.77-3.74 (m, 1H), 3.71 (s, 3H), 3.18 (s, 1H), 2.92-2.89 (m, 1H), 2.73-2.70 (m, 2H), 2.61-2.56 (m, 4H), 2.48 (s, 1H), 1.98-1.79 (m, 5H), 0.91-0.89 (m, 6H)

Example 105a (S)-2-(5-(5-(2-Ethyl-4-(oxetan-3-yl)piperazin-1-yl)pyridin-2-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl acetate 105a

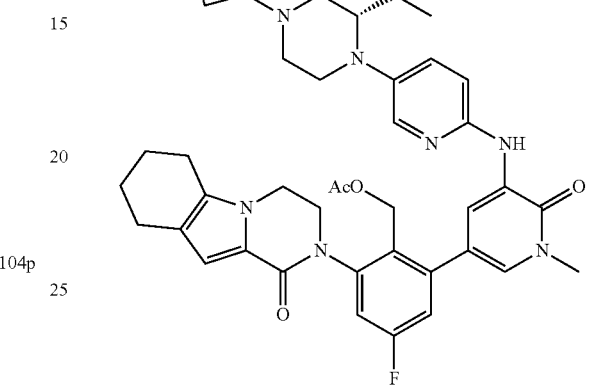

105a

A sealed tube equipped with a magnetic stirrer was charged with (S)-5-bromo-3-(5-(2-ethyl-4-(oxetan-3-yl)piperazin-1-yl)pyridin-2-ylamino)-1-methylpyridin-2(1H)-one (203 mg, 0.45 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate (216 mg, 0.45 mmol), Pd(dppf)Cl₂ (18 mg, 0.0225 mmol), NaOAc (74 mg, 0.90 mmol), K₃PO₄ (191 mg, 0.90 mmol), and acetonitrile (3 mL). See FIG. 5. After three cycles of vacuum/argon flush, the mixture was heated at 100° C. for 1 h. It was then filtered and the filtrate was evaporated in vacuo. The residue was purified by silica gel column chromatography eluting with dichloromethane/methanol (25:1, V/V) to afford 105a (220 mg, 87%) as a brown solid. LCMS: [M+H]⁺ 724

Example 105

(S)-2-(3-(5-(5-(2-Ethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 105

A mixture of 105a (220 mg, 0.30 mmol) and LiOH (72 mg, 3.0 mmol) in ⁱPrOH/THF (1:1, 4 mL) and H₂O (1 mL) was stirred at 30° C. for 1 h. The mixture was evaporated in vacuo and the residue was extracted with EtOAc (10 mL×2). The combined EtOAc extract was concentrated under reduced pressure and the residue was purified by reverse-phase prep-HPLC to afford 105 (54 mg, 25%) as a white solid. LCMS: [M+H]⁺ 682. ¹H NMR (500 MHz, CDCl₃) δ 8.54 (t, J=2.5, 1H), 7.91 (s, 1H), 7.80 (s, 1H), 7.47 (d, J=1.5, 1H), 7.26-7.24 (m, 1H), 7.18-7.15 (m, 1H), 6.95 (dd, J=2.5, 9.0, 1H), 6.87 (s, 1H), 6.81 (d, J=7.5, 1H), 4.72-4.61 (m, 4H), 4.54 (d, J=11.5, 1H), 4.33-4.30 (m, 2H), 4.20-4.14 (m, 3H), 3.92-3.90 (m, 1H), 3.71 (s, 3H), 3.53 (t, J=5.5, 1H), 3.31 (s, 1H), 3.12 (s, 2H), 2.61-2.56 (m, 5H), 2.44 (s, 2H), 2.35 (s, 1H), 1.91-1.89 (m, 2H), 1.80-1.79 (m, 2H), 1.67 (s, 1H), 1.43-1.37 (m, 1H), 0.82 (t, J=5.5, 3H)

Example 106a (S)-4-fluoro-2-(1-methyl-5-(5-(2-methyl-4-(oxetan-3-yl)piperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate 106a

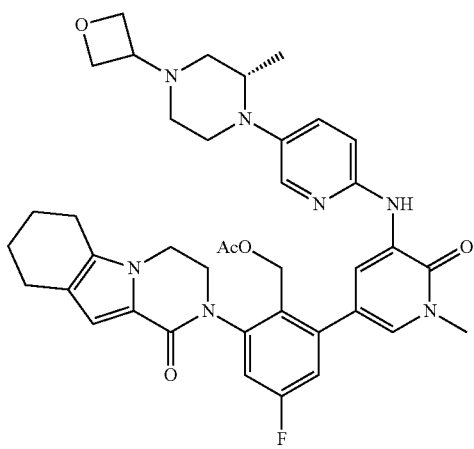

A sealed tube was charged with the mixture of 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate ((337 mg, 0.7 mmol), (S)-5-bromo-1-methyl-3-(3-methyl-5-(4-(oxetan-3-yl)piperazin-1-yl)pyridin-2-ylamino)pyridin-2(1H)-one (303 mg, 0.7 mmol), Pd(dppf)Cl$_2$ (33 mg, 0.04 mmol), K$_3$PO$_4$·3H$_2$O (372 mg, 1.4 mmol), and NaOAc (115 mg, 1.4 mmol) in CH$_3$CN (20 mL). See FIG. 6. The system was evacuated and refilled with N$_2$. The reaction mixture was heated at 110° C. for 2h. It was then cooled to room temperature and filtered. The filtrate was concentrated under reduced pressure and the resulting residue was purified by flash column chromatography eluting with 30:1 DCM/MeOH to afford 106a as a yellow solid (258 mg, 52%). LCMS: [M+H]$^+$ 710

Example 106

(S)-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one 106

At room temperature, to a solution of 106a (153 mg 0.22 mmol) in THF/iPA/H$_2$O (6 mL/6 mL/2 mL) was added LiOH (70 mg, 2.9 mmol) while stirring. This mixture was stirred for 0.5 h. Then, H$_2$O (20 mL) was added and the mixture was extracted with EA (30 mL×3). The combined organic layer was dried with Na$_2$SO$_4$ and concentrated to give a yellow solid, which was further purified by reverse-phase prep-HPLC to afford 106 as a white solid (60 mg, 42% yield). LCMS: [M+H]$^+$ 668. $^1$H NMR (500 MHz, CDCl3) δ 8.57 (dd, J=2.0, 7.0, 1H), 7.97 (s, 1H), 7.85 (s, 1H), 7.48 (t, J=2.5, 1H), 7.33 (d, J=7.0, 1H), 7.16 (d, J=8.0, 1H), 6.96 (dd, J=2.5, 9.0, 1H), 6.87 (s, 1H), 6.83 (d, J=9.0, 1H), 4.69-4.72 (m, 4H), 4.55 (d, J=11.5, 1H), 4.29-4.38 (m, 2H), 4.14-4.20 (m, 3H), 3.90-3.93 (m, 1H), 3.71 (s, 3H), 3.57 (s, 1H), 3.48 (s, 1H), 3.09-3.14 (m, 2H), 2.52-2.61 (m, 7H), 2.23 (s, 1H), 1.88-1.91 (m, 2H), 1.79-1.81 (m, 2H), 0.99 (d, J=5.0, 3H)

Example 107a (S)-tert-Butyl 2-Methyl-4-(6-nitropyridin-3-yl)piperazine-1-carboxylate 107a

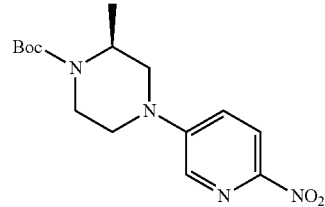

Following the procedures as described for compound 108a, reaction of 5-bromo-2-nitropyridine (1.5 g) and (S)-tert-butyl 2-methylpiperazine-1-carboxylate (2.3 g), gave 107a as a yellow solid (1.5 g, 40%). MS: [M+H]$^+$ 323. See FIG. 7.

Example 107b (S)-tert-Butyl 4-(6-Aminopyridin-3-yl)-2-methyl-piperazine-1-carboxylate 107b

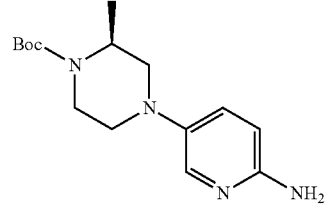

Following the procedures as described for compound 108b, reduction of 107a (4.0 g) gave 107b as a yellow solid (1.23 g, 97%). MS: [M+H]$^+$ 293

Example 107c (S)-tert-Butyl 4-(6-(5-Bromo-1-methyl-2-oxo-1,2-dihydro-pyridin-3-ylamino)pyridin-3-yl)-2-methylpiperazine-1-carboxylate 107c

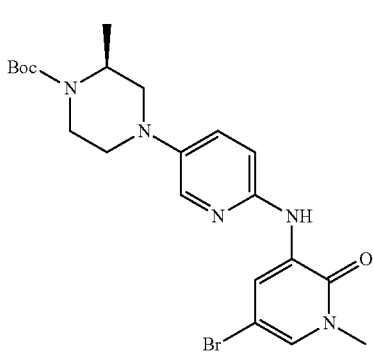

Following the procedures as described for compound 108c, reaction of 3,5-dibromo-1-methylpyridin-2(1H)-one (83 mg) and 107b (90 mg), gave 107c as a yellow solid (120 mg, 81%). MS: [M+H]$^+$ 480

Example 107d (S)-5-bromo-1-methyl-3-(5-(3-methylpiperazin-1-yl)-pyridin-2-yl-amino)pyridin-2(1H)-one 107d

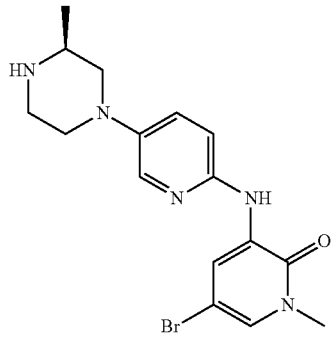

Following the procedures as described for compound 108d, acidic hydrolysis of the boc group of 107c (120 mg) gave 107d as a yellow solid (100 mg, 90%). MS: [M+H]+ 380

Example 107e (S)-5-bromo-3-(5-(3,4-dimethylpiperazin-1-yl)pyridin-2-ylamino)-1-methylpyridin-2(1H)-one 107e

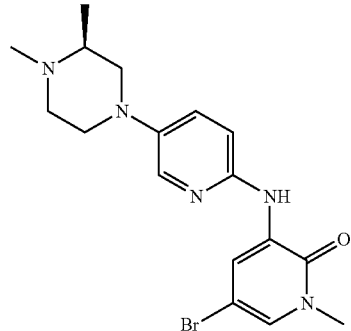

Following the procedures as described for compound 108e, methylation of 107d (100 mg) gave 107e as a yellow solid (60 mg, 59%). MS: [M+H]+ 394

Example 107f (S)-2-(5-(5-(3,4-dimethylpiperazin-1-yl)pyridin-2-ylamino)-1-methyl-6-oxo-1,6-dihydropyridin-3-yl)-4-fluoro-6-(1-oxo-3,4,6,7,8,9-hexahydropyrazino-[1,2-a]indol-2(1H)-yl)benzyl acetate 107f

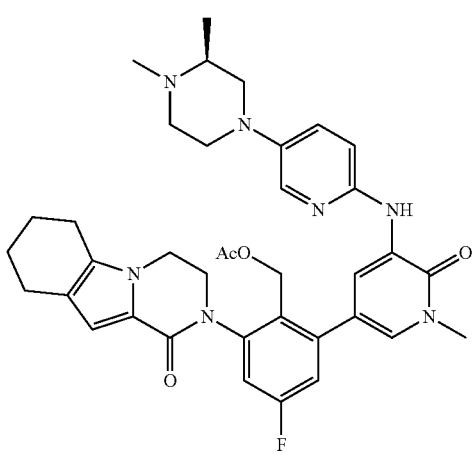

Following the procedures as described for compound 108f, reaction of 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate (74 mg) and 107e (60 mg) gave 107f as a yellow solid (60 mg, 59%). LCMS: [M+H]+ 668

Example 107

(S)-2-(3-(5-(5-(3,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 107

Following the procedures in Example 108, hydrolysis of 107f (60 mg) with lithium hydroxide gave 107 as a white solid (20 mg, 36%). LCMS: [M+H]+ 626. $^1$H NMR (500 MHz, CDCl3) δ: 8.55 (s, 1H), 7.90 (d, J=2.5, 1H), 7.77 (s, 1H), 7.46 (d, J=2.5, 1H), 7.26 (dd, J=3.0, 9.5, 1H), 7.17 (dd, J=3.0, 9.5, 1H), 6.95 (dd, J=3.0, 9.0, 1H), 6.87 (s, 1H), 6.81 (d, J=9.0, 1H), 4.55 (d, J=10.5, 1H), 4.31-4.36 (m, 2H), 4.14-4.20 (m, 3H), 3.90-3.92 (m, 1H), 3.70 (s, 3H), 3.38 (d, J=11, 1H), 3.32 (d, J=11.5, 1H), 2.94 (s, 2H), 2.56-2.61 (m, 5H), 2.49 (s, 1H), 2.38 (s, 4H), 1.89-1.91 (m, 2H), 1.79-1.80 (m, 2H), 1.17 (d, J=5.0, 3H)

Example 108a (R)-tert-Butyl 2-Methyl-4-(6-nitropyridin-3-yl) piperazine-1-carboxylate 108a A 100-mL single-neck round-bottomed flask equipped with a magnetic stirrer and a reflux condenser was charged with methylsulfinylmethane (50 mL), 5-bromo-2-nitropyridine (2.2 g, 11 mmol), (R)-tert-butyl 2-methylpiperazine-1-carboxylate (2.2 g, 11 mmol), and potassium carbonate (3.08 g, 22 mmol). See FIG. 8. The system was subjected to three cycles of vacuum/nitrogen flush and heated at 65° C. for 15 h. It was then cooled to room temperature, and partitioned between ethyl acetate (100 mL) and water (20 mL). The aqueous layer was separated and extracted with ethyl acetate (50 mL×2). The combined organic layer was washed with brine (50 mL) and dried over anhydrous sodium sulfate. The drying agent was removed by filtration and the filtrate was concentrated under reduced pressure. The residue was purified on flash column chromatography eluting with 2:1 (V/V) petroleum/ethyl acetate to afford 108a as a yellow solid (1.75 g, 50%). LCMS: [M+H]+ 323

Example 108b (R)-tert-Butyl 4-(6-aminopyridin-3-yl)-2-methylpiperazine-1-carboxylate 108b To a mixture of 108a (1.0 g, 3.1 mmol) in methanol (15 mL) was added 10% palladium carbon (100 mg). The mixture was stirred at room temperature under the atmosphere of hydrogen for overnight. At the end of reaction, it was filtered and the filtrate was concentrated under reduced pressure. The residue was purified by silica gel column chromatography eluting with DCM/MeOH (10:1, V/V) to afford 108b as a brown solid (800 mg, 88%). LCMS: [M+H]+ 293

Example 108c (R)-tert-Butyl 4-(6-(5-Bromo-1-methyl-2-oxo-1,2-dihydropyridin-3-ylamino) pyridine-3-yl)-2-methylpiperazine-1-carboxylate 108c A 50-mL single-neck round-bottomed flask equipped with a magnetic stirrer and a reflux condenser was charged with 1,4-dioxane (15 mL), 108b (800 mg, 2.7 mmol), 3,5-dibromo-1-methylpyridin-2(1H)-one (720 mg, 2.7 mmol), and cesium carbonate (1.76 g, 5.4 mmol). After bubbling nitrogen through the suspension for 3 minutes, Xantphos (78 mg, 0.14 mmol) and tris(dibenzylideneacetone)dipalladium(0) (128 mg, 0.14 mmol) were added. The system was subject to three cycles of vacuum/argon flash and heated at reflux for 3 h. It was then cooled to room temperature and filtered. The filtrate was partitioned between ethyl acetate (30 mL) and water (30 mL). The aqueous layer was separated and extracted with ethyl acetate (50 mL×2). The combined organic layer was washed with brine (50 mL) and dried over anhydrous sodium sulfate. The drying agent was removed by filtration and the filtrate was concentrated under reduced pressure. The residue was purified on flash column chromatography eluting with 10:1 dichloromethane/methanol to afford 108c as a yellow solid (624 mg, 47%). LCMS: [M+H]$^+$ 480

Example 108d (R)-5-bromo-1-methyl-3-(5-(3-methylpiperazin-1-yl)pyridin-2-ylamino)pyridine-2(1H)-one 108d To a mixture of 108c (624 mg, 1.3 mmol) in dichloromethane (8 mL) was added trifluoroacetic acid dropwise (300 mg, 2.6 mmol) at room temperature. Then the mixture was stirred for overnight. 2.0 N NaOH was added to adjust pH to greater than 10. Then the mixture was extracted with ethyl acetate (50 mL×2). The combined organic layer was washed with brine (50 mL), dried over anhydrous sodium sulfate, and concentrated under reduced pressure to afford 108d as a brown solid (300 mg, 61%). LCMS: [M+H]$^+$ 380

Example 108e (R)-5-Bromo-3-(5-(3,4-dimethylpiperazin-1-yl)pyridin-2-ylamino)-1-methyl pyridin-2(1H)-one 108e To a solution of 108d (300 mg, 0.8 mmol) in methanol (8 mL) was added two drops of acetic acid, 30% formaldehyde solution (0.5 mL), and sodium triacetoxyborohydride (354 mg, 1.6 mmol) at room temperature. Then the mixture was stirred at room temperature for 1 h. At the end of reaction, water (10 mL) was added and the mixture was extracted with ethyl acetate (20 mL×2). The combined organic layer was dried over anhydrous sodium sulfate and concentrated under reduced pressure to afford 108e as a brown solid (280 mg, 90%). LCMS: [M+H]$^+$ 392

Example 108f (R)-2-(5-(5-(3,4-Dimethylpiperazin-1-yl)pyridin-2-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl acetate 108f A sealed tube equipped with a magnetic stirrer was charged with 108e (280 mg, 0.71 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate (344 mg, 0.71 mmol), PdCl$_2$(dppf) (58 mg, 0.071 mmol), 1.0 M NaOAc (2.0 equiv), 1.0 M K$_3$PO$_4$ (2.0 equiv), and dioxane (5 mL). After three cycles of vacuum/argon flush, the mixture was heated at 110° C. for 2 h. It was then filtered and the filtrate was evaporated in vacuo. The residue was purified by silica gel column chromatography eluting with dichloromethane/methanol (10:1, V/V) to afford 108f (250 mg, 58%) as a white solid. LCMS: [M+H]$^+$ 668

Example 108

(R)-2-(3-(5-(5-(3,4-dimethylpiperazin-1-yl)pyridin-2-ylamino)-1-methyl-6-oxo-1,6-dihydropyridin-3-yl)-5-fluoro-2-(hydroxymethyl)-phenyl)-3,4,6,7,8,9-hexahydropyrazino[1,2-a]indol-1(2H)-one 108

A mixture of 108f (250 mg, 0.375 mmol) and LiOH.H$_2$O (98 mg, 2.0 mmol) in $^i$PrOH/THF (1:1, 3 mL) and H$_2$O (1 mL) was stirred at 30° C. for 2 h. The mixture was evaporated in vacuo and the residue was extracted with EtOAc (10 mL×2). The combined EtOAc extract was concentrated under reduced pressure and the residue was purified with reverse-phase prep-HPLC to afford 108 (62 mg, 26%) as a white solid. LCMS: [M+H]$^+$ 626. $^1$H NMR (500 MHz, CDCl$_3$) δ 8.53 (s, 1H), 7.89 (d, J=2.5, 1H), 7.76 (s, 1H), 7.45 (d, J=2, 1H), 7.26 (s, 1H), 7.14-7.16 (m, 1H), 6.92-6.94 (m, 1H), 6.86 (s, 1H), 6.79 (d, J=9, 1H), 4.52-4.54 (m, 1H), 4.30-4.32 (m, 2H), 4.14-1.16 (m, 3H), 3.90-3.91 (m, 1H), 3.69 (s, 3H), 3.34-3.35 (m, 2H), 2.91-2.92 (m, 2H), 2.60-2.38 (m, 10H), 1.83-1.85 (m, 2H), 1.78-1.79 (m, 2H), 1.17 (s, 3H)

Example 109a (R)-tert-Butyl 3-Methyl-4-(6-nitropyridin-3-yl)piperazine-1-carboxylate 109a

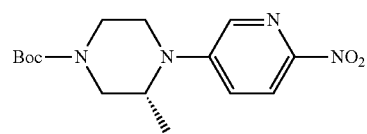

109a

A 100-mL single-neck round-bottomed flask equipped with a magnetic stirrer and reflux condenser was charged with 1,4-dioxane (60 mL), 5-bromo-2-nitropyridine (2.0 g, 10.0 mmol), (R)-tert-butyl 3-methylpiperazine-1-carboxylate (2.0 g, 10.0 mmol), and cesium carbonate (6.5 g, 20 mmol). See FIG. 9. After bubbling nitrogen through the resulting mixture for 30 minutes, XantPhos (579 mg, 1.0 mmol) and tris(dibenzylideneacetone)dipalladium(0) (915 mg, 1.0 mmol) were added, and the reaction mixture was heated at 100° C. for 15 h. After this time the reaction was cooled to room temperature and filtered. The filtrate was partitioned between ethyl acetate (100 mL) and water (100 mL). The aqueous layer was separated and extracted with ethyl acetate (150 mL×3). The combined organic layer was washed with brine (50 mL) and dried over sodium sulfate. The drying agent was removed by filtration and the filtrate was concentrated under reduced pressure. The residue was purified on flash column eluting with 30:1 DCM/MeOH to afford 109a (1.6 g, 44%) as a yellow solid. MS: [M+H]$^+$ 323. $^1$H NMR (500 MHz, DMSO) δ 8.21 (d, J=3.5, 1H), 8.18 (d, J=9.0, 1H), 7.43-7.45

(m, 1H), 4.33 (s, 1H), 3.92-3.99 (m, 1H), 3.80 (d, J=12.5, 2H), 3.06-3.23 (m, 3H), 1.43 (s, 9H), 1.09 (d, J=6.5, 3H).

Example 109b (R)-tert-Butyl 4-(6-Aminopyridin-3-yl)-3-methylpiperazine-1-carboxylate 109b

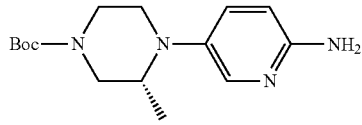

A 500-mL flask was purged with nitrogen and charged with 109a (1.5 g, 4.6 mmol), 10% palladium on carbon (50% wet, 200 mg), and methanol (70 mL). It was evacuated, charged with hydrogen gas, and stirred at room temperature for 10 h. The hydrogen was then evacuated and nitrogen was charged into the flask. The catalyst was removed by filtration through a pad of Celite and the filtrate was concentrated under reduced pressure to afford 109b (1.1 g, 81%) as a brown solid. MS: [M+H]$^+$ 293

Example 109c (R)-tert-Butyl 4-(6-(5-Bromo-1-methyl-2-oxo-1,2-dihydro-pyridin-3-ylamino)pyridin-3-yl)-3-methylpiperazine-1-carboxylate 109c

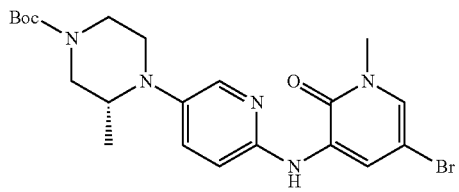

A 100-mL single-neck round-bottomed flask equipped with a magnetic stirrer and reflux condenser was charged with 1,4-dioxane (50 mL), 109b (1.0 g, 3.4 mmol), 3,5-dibromo-1-methylpyridin-2(1H)-one (2.7 g, 10.2 mmol), and cesium carbonate (2.2 g, 6.8 mmol). After bubbling nitrogen through the resulting mixture for 30 minutes, XantPhos (198 mg, 0.34 mmol) and tris(dibenzylideneacetone)-dipalladium(0) (313 mg, 0.34 mmol) were added, and the reaction mixture was heated at 100° C. for 5 h. After this time the reaction was cooled to room temperature and filtered. The filtrate was partitioned between ethyl acetate (100 mL) and water (100 mL). The aqueous layer was separated and extracted with ethyl acetate (100 mL×3). The combined organic layer was washed with brine (50 mL) and dried over sodium sulfate. The drying agent was removed by filtration and the filtrate was concentrated under reduced pressure. The residue was purified on flash column eluting with 30:1 DCM/MeOH to afford 109c as a yellow solid (1.1 g, 63%). MS: [M+H]$^+$ 478.

Example 109d (R)-5-Bromo-1-methyl-3-(5-(2-methylpiperazin-1-yl)pyridin-2-ylamino)pyridin-2(1H)-one 109d

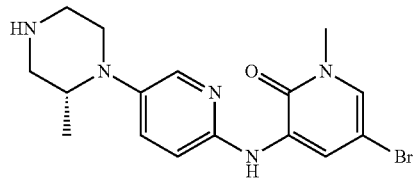

A mixture of 109c (600 mg, 1.26 mmol) in methanol (20 mL) was added HCl/dioxane (4.0 M, 4 mL). The reaction mixture was stirred at room temperature for 4 h. It was then concentrated at reduced pressure. The residue was basified with aqueous 1.0 M NaOH and extracted with DCM. The combined organic layer was washed with H$_2$O and concentrated under reduced pressure to afford 109d (450 mg, 95%) as yellow solid. MS: [M+H]$^+$ 378.

Example 109e (R)-5-Bromo-3-(5-(2,4-dimethylpiperazin-1-yl)pyridin-2-ylamino)-1-methylpyridin-2(1H)-one 109e

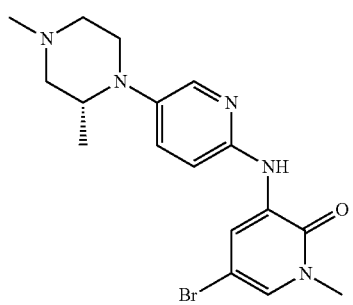

A mixture of 109d (500 mg, 1.3 mmol), and 30% formaldehyde (6.5 mmol) in methanol/HOAc (30 mL/3 mL) was stirred at room temperature for 5 minutes, followed by the addition of NaBH$_3$CN (120 mg, 1.9 mmol). The mixture was stirred at room temperature for 4 h. It was cooled to room temperature and H$_2$O (20 mL) was added. The mixture was extracted with DCM (50 mL) three times. The combined organic layer was concentrated under reduced pressure and the residue was purified by column chromatography eluting with 30:1 DCM/methanol to afford 109e as a yellow solid (473 mg, 83%). MS: [M+H]$^+$ 392.

Example 109f (R)-2-(5-(5-(2,4-Dimethylpiperazin-1-yl)pyridin-2-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl acetate 109f

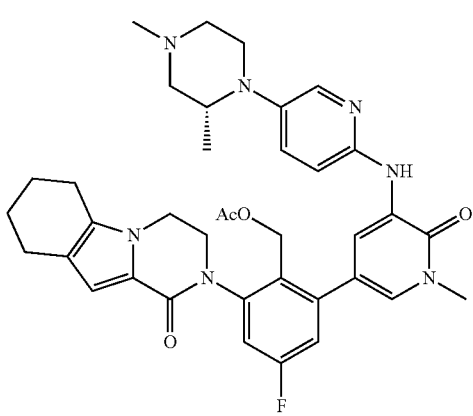

109f

A mixture of 109e (400 mg, 1.0 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate (490 mg, 1.0 mmol), PdCl$_2$(dppf) (80 mg, 0.1 mmol), 2.0 M Na$_2$CO$_3$ (2.0 equiv) in DMF (4 mL) was heated at 100° C. for 2 h. Brine was added and the mixture was extracted with EA (50 mL) three times. The combined organic layer was concentrated under reduced pressure. The residue was purified by flash column chromatography eluting with 30:1 DCM/MeOH to afford 109f as a brown solid (354 mg, 52%). LCMS: [M+H]$^+$ 668

Example 109

(R)-2-(3-(5-(5-(2,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 109

Following the procedures as described for compound 108, hydrolysis of 109f (337 mg, 0.5 mmol) with lithium hydroxide gave 109 as a yellow solid (152 mg, 48%). LCMS: (M+H)$^+$ 626. $^1$H NMR (500 MHz, DMSO) δ 8.57 (t, J=2.5, 1H), 8.39 (s, 1H), 7.83 (d, J=3.0, 1H), 7.31-7.36 (m, 3H), 7.23 (d, J=9.0, 1H), 7.17-7.20 (m, 1H), 6.53 (s, 1H), 4.86-4.88 (m, 1H), 4.32 (d, J=4.5, 2H), 4.09-4.20 (m, 3H), 3.87-3.91 (m, 1H), 3.66 (s, 1H), 3.59 (s, 3H), 3.04-3.08 (m, 1H), 2.90-2.94 (m, 1H), 2.57-2.65 (m, 3H), 2.47 (t, J=5.5, 2H), 2.35-2.42 (m, 2H), 2.19-2.21 (m, 1H), 2.18 (s, 3H), 1.79 (t, J=6.0, 2H), 1.66-1.69 (m, 2H), 0.91 (d, J=6.0, 3H)

Example 110a (S)-5-Bromo-3-(5-(2,4-dimethylpiperazin-1-yl)pyridin-2-ylamino)-1-methylpyridin-2(1H)-one 110a Following the procedures as described for compound 109e, (S)-5-bromo-1-methyl-3-(5-(2-methylpiperazin-1-yl)pyridin-2-ylamino)pyridin-2(1H)-one (377 mg, 1 mmol) was methylated by reductive formylation to give 110a as a white solid (294 mg, 75%). LCMS: [M+H]$^+$ 393. See FIG. 10.

Example 110b (S)-2-(5-(5-(2,4-dimethylpiperazin-1-yl)pyridin-2-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl acetate 110b Following the procedures as described for compound 109f, 110a (391 mg, 1 mmol) and 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate (482 mg, 1 mmol) were coupled by Suzuki reaction to give 110b as a white solid (334 mg, 50%). LCMS: [M+H]$^+$ 668

Example 110

(S)-2-(3-(5-(5-(2,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 110

Following the procedures in Example 109, hydrolysis of the acetate ester of 110b (667 mg, 1.0 mmol), gave 110 as a white solid (75 mg, 12%). LCMS: [M+H]$^+$ 626. $^1$H NMR (500 MHz, CDCl$_3$) δ 8.57 (d, J=8, 1H), 7.96 (s, 1H), 7.82 (s, 1H), 7.47 (d, J=1.5, 1H), 7.33 (s, 1H), 7.15-7.16 (m, 1H), 6.94-6.96 (m, 1H), 6.86 (s, 1H), 6.80 (d, J=8.5, 1H), 4.52-4.54 (m, 1H), 4.31-4.33 (m, 2H), 4.18-4.19 (m, 3H), 3.90-3.91 (m, 2H), 3.70 (s, 3H), 3.49-3.50 (m, 1H), 3.06-3.07 (m, 2H), 2.58-2.60 (m, 7H), 2.34 (s, 3H), 1.88-1.89 (m, 2H), 1.78-1.79 (m, 2H), 0.96 (s, 3H)

Example 111a 1-tert-Butyl 2-Methyl 4-benzylpiperazine-1,2-dicarboxylate 111a

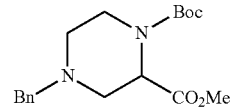

111a

To a dry 100 ml one necked round bottom flask equipped with a stirring bar was added 1-tert-butyl 2-methyl piperazine-1,2-dicarboxylate (5 g, 20.5 mmol) under N$_2$ (FIG. 1). Anhydrous acetonitrile (60 mL) was added followed by the additions of BnBr (2.7 mL, 22.5 mmol) and triethylamine (8.5 ml, 61.5 mmol). A condenser was then put on to the flask and the reaction mixture was heated at 71° C. for 45 minutes. The reaction mixture was allowed to come to room temperature and concentrated under reduced pressure. It was then diluted with dichloromethane and washed with water and brine. The organic layer was dried over Na$_2$SO$_4$, filtered and concentrated under reduced pressure. The crude compound was purified with flash column (PE:EA=8:1) to yield 4.5 g (66%) of 111a. MS: [M+H]+: 335

Example 111b (4-benzyl-1-methylpiperazin-2-yl)methanol 111b

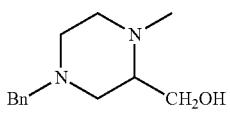

Compound 111a (1 g, 2.99 mmol) was dissolved in 100 mL of anhydrous tetrahydrofuran and lithium aluminum hydride (342 mg, 8.98 mmol) was added carefully at 0° C. and the mixture was stirred for 30 min. Then, it was refluxed for 3 h and the reaction mixture was poured onto ice portion-wise. It was then filtered and the filtrate was evaporated in vacuo. After addition of 100 mL brine, it was extracted with dichloromethane (100 mL×3). The combined organic layer was dried over $Na_2SO_4$, filtered and concentrated to afford 111b as yellow oil (0.6 g, yield 91%)

Example 111c 4-benzyl-2-(fluoromethyl)-1-methylpiperazine 111C

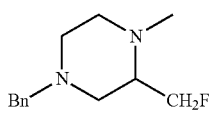

To an ice cooled solution of N,N'-dimethylaminosulfur trifluoride (10.8 ml, 81.8 mmol) in methylene chloride under $N_2$ was added 111b (9 g, 40.9 mmol) in methylene chloride dropwise. The yellow solution was stirred at 0° C. for 1 hour and warmed to room temperature and stirred for 15 hours. The reaction was diluted with $NaHCO_3$, and the organic layer was separated and dried over $Na_2SO_4$. The crude product was purified on silica gel (DCM:MeOH=50:1) to afford 111c as a yellow oil (3 g, yield 33%). MS: [M+H]+: 223

Example 111d 2-(Fluoromethyl)-1-methylpiperazine 111d

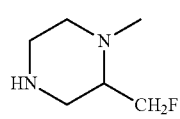

A 250-mL single-neck round-bottomed flask equipped with a magnetic stirrer was charged with 111c (3 g, 13.5 mmol) and MeOH (80 mL), and the resulting mixture was added Pd/C (10%) (300 mg). The reaction mixture was stirred under hydrogen gas ($H_2$) for 15 h. After the reaction was finished, it was filtered and concentrated to afford 111d as a yellow oil (1.6 g, yield 90%).

Example 111e 2-(Fluoromethyl)-1-methyl-4-(6-nitropyridin-3-yl)piperazine 111e

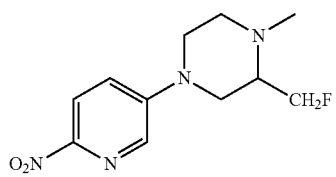

A 100-mL single-neck round-bottomed flask equipped with a magnetic stirrer and reflux condenser was charged with 111d (1.6 g, 12.1 mmol), 5-bromo-2-nitropyridine (3.7 g, 18.2 mmol) and cesium carbonate (9.9 g, 30.2 mmol). After bubbling nitrogen through the resulting solution for 30 min, xantphos (700 mg, 0.12 mmol) and tris(dibenzyl-ideneacetone)dipalladium(0) (550 mg, 0.06 mmol) were added, and the reaction mixture was heated at reflux for 15 h. After this time the reaction was cooled to room temperature, filtered and concentrated to afford a black solid as the crude product. Then it was purified on silica gel (DCM:MeOH=100:1) to afford 111e as a yellow solid (2.6 g, yield 76%). $^1$H NMR (500 MHz, MeOD) δ 8.20 (dd, J=12.5 Hz, 2H), 7.51 (dd, J=9.0 Hz, 1H), 4.74-4.54 (m, 2H), 4.03-3.92 (m, 2H), 3.20 (m, 1H), 3.09-2.99 (m, 2H), 2.50 (m, 2H), 2.46 (s, 3H),

Example 111f 5-(3-(Fluoromethyl)-4-methylpiperazin-1-yl)pyridin-2-amine 111f

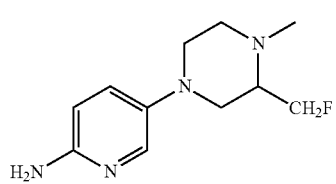

A 250-mL single-neck round-bottomed flask equipped with a magnetic stirrer was charged with 111e (2.6 g, 10.2 mmol) and MeOH (50 mL), and the resulting mixture was added Pd/C (10%) (260 mg). The reaction mixture was stirred under $H_2$ for 15 h. After the reaction was finished, it was filtered and concentrated to afford 111f, which was used in the next step without purification.

Example 111g

5-Bromo-3-(5-(3-(fluoromethyl)-4-methylpiperazin-1-yl)pyridin-2-ylamino)-1-methylpyridin-2(1H)-one 111g

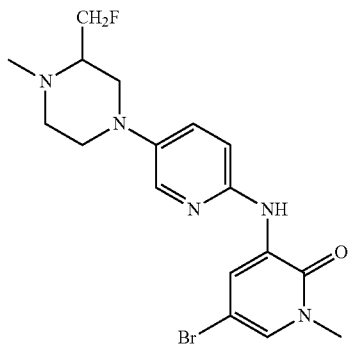

A 100-mL single-neck round-bottomed flask equipped with a magnetic stirrer and reflux condenser was charged with 1,4-dioxane (60 mL), 111e (crude, 14.1 mmol), 3,5-dibromo-1-methylpyridin-2(1H)-one (4.5 g, 16.9 mmol) and cesium carbonate (11.5 g, 35.2 mmol). After bubbling nitrogen through the resulting solution for 30 min, Xantphos (820 mg, 1.41 mmol) and tris(dibenzylideneacetone)dipalladium(0) (645 mg, 0.7 mmol) were added, and the reaction mixture was heated at reflux for 15 h. After this time the reaction was cooled to room temperature, filtered and concentrated to afford a black solid as the crude product. Then it was purified on silica gel (DCM:MeOH=100:1 to 50:1) to afford 111g as a yellow solid (3.1 g, yield 50%).

Example 111h

4-Fluoro-2-(5-(5-(3-(fluoromethyl)-4-methylpiperazin-1-yl)pyridin-2-ylamino)-1-methyl-6-oxo-1,6-dihydropyridin-3-yl)-6-(1-oxo-3,4,6,7,8,9-hexahydropyrazino[1,2-a]indol-2(1H)-yl)benzyl acetate 111h

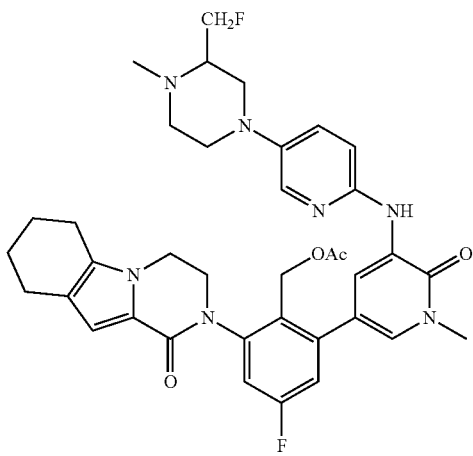

A mixture of 111g (1 g, 2.4 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate (1.3 g, 2.68 mmol), PdCl$_2$(dppf) (190 mg, 0.24 mmol), K$_3$PO$_4$ (1 g, 4.8 mmol), and NaOAc (390 mg, 4.8 mmol) in MeCN (15 mL) and H$_2$O (1.5 mL) was heated at 110° C. for 3 h. The solvent was evaporated in vacuo. The residue was purified on silica gel column (DCM:MeOH=50:1) to give 111h (0.8 g, yield 45%).

Example 111

2-(5-Fluoro-3-(5-(5-(3-(fluoromethyl)-4-methylpiperazin-1-yl)pyridin-2-ylamino)-1-methyl-6-oxo-1,6-dihydropyridin-3-yl)-2-(hydroxymethyl)phenyl)-3,4,6,7,8,9-hexahydropyrazino[1,2-a]indol-1(2H)-one 111

A mixture of 111h (750 mg, 1.09 mmol) and LiOH hydrate (2.3 g, 55 mmol) in iPrOH (10 mL), THF (10 mL) and H$_2$O (10 mL) was stirred at 30° C. for 1 h. The mixture was evaporated in vacuo, and the residue was extracted with DCM (3×30 mL). The combined extracts were concentrated under reduced pressure. And the residue was purified on silica gel column (DCM:MeOH=50:1) to give 111 as a yellow solid (700 mg, 93%). MS: [M+H]$^+$ 644. $^1$H NMR (500 MHz, MeOD) δ 8.54 (d, J=2.0 Hz, 1H), 7.93 (d, J=1.5 Hz, 1H), 7.41 (m, 1H), 7.33 (d, J=2.0 Hz, 1H), 7.21 (d, J=9.0 Hz, 2H), 7.02 (d, J=9.0 Hz, 1H), 6.72 (s, 1H), 4.67-4.46 (m, 4H), 4.19 (s, 3H), 4.02 (m, 1H), 3.70 (s, 3H), 3.51 (d, J=11.5 Hz, 1H), 3.42 (d, J=11. Hz, 1H), 3.36 (s, 1H), 2.96 (d, J=11.5 Hz, 1H), 2.85 (m, 1H), 2.73-2.50 (m, 7H), 2.48 (s, 3H), 1.88 (m, 2H), 1.78 (m, 2H)

Example 112a

N,N-Dibromobenzenesulfonamide 112a

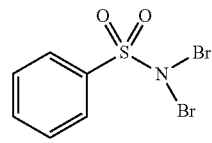

Figure 12:
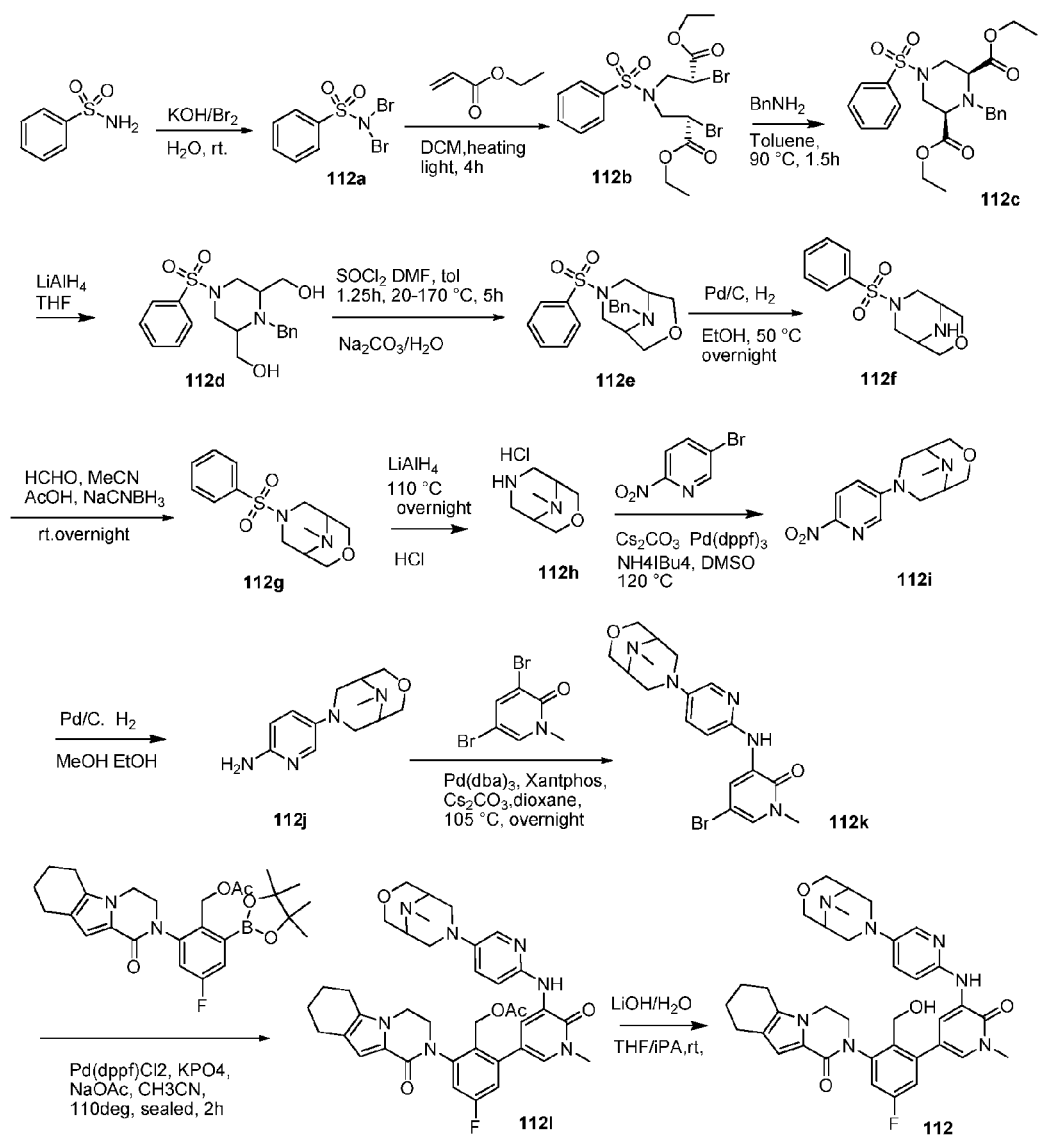

Benzensulfonamide (115g, 731.4 mmol), KOH (82.8g, 1.48 mol) and water (500 ml) were placed in a 1000-mL three-neck flask (FIG. 12). Then bromine (230 g, 1.48 mol) was added dropwise with vigorous stirring. The resulting precipitate was filtered, washed with water and filtered to give 112a as a yellow powder (207g, 90%)

Example 112b (S)-ethyl 2-bromo-3-(N—((R)-2-bromo-3-ethoxy-3-oxopropyl)phenyl-sulfonamido)propanoate 112b

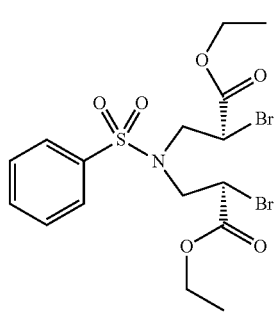

To a solution of 112a (207g, 658.26 mmol) in DCM (500 ml) was added ethyl acrylate (331.2g, 3.29 mol). The mixture was stirred to reflux and the mercury-arc lamp was opened to ensure the reaction taking place in the light of mercury-arc for 4h. Then the reaction mixture was purified through a silica gel column eluting with PE:EA=15:1 to 10:1 to give 112b as a white solid (20g, 6%). MS: [M+H]+: 538

Example 112c (2R,6S)-Diethyl 1-benzyl-4-(phenylsulfonyl)piperazine-2,6-dicarboxylate 112c

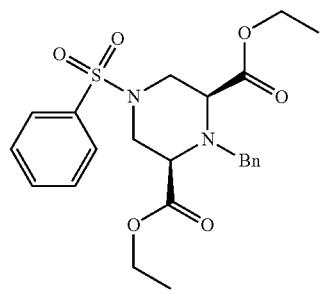

112c

To a solution of 112b (20g, 38.8 mmol) in toluene (100 ml) was added BnNH$_2$ (12.48g, 116.5 mmol). The reaction mixture was stirred at 90° C. for 3h. Then the mixture was purified through a silica gel column eluting with PE:EA=50:1 to 10:1 to give 112c as a white crystal (10.7g, 60%) MS: [M+H]+: 461

Example 112d (1-Benzyl-4-(phenylsulfonyl)piperazine-2,6-diyl)dimethanol 112d

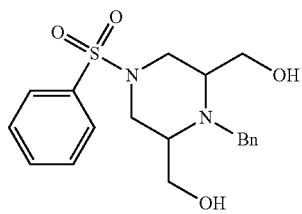

112d

1 M solution of LiAlH$_4$ in THF (70 ml; 70 mmol) was added dropwise under cooling and stirring to 112c (10.7 g; 23.2 mmol) in THF (275 ml). The reaction mixture was refluxed for 20 min, poured on a saturated solution of Na$_2$CO$_3$ and extracted with TBME three times. The combined organic phases were dried over Na$_2$SO$_4$ and evaporated to dryness to yield a colorless solid, which was washed with TBME to yield 112d as white crystals (7 g, 80%). MS: [M+H]+: 377

Example 112e

9-Benzyl-3-(phenylsulfonyl)-7-oxa-3,9-diaza-bicyclo[3.3.1]nonane 112e

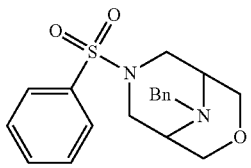

112e

SOCl$_2$ (1.34 ml; 18.5 mmol) in toluene (14 ml) was added under stirring at room temperature rapidly dropwised to a solution of 112e (7.0 g, 18.57 mmol) in DMF (276 ml). The reaction mixture was heated in an oil bath (170° C.) under reflux for 5h. The reaction mixture was evaporated, taken up in a saturated solution of Na$_2$CO$_3$ and extracted with EtOAc three times. The combined organic phases were dried over Na$_2$SO$_4$, filtered and evaporated to dryness and purified through a silica gel column eluting with PE: EA=10:1 to 5:1 to give 112e as a colorless crystal (3.0g, 45%) MS: [M+H]+: 413

Example 112f 3-(Phenylsulfonyl)-7-oxa-3,9-diaza-bicyclo[3.3.1]nonane 112f

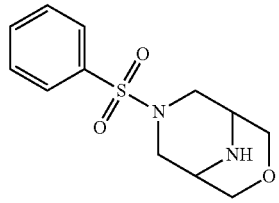

112f

To a solution of 112e (3.0g, 8.37 mmol) in EtOH (100 ml) was added Pd/C (0.5g) in MeOH (30 ml). The reaction mixture was hydrogenated at atmospheric hydrogen at 50° C. for overnight. Then, the catalyst was filtered off, washed with ethanol, and the solvent was evaporated to give 112f as a colorless solid (2.0g, 90%) MS: [M+H]+: 268

Example 112g

9-Methyl-3-(phenylsulfonyl)-7-oxa-3,9-diaza-bicyclo[3.3.1]nonane 112g

112g

To a solution of 112f (2.0g, 7.5 mmol) in MeCN (60 ml) was added HCHO (1.4 ml, 16 mmol) and 5 drops of AcOH at room temperature. Then NaCNBH₃ (1 g, 16 mmol) added and the mixture was stirred for 2h. It was poured onto water and extracted with EA (100*3). The organic layer was dried over Na₂SO₄, filtered off, evaporated, and purified through a silica gel column eluting with PE:EA=5:1 to 1:1 to give 112g as a colorless oil (1.5g, 72%) MS: [M+H]+: 283

Example 112h

9-Methyl-7-oxa-3,9-diaza-bicyclo[3.3.1]nonane Hydrochloride 112h

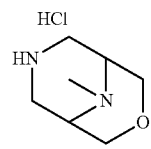

To a solution of 112g (1.5g, 5.3 mmol) in a mixture of toluene (15 ml) and THF (15 ml) was added LiAlH₄ (0.42g, 10.8 mmol). The reaction mixture was heated at 110° C. overnight. Then it was poured into HCl (2 mol). The organic layer was partitioned and the water layer was evaporated to dryness and dissolved in methanol. The resulting suspension was filtered and the filtrate was evaporated to give 112h (800 mg, 43%) as a colorless oil. MS: [M+H]+: 143

Example 112i

9-Methyl-3-(6-nitropyridin-3-yl)-7-oxa-3,9-diaza-bicyclo[3.3.1]nonane 112i

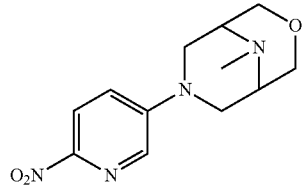

To a solution of 112h (800 mg, 5.6 mmol) and 5-bromo-2-nitropyridine (1.37g, 6.86 mmol) in DMSO (50 ml) was added Cs₂CO₃ (5g) and t-BuNH₄I (cat.). The reaction mixture was stirred at 120° C. overnight. Then it was cooled to room temperature, and extracted with EtOAc (300 ml). The organic layer was washed with water (3×100 ml) and brine (150 ml), dried over Na₂SO4, filtered and concentrated to get crude product, which was purified through a silica gel column eluting with DCM:MeOH=100:1 to 50:1 to give 112i as a yellow solid (850 mg, 72%) MS: [M+H]+: 265

Example 112j 5-(9-Methyl-7-oxa-3,9-diaza-bicyclo[3.3.1]nonan-3-yl)pyridin-2-amine 112j

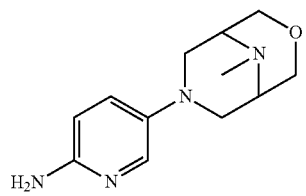

To a solution of 112i (800 mg, 3.0 mmol) in THF (80 ml) was added Pd/C (50 mg) in MeOH (20 ml) at room temperature. The reaction mixture was hydrogenated at atmospheric hydrogen pressure and stirred at room temperature overnight. The mixture was filtered and the filtrate was evaporated to give 112j as a colorless oil (680 mg, 90%). MS: [M+H]+: 235

Example 112k

5-Bromo-1-methyl-3-(5-(9-methyl-7-oxa-3,9-diaza-bicyclo[3.3.1]-nonan-3-yl)pyridin-2-ylamino)pyridin-2(1H)-one 112k

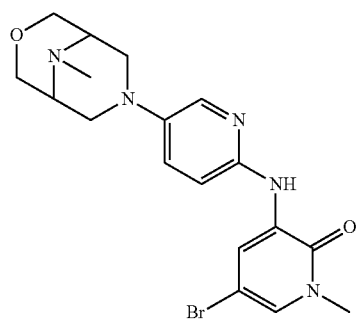

To a solution of 112j (500 mg, 2.1 mmol) and 3,5-dibromo-1-methylpyridin-2(1H)-one (852 mg, 3.2 mmol) in dioxane (100 ml) was added Xantphos (58 mg, 0.1 mmol), Cs₂CO₃ (2.1g, 6.4 mmol) and Pd₂(dba)₃ (110 mg, 0.1 mmol). The reaction mixture was stirred at 105° C. overnight. The mixture was cooled to RT, filtered, concentrated, and the crude product was purified through a silica gel column eluting with MeOH:DCM=0 to 1:5 to 112k (500 mg, 46.4%). MS: [M+H]+: 421

Example 112l

4-Fluoro-2-(1-methyl-5-(5-(9-methyl-7-oxa-3,9-diaza-bicyclo-[3.3.1]nonan-3-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl acetate 112l

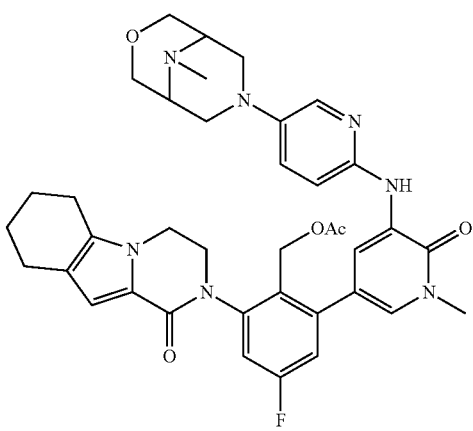

A mixture of 112l (500 mg, 1.2 mmol), 4-fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl acetate (636 mg, 1.32 mmol), PdCl$_2$(dppf) (95 mg, 0.12 mmol), K$_3$PO$_4$ (500 mg, 2.4 mmol), and NaOAc (195 mg, 2.4 mmol) in MeCN (8 mL) and H$_2$O (0.8 mL) was heated at 110° C. for 3 h. The solvent was evaporated in vacuo. The residue was purified on silica gel column eluting with DCM:MeOH=50:1 to give 112l (340 mg, yield 41%). MS: [M+H]+: 696

Example 112

2-(5Fluoro-2-(hydroxymethyl)-3-(1-methyl-5-(5-(9-methyl-7-oxa-3,9-diaza-bicyclo[3.3.1]nonan-3-yl)pyridin-2-ylamino)-6-oxo-1,6-dihydropyridin-3-yl)phenyl)-3,4,6,7,8,9-hexahydropyrazino[1,2-a]indol-1(2H)-one 112

A mixture of 112l (340 mg, 0.489 mmol) and LiOH hydrate (445 mg, 24.45 mmol) in iPrOH (4 mL), THF (4 mL) and H$_2$O (4 mL) was stirred at 30° C. for 1 h. The mixture was evaporated in vacuo, and the residue was purified on prep-HPLC to give 112 as a low yellow solid (105 mg, 32.85%). MS: [M+H]$^+$ 654. $^1$H NMR (500 MHz, CDCl$^3$) δ 8.46 (d, J=2.5 Hz, 1H), 7.87 (d, J=3.0 Hz, 1H), 7.69 (s, 1H), 7.42 (d, J=2.0 Hz, 1H), 7.23-7.14 (m, 2H), 6.94 (d, J=2.5 Hz, 1H), 6.84 (m, 2H), 4.52 (d, J=11.5 Hz, 1H), 4.31 (m, 2H), 4.12 (m, 5H), 3.89 (m, 3H), 3.69 (s, 3H), 3.43 (m, 4H), 2.84 (s, 2H), 5.62-2.54 (m, 7H), 1.88 (m, 2H), 1.78 (m, 2H)

Figure 13:
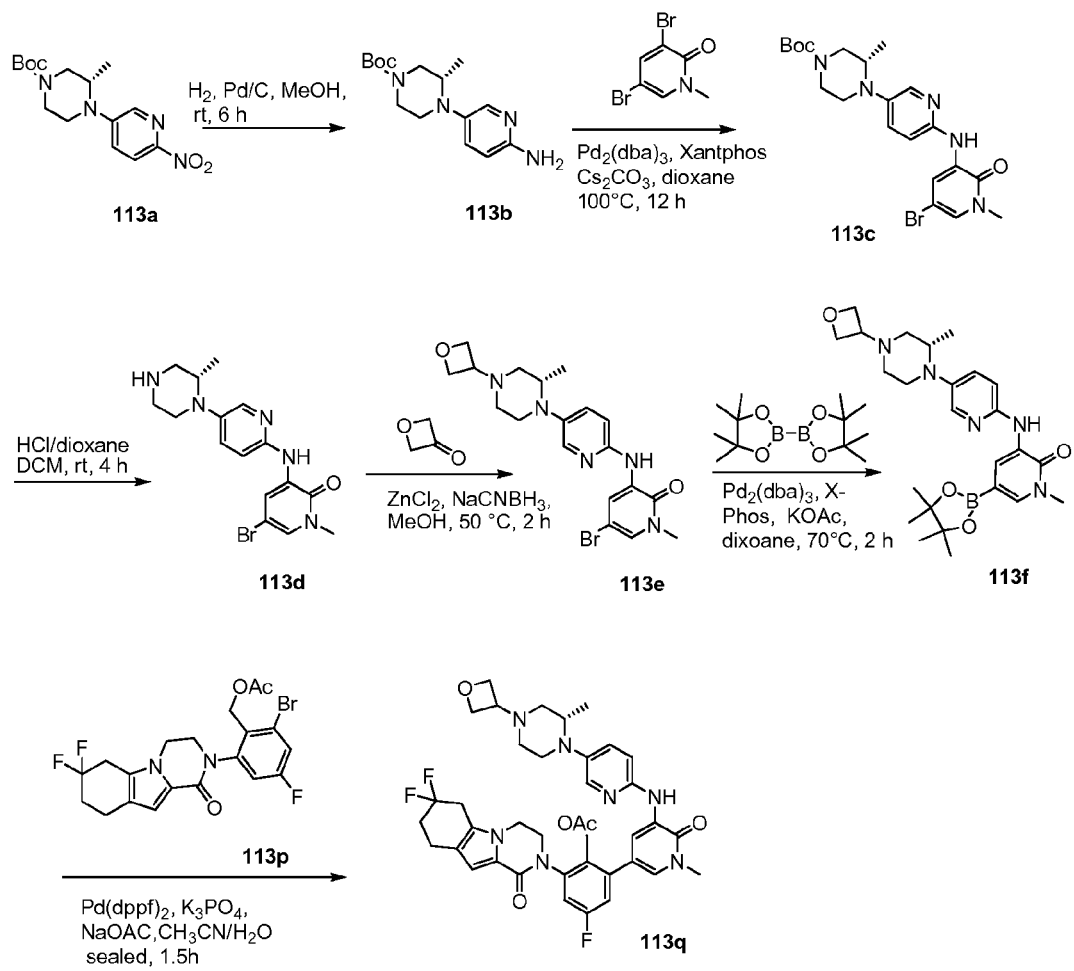

Example 113a (3S)-tert-Butyl 3-Methyl-4-(6-nitropyridin-3-yl)piperazine-1-carboxylate 113a The procedures described in Example 104 and starting with (3S)-tert-butyl 3-methylpiperazine-1-carboxylate (10.0 g, 50 mmol) and 5-bromo-2-nitropyridine (10.5 g, 50 mmol) afforded 113a as a yellow solid (8.05 g, 50%). See FIG. 13. MS-ESI: [M+H]$^+$ 323

Example 113b (3S)-tert-Butyl 4-(6-Aminopyridin-3-yl)-3-methylpiperazine-1-carboxylate 113b The procedures described in Example 104 and starting with 113a (5.8 g, 18 mmol) afforded 113b as a brown solid (4.9 g, 93%). See FIG. 13. MS-ESI: [M+H]$^+$ 293

Example 113c (3S)-tert-Butyl 4-(6-(5-Bromo-1-methyl-2-oxo-1,2-dihydropyridin-3-ylamino) pyridine-3-yl)-3-methylpiperazine-1-carboxylate 113c The procedures described in Example 104 and starting with 113b (4.0 g, 13.7 mmol) and 3,5-dibromo-1-methylpyridin-2(1H)-one (5.5 g, 20.6 mmol) afforded 113c as a yellow solid (5.4 g, 83%). See FIG. 13. MS-ESI: [M+H]$^+$ 478

Example 113d (3S)-5-Bromo-1-methyl-3-(5-(2-methylpiperazin-1-yl)pyridin-2-ylamino)pyridine-2(1H)-one 113d The procedures described in Example 104 and starting with 113c (3.1 g, 6.5 mmol) afforded 113d as a yellow solid (2.3 g, 94%). See FIG. 13. MS-ESI: [M+H]$^+$ 378.

Example 113e (S)-5-Bromo-1-methyl-3-(5-(2-methyl-4-(oxetan-3-yl)piperazin-1-yl)pyridin-2-ylamino)pyridin-2(1H)-one 113e A mixture of 113d (40.0 g, 106 mmol), oxetan-3-one (11.4 g, 159 mmol), NaBH$_3$CN (10.0 g, 159 mmol), and zinc chloride (21.3 g, 159 mmol) in methanol (700 mL) was stirred at 50° C. for 5 hours. The mixture was added to water (100 mL) and concentrated under reduced pressure. The residue was extracted with dichloromethane (3×200 mL). The combined organic layer was concentrated under reduced pressure and the residue was purified by silica-gel column chromatography eluting with 40:1 dichloromethane/methanol to afford 113e (35 g, 73%). See FIG. 13. MS: [M+H]$^+$ 434.

Example 113f (3S)-1-Methyl-3-(5-(2-methyl-4-(oxetan-3-yl)piperazin-1-yl)-pyridin-2-ylamino)-5-(4,4,5,5-tetramethyl-1,3,2-dioxaborolan-2-yl)pyridin-2(1H)-one 113f A 100-mL single-neck round-bottomed flask equipped with a magnetic stirrer and a reflux condenser was charged with 113e (1.0 g, 1.0 eq., 2.3 mmol), Pin$_2$B$_2$ (1.46 g, 2.50 eq., 5.75 mmol), Pd$_2$(dba)$_3$ (105 mg, 0.05 eq., 0.125 mmol), X-Phos (93 mg, 0.1 eq., 0.23 mmol), potassium acetate (676 mg, 3.0 eq., 6.9 mmol), and dioxane (50 mL). After three cycles of vacuum/argon flush, the mixture was heated at 90° C. for 4 h. It was then cooled to room temperature and filtered. The filtrate was concentrated under reduced pressure and the resulting residue was washed with 3:1 petroleum ether/ethyl acetate (80 mL) to afford 113f as a yellow solid (1.0 g, 90%). See FIG. 13. MS: [M+H]+ 482.

Example 113g

4-[5-(Ethoxycarbonyl)-1H-pyrrol-3-yl]-4-oxobutanoic Acid 113g

Figure 14:
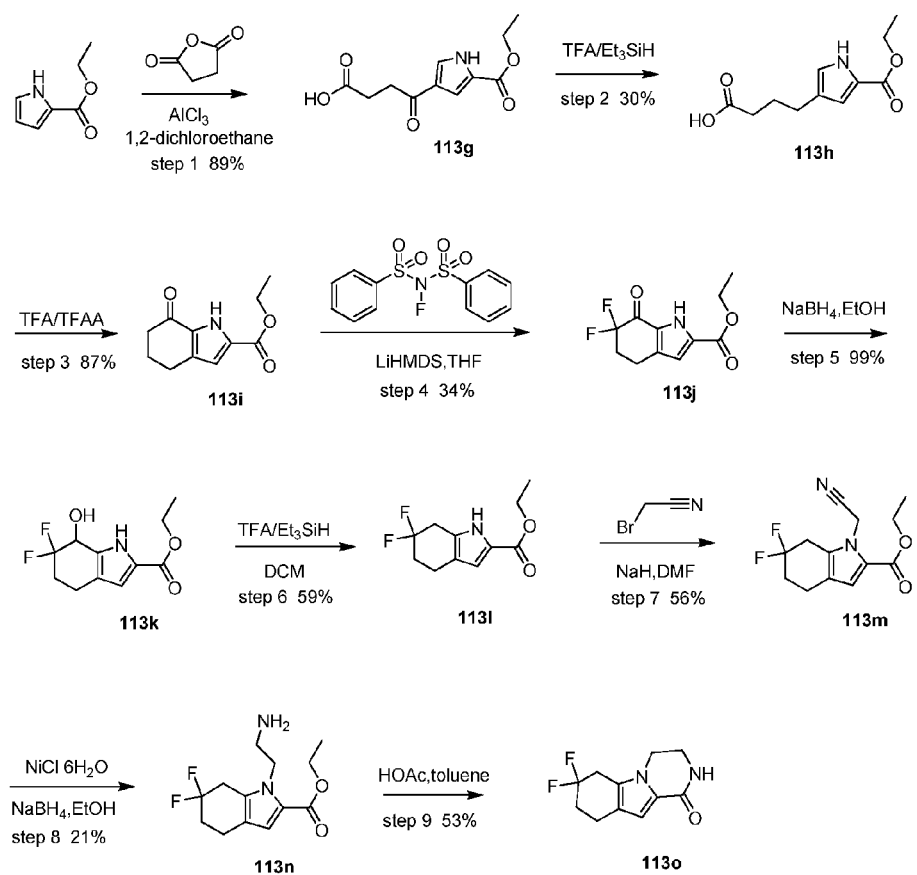
FIG. 14 shows the preparation of 113o from intermediate ethyl 1H-pyrrole-2-carboxylate.

Into a 3000-mL 4-necked round-bottom flask was placed a solution of oxolane-2,5-dione (100 g, 999.27 mmol, 2.00 equiv) in 1,2-dichloroethane (690 mL) and $AlCl_3$ (400.5 g, 3.00 mol, 6.00 equiv), followed by the addition of a solution of ethyl 1H-pyrrole-2-carboxylate (69 g, 495.86 mmol, 1.00 equiv) in 1,2-dichloroethane (660 mL) dropwise with stirring at room temperature over 20 min (FIG. 14). The resulting solution was stirred at room temperature for 3 h and quenched by the addition of 3 kg of water/ice. The solids were collected by filtration, washed with 1×1000 mL of water and dried in a vacuum oven to afford 105 g (89%) of 113g as a white solid.

Example 113h

4-[5-(Ethoxycarbonyl)-1H-pyrrol-3-yl]butanoic Acid 113h

Into a 2000-mL 4-necked round-bottom flask was placed a solution of 113g (105 g, 438.92 mmol, 1.00 equiv) in $CF_3COOH$ (1000 mL), followed by the addition of triethylsilane (204 g, 1.75 mol, 4.00 equiv) dropwise with stirring at room temperature over 30 min (FIG. 14). The resulting solution was stirred at room temperature for 8 h, concentrated under vacuum and diluted with 500 mL of water and 500 mL of ethyl acetate. The pH value of the solution was adjusted to 7 with saturated aqueous sodium bicarbonate. The resulting solution was extracted with 3×500 mL of ethyl acetate. The combined organic layers were dried over anhydrous sodium sulfate and concentrated under vacuum to afford 30 g (30%) of 113h as a light brown solid.

Example 113i

Ethyl 7-Oxo-4,5,6,7-tetrahydro-1H-indole-2-carboxylate 113i

Into a 1000-mL round-bottom flask was placed a solution of 113h (30 g, 133.19 mmol, 1.00 equiv) in $CF_3COOH$ (500 mL) and trifluoroacetyl 2,2,2-trifluoroacetate (42 g, 199.97 mmol, 1.50 equiv). See FIG. 14. The resulting solution was stirred at room temperature for 60 min, concentrated under vacuum, diluted with 500 mL of water and 500 mL of EA, and extracted with 3×500 mL of ethyl acetate. The combined organic layers were washed with 1×500 mL of saturated aqueous potassium carbonate and 1×500 mL of brine, dried over anhydrous sodium sulfate and concentrated under vacuum to afford 24 g (87%) of 113i as a light brown solid.

Example 113j

Ethyl 6,6-Difluoro-7-oxo-4,5,6,7-tetrahydro-1H-indole-2-carboxylate 113j

Into a 2000-mL 4-necked round-bottom flask purged and maintained with an inert atmosphere of nitrogen was placed a solution of 113i (24 g, 115.82 mmol, 1.00 equiv) in tetrahydrofuran (200 mL), followed by the addition of LiHMDS (406 mL, 3.50 equiv) dropwise with stirring at −78° C. over 30 min (FIG. 14). To this was added a solution of N-(benzenesulfonyl)-S-phenylfluoranesulfonamido (109.5 g, 347.24 mmol, 3.00 equiv) in tetrahydrofuran (500 mL) dropwise with stirring at −78° C. over 30 min. The resulting solution was stirred at room temperature overnight, quenched by the addition of 200 mL of saturated aqueous $NH_4Cl$ and extracted with 3×200 mL of ethyl acetate. The combined organic layers were dried over anhydrous sodium sulfate and concentrated under vacuum. The residue was purified on a silica gel column eluting with petroleum ether/ethyl acetate (30:1) to afford 9.5 g (34%) of 113j as a yellow solid.

Example 113k

Ethyl 6,6-Difluoro-7-hydroxy-4,5,6,7-tetrahydro-1H-indole-2-carboxylate 113k Into a 250-mL 3-necked round-bottom flask was placed a solution of 113j (18 g, 74.01 mmol, 1.00 equiv) in ethanol (100 mL), followed by the addition of $NaBH_4$ (2.8 g, 74.02 mmol, 1.00 equiv) in several batches at 0° C. (FIG. 14). The resulting solution was stirred at 5° C. for 10 min, quenched by the addition of 50 mL of saturated aqueous $NH_4Cl$, concentrated under vacuum and extracted with 3×50 mL of ethyl acetate. The combined organic layers were washed with 1×100 mL of water and 1×100 mL of brine, dried over anhydrous sodium sulfate and concentrated under vacuum to afford 18 g (99%) of 113k as a white solid.

Example 113l

Ethyl 6,6-Difluoro-4,5,6,7-tetrahydro-1H-indole-2-carboxylate 113l

Into a 500-mL 3-necked round-bottom flask was placed a solution of 113k (18 g, 73.40 mmol, 1.00 equiv) in dichloromethane (200 mL) and $CF_3COOH$ (41.9 g, 367.48 mmol, 5.00 equiv), followed by the addition of triethylsilane (25.6 g, 220.16 mmol, 3.00 equiv) dropwise with stirring at 0° C. over 20 min (FIG. 14). The resulting solution was stirred at room temperature for 4 h, adjusted pH to 7 with saturated aqueous sodium bicarbonate and extracted with 1×200 mL of dichloromethane. The combined organic layers were washed with 1×100 mL of water and 1×100 mL of brine, dried over anhydrous sodium sulfate and concentrated under vacuum. The crude product was purified by Flash-Prep-HPLC to afford 10 g (59%) of 113l as a white solid.

Example 113m

Ethyl 1-(Cyanomethyl)-6,6-difluoro-4,5,6,7-tetrahydro-1H-indole-2-carboxylate 113m Into a 250-mL 3-necked round-bottom flask was placed a solution of 113l (5.0 g, 21.81 mmol, 1.00 equiv) in N,N-dimethylformamide (50 mL), followed by the addition of sodium hydride (1.3 g, 54.17 mmol, 1.40 equiv, 60%) in several batches at 0° C. over 10 min. (FIG. 14). To this was added 2-bromoacetonitrile (3.7 g, 30.85 mmol, 1.40 equiv) dropwise with stirring at 20° C. over 10 min. The resulting solution was stirred at room temperature for 7 h, diluted with 100 mL of water and extracted with 3×50 mL of ethyl acetate. The combined organic layers were washed with 1×100 mL of water and 1×100 mL of brine, dried over anhydrous sodium sulfate and concentrated under vacuum. The residue was purified on a silica gel column eluting with ethyl acetate/petroleum ether (1:20) to afford 3.3 g (56%) of 113m as a light yellow oil.

Example 113n

Ethyl 1-(2-Aminoethyl)-6,6-difluoro-4,5,6,7-tetrahydro-1H-indole-2-carboxylate 113n Into a 100-mL round-bottom flask was placed a solution of 113m (3.3 g, 12.30 mmol, 1.00 equiv) in ethanol (30 mL) and NiCl$_2$.6H$_2$O (3.2 g, 13.45 mmol, 1.10 equiv), followed by the addition of NaBH$_4$ (1.4 g, 37.01 mmol, 3.00 equiv) in several batches at 0° C. (FIG. 14). The resulting solution was stirred at room temperature for 24 h. The solids were filtered out and the filtrate was concentrated under vacuum. The resulting solution was diluted with 30 mL of ethyl acetate and washed with 1×30 mL of hydrogen chloride (2 N). The solution was adjusted to pH=9 with saturated aqueous sodium bicarbonate and extracted with 2×30 mL of ethyl acetate. The combined organic layers were dried over anhydrous sodium sulfate and concentrated under vacuum to afford 0.7 g (21%) of 113n as a light yellow oil.

Example 113o 7,7-difluoro-1H,2H,3H,4H,6H,7H,8H,9H-pyrazino[1,2-a]indol-1-one 113o Into a 250-mL round-bottom flask was placed a solution of 113n (10 g, 36.73 mmol, 1.00 equiv) in toluene (100 mL) and acetic acid (1.1 g, 18.32 mmol, 0.50 equiv). See FIG. 14. The resulting solution was heated to reflux for 2 h, cooled and concentrated under vacuum. The residue was triturated in 100 mL of dry ether. The crude product was purified by recrystallization from ethanol to afford 4.43 g (53%) of 113o as a white solid. MS-ESI: [M+H]$^+$ 227. $^1$H NMR (300 MHz, DMSO) δ 2.10-2.24 (2H, m), 2.59-2.64 (2H, m), 3.17-3.27 (2H, m), 3.43-3.48 (2H, m), 3.88-3.92 (2H, m), 6.44 (1H, s), 7.56 (1H, s).

Example 113p

2-Bromo-6-(7,7-difluoro-1-oxo-3,4,6,7,8,9-hexahydropyrazino[1,2-a]indol-2(1H)-yl)-4-fluorobenzyl Acetate 113p A 100-mL round-bottomed flask equipped with a reflux condenser was charged with 1,4-dioxane (40 mL), 113o (890 mg, 3.94 mmol), 2,6-dibromo-4-fluorobenzyl acetate 101c (3847 mg, 11.8 mmol), Pd$_2$(dba)$_3$ (180 mg, 0.197 mmol), XantPhos (227 mg, 0.394 mmol), and cesium carbonate (2.57 g, 7.88 mmol). After three cycles of vacuum/argon flush, the mixture was heated at 100° C. for 16 h. It was then filtered and the filtrate was evaporated under reduced pressure. The residue was purified by silica-gel column chromatography eluting with 3:1 petroleum ether/ethyl acetate to afford 113p (1100 mg, 62%) as a white solid. MS-ESI: [M+H]$^+$ 471.1.

Example 113q (S)-2-(7,7-Difluoro-1-oxo-3,4,6,7,8,9-hexahydropyrazino[1,2-a]indol-2(1H)-yl)-4-fluoro-6-(1-methyl-5-(5-(2-methyl-4-(oxetan-3-yl)piperazin-1-yl)pyridin-2-ylamino)-6-oxo-1,6-dihydropyridin-3-yl)benzyl Acetate 113q A sealed tube was charged with 113p (47 mg, 0.10 mmol), 113f (47 mg, 0.10 mmol), Pd(dppf)Cl$_2$ (4 mg, 0.005 mmol), sodium acetate (16 mg, 0.2 mmol,), K$_3$PO$_4$ (43 mg, 0.2 mmol), acetonitrile (2 mL), and water (0.2 mL). After three cycles of vacuum/argon flush, the mixture was heated at 100° C. for 1 h. It was then filtered and the filtrate was evaporated under reduced pressure. The residue was purified by silica-gel column chromatography eluting with 25:1 dichloromethane/methanol to afford 113q (37 mg, 50%) as a brown solid. MS: [M+H]$^+$ 746.3

Example 113

(S)-7,7-difluoro-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one 113

A mixture of 113q (37 mg, 0.05 mmol) and lithium hydroxide (12 mg, 0.5 mmol) in i-propanol/THF (1:1, 4 mL) and water (1 mL) was stirred at 30° C. for 1 h. The mixture was evaporated under reduced pressure. Water (10 mL) was added to the residue and the resulting mixture was extracted with ethyl acetate (2×10 mL). The combined organic layer was concentrated under reduced pressure and the residue was purified by reverse-phase prep-HPLC to afford 113 (20 mg, 57%) as a white solid. MS: [M+H]$^+$ 704.3. $^1$H NMR (500 MHz, CDCl$_3$) δ 8.57-8.54 (m, 1H), 7.95 (d, J=3.0 Hz, 1H), 7.82 (d, J=3.5 Hz, 1H), 7.45-7.41 (m, 1H), 7.32 (d, J=8.5 Hz, 1H), 7.19-7.16 (m, 1H), 6.99-6.95 (m, 1H), 6.88 (d, J=6.5 Hz, 1H), 6.82 (d, J=8.5 Hz, 1H), 5.97 (d, J=11.5 Hz, 1H), 4.71-4.64 (m, 4H), 4.54 (d, J=12.0 Hz, 1H), 4.35-4.18 (m, 5H), 3.99-3.95 (m, 1H), 3.71 (s, 3H), 3.53 (t, J=6.0 Hz, 1H), 3.47-3.45 (m, 1H), 3.17 (t, J=12.0 Hz, 1H), 3.08 (t, J=5.0 Hz, 2H), 2.90 (t, J=8.5 Hz, 1H), 2.79 (t, J=6.0 Hz, 1H), 2.66-2.63 (m, 1H), 2.56 (d, J=11.0 Hz, 1H), 2.49-2.47 (m, 2H), 2.30-2.20 (m, 2H), 0.99 (d, J=6.0 Hz, 3H).

Example 114a (S)-tert-Butyl 3-Ethyl-4-(6-nitropyridin-3-yl)piperazine-1-carboxylate 114a

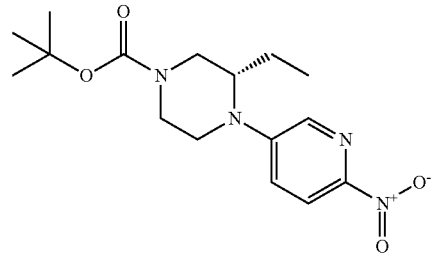 [SMILES: CC[C@H]1CN(C(=O)OC(C)(C)C)CCN1c1ccc([N+](=O)[O-])nc1]

A 250-mL single-neck round-bottomed flask equipped with a magnetic stirrer and a reflux condenser was charged with 1,4-dioxane (50 mL), 5-bromo-2-nitropyridine (2.02 g, 10 mmol), (S)-tert-butyl 3-ethylpiperazine-1-carboxylate (2.14 g, 10.0 mmol), Pd$_2$(dba)$_3$ (458 mg, 0.50 mmol), XantPhos (576 mg, 1.0 mmol), and cesium carbonate (6.52 g, 20 mmol). After three cycles of vacuum/argon flush, the mixture was heated at 100° C. overnight. After this time the reaction was cooled to room temperature. It was then filtered and the filtrate was evaporated under reduced pressure. The residue was purified by silica-gel column chromatography eluting with 3:1 petroleum ether/ethyl acetate to afford 114a (700 mg, 22%) as a yellow solid. MS: [M+H]$^+$ 336

Example 114b (S)-tert-Butyl 4-(6-Aminopyridin-3-yl)-3-ethylpiperazine-1-carboxylate 114b A 100-mL single-neck round-bottomed flask was purged with nitrogen and charged with 114a (0.7 g, 2.08 mmol), 10% palladium on carbon (50% wet, 208 mg), and methanol (40 mL). The mixture was evacuated, charged with hydrogen gas, and stirred at room temperature for 6 h. The hydrogen was then evacuated and nitrogen was charged into the flask. The catalyst was removed by filtration through a pad of Celite and the filtrate was concentrated under reduced pressure to afford 114b (568 mg, 89%). MS: [M+H]$^+$ 306

Example 114c (S)-tert-Butyl 4-(6-(5-Bromo-1-methyl-2-oxo-1,2-dihydropyridin-3-ylamino) pyridin-3-yl)-3-ethylpiperazine-1-carboxylate 114c A 100-mL single-neck round-bottomed flask equipped with a magnetic stirrer and a reflux condenser was charged with 1,4-dioxane (50 mL), 114b (568 mg, 1.86 mmol), 3,5-dibromo-1-methylpyridin-2(1H)-one (498 mg, 1.86 mmol), Pd$_2$(dba)$_3$ (85 mg, 0.093 mmol), XantPhos (107 mg, 0.186 mmol), and cesium carbonate (1.198 g, 3.72 mmol). After three cycles of vacuum/argon flush, the mixture was heated at 100° C. for 6 h. It was then filtered and the filtrate was evaporated under reduced pressure. The residue was purified by silica-gel column chromatography eluting with 100:1 dichloromethane/methanol to afford 114c (502 mg, 55%) as a yellow solid. MS: [M+H]$^+$ 492.

Example 114d (S)-5-Bromo-3-(5-(2-ethylpiperazin-1-yl)pyridin-2-ylamino)-1-methyl pyridin-2(1H)-one 114d A mixture of 114c (502 mg, 1.02 mmol), dichloromethane (2 mL), and 4.0 M HCl/dioxane (4 mL) was stirred at room temperature for 5 h. It was then concentrated under reduced pressure to afford crude 114d as a yellow solid (263 mg, 66%), which was used in the next step without further purification. MS: [M+H]$^+$ 392.

Example 114e (S)-5-Bromo-3-(5-(2-ethyl-4-(oxetan-3-yl)piperazin-1-yl)pyridin-2-ylamino)-1-methylpyridin-2(1H)-one 114e

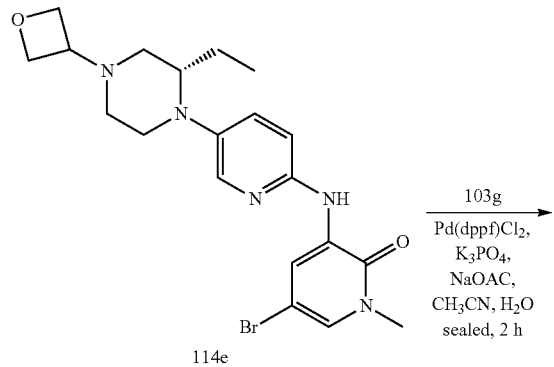

103g
Pd(dppf)Cl$_2$,
K$_3$PO$_4$,
NaOAC,
CH$_3$CN, H$_2$O
sealed, 2 h

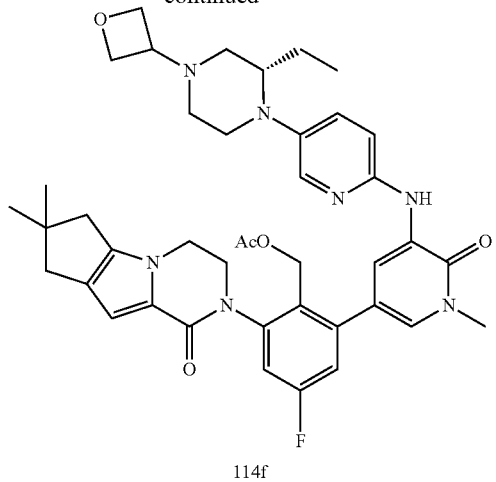

114f

A mixture of 114d (263 mg, 0.67 mmol), oxetan-3-one (96 mg, 1.34 mmol), NaBH$_3$CN 104 mg, 1.68 mmol), and zinc chloride (227 mg, 1.68 mmol) in methanol (10 mL) was stirred at 50° C. for 5 hours. water (10 mL) was then added to the reaction. The resulting mixture was concentrated under reduced pressure. The residue was extracted with dichloromethane three times. The combined organic layer was concentrated under reduced pressure and the residue was purified by silica-gel column chromatography eluting with 50:1 dichloromethane/methanol to afford 114e (203 mg, 68%). MS: [M+H]$^+$ 448.

Example 114f (S)-3-(5-(2-Ethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 114f A 100-mL single-neck round-bottomed flask equipped with a magnetic stirrer and a reflux condenser was charged with 114e (3219 mg, 7.20 mmol), Pin$_2$B$_2$ (9072 mg, 36.0 mmol), Pd$_2$(dba)$_3$ (329 mg, 0.36 mmol), X-phos (302 mg, 0.72 mmol), potassium acetate (2117 mg, 21.6 mmol), and dioxane (50 mL). After three cycles of vacuum/argon flush, the mixture was heated at 60° C. for 16 h. It was then cooled to room temperature and filtered. The filtrate was concentrated under reduced pressure and the resulting residue was washed with 8:1 petroleum ether/ethyl acetate (80 mL) to afford 114f as a yellow solid (3.0 g, 84%). MS: [M+H]$^+$ 496.4.

Example 114g (2-{4,4-Dimethyl-9-oxo-1,10-diazatricyclo[6.4.0.0$^{2,6}$]dodeca-2(6),7-dien-10-yl}-6-[5-({5-[(2S)-2-ethyl-4-(oxetan-3-yl)piperazin-1-yl]pyridin-2-yl}amino)-1-methyl-6-oxo-1,6-dihydropyridin-3-yl]-4-fluorophenyl)methyl Acetate 114g A 25-mL single-neck round-bottomed flask equipped with a magnetic stirrer and a reflux condenser was charged with 114f (180 mg, 0.40 mmol), (2-{4,4-dimethyl-9-oxo-1,10-diazatricyclo[6.4.0.0$^{2,6}$]dodeca-2(6),7-dien-10-yl}-4-fluoro-6-(4,4,5,5-tetramethyl-1,3,2-dioxaborolan-2-yl)phenyl)methyl acetate 103g (198 mg, 0.40 mmol), Pd(dppf)Cl$_2$ (29 mg, 0.04 mmol), K$_3$PO$_4$ (170 mg, 0.8 mmol), sodium acetate (66 mg, 0.8 mmol), acetonitrile (5 mL), and water (1.0 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with 30:1 dichloromethane/methanol to afford 114g as a yellow solid (115 mg, 39%). MS: [M+H]$^+$ 738.4

Example 114

2-(3-{5-[5-((S)-2-Ethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-7,7-dimethyl-3,4,7,8-tetrahydro-2H,6H-cyclopenta[4,5]pyrrolo[1,2-a]pyrazin-1-one 114

A mixture of 114g (115 mg, 0.16 mmol) and lithium hydroxide (38 mg, 1.6 mmol) in i-propanol/THF (1:1, 4 mL) and water (1 mL) was stirred at 30° C. for 1 h. The mixture was evaporated under reduced pressure and the residue was extracted with ethyl acetate (2×10 mL). The combined ethyl acetate extract was concentrated under reduced pressure and the residue was purified by reverse-phase prep-HPLC to afford 114 (45 mg, 40%) as a white solid. MS: [M+H]$^+$ 696.4. $^1$H NMR (500 MHz, CDCl$_3$) δ 8.55-8.54 (m, 1H), 7.91 (s, 1H), 7.80 (d, J=1.5 Hz, 1H), 7.47 (s, 1H), 7.26 (d, J=3.0 Hz, 1H), 7.17 (d, J=9.0 Hz, 1H), 6.95 (dd, J=2.5, 8.5 Hz, 1H), 6.83-6.81 (m, 2H), 4.71 (t, J=6.5 Hz, 2H), 4.67 (t, J=6.0 Hz, 1H), 4.62 (t, J=6.0 Hz, 1H), 4.57-4.55 (m, 1H), 4.41-4.38 (m, 1H), 4.32-4.30 (m, 1H), 4.24-4.14 (m, 3H), 3.92-3.87 (m, 1H), 3.71 (s, 3H), 3.56-3.50 (m, 1H), 3.33-3.29 (m, 1H), 3.13-3.11 (m, 2H), 2.58-2.56 (m, 3H), 2.52 (s, 2H), 2.44-2.43 (m, 2H), 2.38-2.32 (m, 1H), 1.66-1.64 (m, 1H), 1.42-1.37 (m, 1H), 1.28 (s, 6H), 0.82 (t, J=7.0 Hz, 3H).

Example 115a (R)-tert-Butyl 3-Methyl-4-(6-nitropyridin-3-yl)piperazine-1-carboxylate 115a

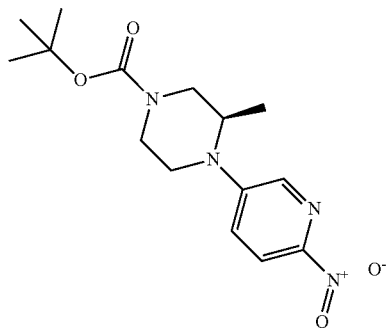

A 250-mL single-neck round-bottomed flask equipped with a magnetic stirrer and a reflux condenser was charged with 1,4-dioxane (60 mL), 5-bromo-2-nitropyridine (2.0 g, 10.0 mmol), (R)-tert-butyl 3-methylpiperazine-1-carboxylate (2.0 g, 10.0 mmol), and cesium carbonate (6.5 g, 20 mmol). After bubbling nitrogen through the resulting mixture for 10 minutes, tris(dibenzylideneacetone)dipalladium(0) (915 mg, 1.0 mmol) and XantPhos (579 mg, 1.0 mmol) were added. The system was subjected to three cycles of vacuum/argon flush and heated at 100° C. for 15 h. After this time the reaction was cooled to room temperature and filtered. The filtrate was partitioned between ethyl acetate (100 mL) and water (100 mL). The aqueous layer was separated and extracted with ethyl acetate (3×50 mL). The combined organic layer was washed with brine (100 mL) and dried over sodium sulfate. The drying agent was removed by filtration and the filtrate was concentrated under reduced pressure. The residue was purified by silica-gel column chromatography eluting with 30:1 dichloromethane/methanol to afford 115a (1.6 g, 44%) as a yellow solid. MS-ESI: [M+H]$^+$ 323. $^1$H NMR (500 MHz, DMSO-d$_6$) δ 8.21 (d, J=3.5 Hz, 1H), 8.18 (d, J=9.0 Hz, 1H), 7.45-7.43 (m, 1H), 4.34-4.33 (m, 1H), 3.92-3.99 (m, 1H), 3.80 (d, J=12.5 Hz, 2H), 3.06-3.23 (m, 3H), 1.43 (s, 9H), 1.09 (d, J=6.5 Hz, 3H).

Example 115b (R)-tert-Butyl 4-(6-Aminopyridin-3-yl)-3-methylpiperazine-1-carboxylate 115b A 250-mL flask was purged with nitrogen and charged with 115a (1.5 g, 4.6 mmol), 10% palladium on carbon (50% wet, 200 mg), and methanol (70 mL). It was evacuated, charged with hydrogen gas, and stirred at room temperature for 10 h. The hydrogen was then evacuated and nitrogen was charged into the flask. The catalyst was removed by filtration through a pad of Celite and the filtrate was concentrated under reduced pressure to afford 115b (1.1 g, 81%) as a brown solid. MS-ESI: [M+H]$^+$ 293

Example 115c (R)-tert-Butyl 4-(6-(5-Bromo-1-methyl-2-oxo-1,2-dihydropyridin-3-ylamino)pyridin-3-yl)-3-methylpiperazine-1-carboxylate 115c A 100-mL single-neck round-bottomed flask equipped with a magnetic stirrer and a reflux condenser was charged with 1,4-dioxane (40 mL), 115b (1.0 g, 3.4 mmol), 3,5-dibromo-1-methylpyridin-2(1H)-one (2.7 g, 10.2 mmol), and cesium carbonate (2.2 g, 6.8 mmol). After bubbling nitrogen through the resulting mixture for 10 minutes, XantPhos (198 mg, 0.34 mmol) and tris(dibenzylideneacetone)dipalladium (0) (313 mg, 0.34 mmol) were added. The reaction mixture was subjected to three cycles of vacuum/argon flush and heated at 100° C. for 5 h. After this time the reaction was cooled to room temperature and filtered. The filtrate was partitioned between ethyl acetate (50 mL) and water (50 mL). The aqueous layer was separated and extracted with ethyl acetate (3×30 mL). The combined organic layer was washed with brine (50 mL) and dried over sodium sulfate. The drying agent was removed by filtration and the filtrate was concentrated under reduced pressure. The residue was purified by silica-gel column chromatography eluting with 30:1 dichloromethane/methanol to afford 115c as a yellow solid (1.1 g, 63%). MS-ESI: [M+H]$^+$ 478.

Example 115d (R)-5-Bromo-1-methyl-3-(5-(2-methylpiperazin-1-yl)pyridin-2-ylamino)pyridin-2(1H)-one 115d To a mixture of 115c (600 mg, 1.26 mmol) in methanol (20 mL) was added HCl/dioxane (4M, 4 mL). The reaction mixture was stirred at room temperature for 4 h. It was then concentrated under reduced pressure. The residue was basified with aqueous 1M NaOH and extracted with dichloromethane (3×30 mL). The combined organic layer was washed with brine and concentrated under reduced pressure to afford 115d (450 mg, 95%) as a yellow solid. MS-ESI: [M+H]$^+$ 378.

Example 115e (R)-5-Bromo-3-(5-(2,4-dimethylpiperazin-1-yl)pyridin-2-ylamino)-1-methylpyridin-2(1H)-one 115e A mixture of 115d (500 mg, 1.3 mmol) and 30% formaldehyde (650 mg, 6.5 mmol) in methanol/acetic acid (30 mL/3 mL) was stirred at room temperature for 5 minutes, followed by the addition of $NaBH_3CN$ (120 mg, 1.9 mmol). The mixture was stirred at room temperature for 4 h. water (20 mL) was added and the resulting mixture was concentrated under reduced pressure. The residue was extracted with dichloromethane (3×30 mL). The combined organic layer was concentrated under reduced pressure and the residue was purified by silica-gel column chromatography eluting with 30:1 dichloromethane/methanol to afford 115e as a yellow solid (473 mg, 92%). MS-ESI: [M+H]+ 392.

Example 115f (R)-5-Bromo-1-methyl-3-(5-(2-methyl-4-(oxetan-3-yl)piperazin-1-yl)pyridin-2-ylamino)pyridin-2(1H)-one 115f A mixture of 115e (40.0 g, 106 mmol), oxetan-3-one (11.4 g, 159 mmol), $NaBH_3CN$ (10.0 g, 159 mmol), and zinc chloride (21.3 g, 159 mmol) in methanol (700 mL) was stirred at 50° C. for 5 hours. water (50 mL) was added to the mixture and concentrated under reduced pressure. The residue was extracted with dichloromethane (3×200 mL) and the combined organic layer was concentrated under reduced pressure. The residue was purified by silica-gel column chromatography eluting with 40:1 dichloromethane/methanol to afford 115f (35 g, 73%). MS: [M+H]+ 434.

Example 115g 2,2,2-Trichloro-1-(4,5,6,7-tetrahydro-1H-indol-2-yl)ethanone 115g A 100-mL single-neck round-bottomed flask equipped with a magnetic stirrer, condenser and nitrogen inlet was purged with nitrogen and charged with 4,5,6,7-tetrahydro-1H-indole (3.00 g, 24.8 mmol), trichloroacetyl chloride (13.5 g, 74.4 mmol) and 1,2-dichloroethane (50 mL). The solution was stirred at 85° C. for 2 h. After that time, the reaction mixture was concentrated under reduced pressure to afford a 100% yield (6.50 g) of 115g as a black semi-solid: $^1$H NMR (500 MHz, DMSO-$d_6$) δ 11.94 (s, 1H), 7.05 (s, 1H), 2.62 (t, 2H, J=6.0 Hz), 2.47 (t, 2H, J=6.0 Hz), 1.80 (m, 2H), 1.65 (m, 2H); MS (ESI+) m/z 266.0 (M+H)

Example 115h

Ethyl 4,5,6,7-Tetrahydro-1H-indole-2-carboxylate 115h

A 100-mL single-neck round-bottomed flask equipped with a magnetic stirrer and nitrogen inlet was purged with nitrogen and charged with 115g (6.50 g, 24.8 mmol), sodium ethoxide (17.0 mg, 0.25 mmol) and ethanol (40 mL). The solution was stirred at room temperature for 1 h. After that time, the reaction mixture was concentrated under reduced pressure. The residue was purified by column chromatography to afford a 100% yield (4.80 g) of 115h as a brown solid: mp 70-72° C.; $^1$H NMR (300 MHz, CDCl$_3$) δ 9.08 (s, 1H), 6.75 (s, 1H), 4.25 (q, 2H, J=7.2 Hz), 2.65 (t, 2H, J=6.0 Hz), 2.56 (t, 2H, J=6.0 Hz), 1.85 (m, 4H), 1.28 (t, 3H, J=7.2 Hz); MS (ESI+) m/z 194.1 (M+H)

Example 115i

Ethyl 1-(Cyanomethyl)-4,5,6,7-tetrahydro-1H-indole-2-carboxylate 115i

A 125-mL single-neck round-bottomed flask equipped with a magnetic stirrer and nitrogen inlet was purged with nitrogen and charged with 115h (5.76 g, 29.8 mmol) and DMF (50 mL). The solution was cooled to 0° C. using an ice bath. NaH (60% dispersion in mineral oil, 1.43 g, 35.8 mmol) was added. The resulting mixture was stirred at room temperature for 1 h. After that time, bromoacetonitrile (1.43 g, 35.8 mmol) was added. The mixture was stirred at room temperature for 14 h. After that time, the reaction mixture was concentrated under reduced pressure and the residue was partitioned between ethyl acetate (150 mL) and water (450 mL). The organic layer was separated, and the aqueous layer was extracted with ethyl acetate (3×150 mL). The combined organic layers were washed with brine, dried over sodium sulfate and concentrated under reduced pressure. The residue was purified by column chromatography to afford a 55% yield (3.80 g) of 115i as a yellow semi-solid: $^1$H NMR (300 MHz, CDCl$_3$) δ 6.66 (s, 1H), 5.29 (s, 2H), 4.28 (q, 2H, J=7.2 Hz), 2.62 (t, 2H, J=6.3 Hz), 2.49 (t, 2H, J=6.3 Hz), 1.92 (m, 2H), 1.75 (m, 2H), 1.33 (t, 3H, J=7.2 Hz); MS (ESI+) m/z 233.1 (M+H)

Example 115j

Ethyl 1-(2-Aminoethyl)-4,5,6,7-tetrahydro-1H-indole-2-carboxylate 115j

A 200-mL Parr reactor bottle was purged with nitrogen and charged with 10% palladium on carbon (50% wet, 1.28 g dry weight), 115i (3.00 g, 12.9 mmol), 12% hydrochloric acid (6.5 mL, 25 mmol), ethyl acetate (60 mL) and ethanol (40 mL). The bottle was attached to a Parr hydrogenator, evacuated, charged with hydrogen gas to a pressure of 50 psi and shaken for 6 h. After this time, the hydrogen was evacuated, and nitrogen was charged into the bottle. Celite 521 (4.0 g) was added, and the mixture was filtered through a pad of Celite 521. The filter cake was washed with ethanol (2×20 mL), and the combined filtrates were concentrated to dryness under reduced pressure. The residue was partitioned between ethyl acetate (150 mL) and 10% aqueous potassium carbonate (100 mL). The organic layer was separated, and the aqueous layer was extracted with ethyl acetate (3×75 mL). The combined organic layers were dried over sodium sulfate and concentrated under reduced pressure. The residue was triturated with ethanol (5 mL) to afford a 71% yield (1.71 g) of 115j as a white solid: mp 102-104° C.; $^1$H NMR (500 MHz, DMSO-$d_6$) δ 6.61 (s, 1H), 6.22 (br, 2H), 4.15 (m, 4H), 2.77 (m, 2H), 2.59 (t, 2H, J=6.5 Hz), 2.42 (t, 2H, J=6.5 Hz), 1.70 (m, 2H), 1.62 (m, 2H), 1.23 (t, 3H, J=7.0 Hz); MS (APCI+) m/z 237.2 (M+H)

Example 115k 3,4,6,7,8,9-Hexahydropyrazino[1,2-a]indol-1(2H)-one 115k

A 100-mL single-neck round-bottomed flask equipped with a magnetic stirrer and nitrogen inlet was purged with nitrogen and charged with ethyl 1-(2-aminoethyl)-4,5,6,7-tetrahydro-1H-indole-2-carboxylate 115j (1.80 g, 7.63 mmol), sodium ethoxide (1.55 g, 22.8 mmol) and ethanol (50 mL). The mixture was stirred at 55° C. for 5 h. After that time, the reaction mixture was concentrated under reduced pressure and the residue was partitioned between ethyl acetate (200 mL) and water (100 mL). The organic layer was separated, and the aqueous layer was extracted with ethyl acetate (2×100 mL). The combined organic layers were washed with brine, dried over sodium sulfate and concentrated under reduced pressure. The residue was purified by column chromato-graphy to afford a 42% yield (605 mg) of 115k as a white solid: mp 207-209° C.; $^1$H NMR (500 MHz, DMSO-$d_6$) δ 7.41 (s, 1H), 6.36 (s, 1H), 3.84 (t, 2H, J=6.0 Hz), 3.42 (m, 2H), 2.51 (t, 2H, J=6.0 Hz), 2.42 (t, 2H, J=6.0 Hz), 1.76 (m, 2H), 1.65 (m, 2H); (APCI+) m/z 191.3 (M+H)

Example 115l

2-Bromo-4-fluoro-6-(1-oxo-3,4,6,7,8,9-hexahydro-pyrazino[1,2-a]indol-2(1H)-yl)benzyl Acetate 115l A 250-mL single-neck round-bottomed flask equipped with a magnetic stirrer was charged with 115k (3.8 g, 20 mmol), 2,6-dibromo-4-fluorobenzyl acetate 101c (20.0 g, 61 mmol), XantPhos (1.16 g, 2.0 mmol), tris(dibenzylideneacetone)dipalladium(0) (1.83 g, 2.0 mmol), Cs$_2$CO$_3$ (16.3 g, 50 mmol), and 1,4-dioxane (120 mL). The system was evacuated and then refilled with N$_2$. A reflux condenser was attached to the flask and the reaction mixture was heated at 100° C. for 16 h. The mixture was cooled to room temperature and filtered. The filtrate was concentrated under reduced pressure and the resulting residue was purified by silica-gel column chromatography eluting with 5:1 petroleum ether/ethyl acetate to afford 115l as a white solid (5.2 g, 60%). MS: [M+H]$^+$ 435. $^1$H NMR (500 MHz, DMSO-$d_6$) δ 7.71-7.69 (m, 1H), 7.49-7.47 (m, 1H), 6.52 (s, 1H), 5.01 (m, 2H), 4.18 (m, 2H), 4.02 (m, 1H), 3.73 (m, 1H), 2.60 (m, 2H), 2.45 (m, 2H), 1.98 (s, 3H), 1.77 (m, 2H), 1.68 (m, 2H).

Example 115m

4-Fluoro-2-(1-oxo-3,4,6,7,8,9-hexahydropyrazino[1,2-a]indol-2(1H)-yl)-6-(4,4,5,5-tetramethyl-1,3,2-dioxaborolan-2-yl)benzyl Acetate 115m A 250-mL single-neck round-bottomed flask equipped with a magnetic stirrer was charged with 115l (3.8 g, 8.8 mmol), (PinB)$_2$ (10.9 g, 43 mmol), Pd(dppf)Cl$_2$ (0.37 g, 0.50 mmol), potassium acetate (2.55 g, 26 mmol), and 1,4-dioxane (150 mL). The system was evacuated and then refilled with N$_2$. A reflux condenser was attached to the flask and the reaction mixture was heated at 100° C. for 15 h. The mixture was cooled to room temperature and filtered. The filtrate was concentrated under reduced pressure and the resulting residue was purified by silica-gel column chromatography eluting with 5:1 petroleum ether/ethyl acetate to afford 115m as a yellow solid (3.2 g, 75%). MS: [M+H]$^+$ 483.

Example 115n (R)-4-Fluoro-2-(1-methyl-5-(5-(2-methyl-4-(oxetan-3-yl)piperazin-1-yl)pyridin-2-ylamino)-6-oxo-1,6-dihydropyridin-3-yl)-6-(1-oxo-3,4,6,7,8,9-hexahydropyrazino[1,2-a]indol-2(1H)-yl)benzyl Acetate 115n

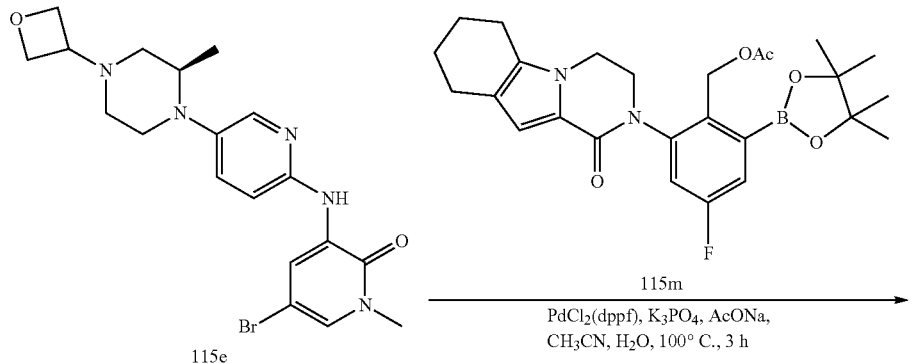

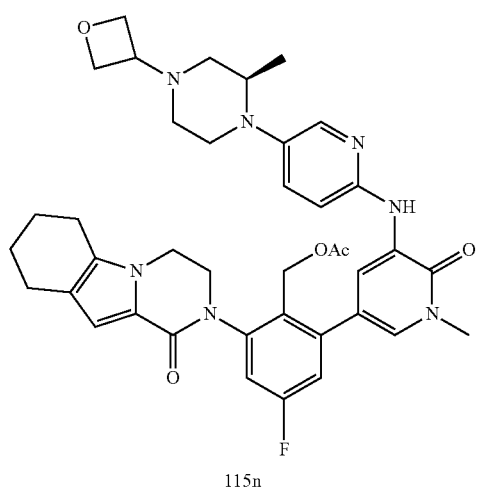

Following the procedure in Example 102 and starting with 115e (220 mg, 0.50 mmol, 1.0 eq.), 115m (482 mg, 1.0 mmol, 2.0 eq.) afforded 115n as a yellow solid (195 mg, 55%). MS: [M+H]+710.4

Example 115

(R)-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one 115

Following the procedure in Example 102 and starting with 115n (190 mg, 0.27 mmol) afforded 115 as a white solid (47 mg, 26%). MS: [M+H]+668.4. $^1$H NMR (500 MHz, DMSO-$d_6$) δ 8.58 (s, 1H), 8.42 (s, 1H), 7.84 (d, J=3.0 Hz, 1H), 7.36-7.32 (m, 3H), 7.25-7.18 (m, 2H), 6.52 (s, 1H), 4.88 (s, 1H), 4.56-4.42 (m, 4H), 4.31-4.30 (m, 2H), 4.18-4.13 (m, 3H), 3.89-3.88 (m, 1H), 3.68-3.67 (m, 1H), 3.58 (s, 3H), 3.39-3.38 (m, 1H), 3.08-3.07 (m, 1H), 2.94-2.93 (m, 1H), 2.51-2.45 (m, 5H), 2.33-2.32 (m, 2H), 2.19-2.18 (m, 1H), 1.79-1.69 (m, 4H), 0.93-0.92 (m, 3H).

Example 116a

{2-[5-({5-[(2S,5R)-2,5-Dimethyl-4-(oxetan-3-yl)piperazin-1-yl]pyridine-2-yl}amino)-1-methyl-6-oxo-1,6-dihydropyridin-3-yl]-6-{4,4-dimethyl-9-oxo-1,10-diazatricyclo[6.4.0.0$^{2,6}$]dodeca-2(6),7-dien-10-yl}-4-fluorophenyl}methyl Acetate 116a

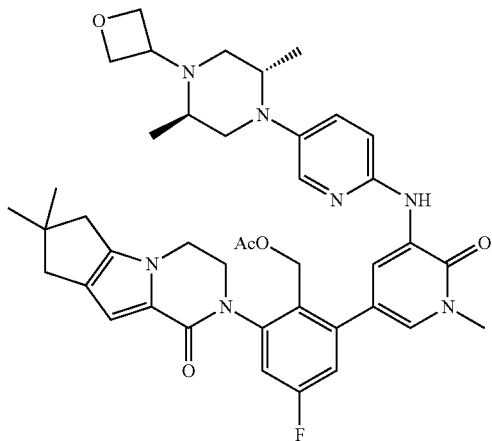

116a

A 25-mL single-neck round-bottomed flask equipped with a magnetic stirrer and a reflux condenser was charged with 5-bromo-3-(5-((2S,5R)-2,5-dimethyl-4-(oxetan-3-yl)piperazin-1-yl)pyridin-2-ylamino)-1-methylpyridin-2(1H)-one 104e (134 mg, 0.30 mmol), 1-methyl-3-(5-(4-(oxetan-3-yl)piperazin-1-yl)pyridin-2-ylamino)-5-(4,4,5,5-tetra-methyl-1,3,2-dioxaborolan-2-yl)pyridin-2(1H)-one 103g (298 mg, 0.6 mmol), Pd(dppf)Cl$_2$ (22 mg, 0.03 mmol), K$_3$PO$_4$ (127 mg, 0.6 mmol), sodium acetate (49 mg, 0.6 mmol), acetonitrile (5 mL), and water (1.0 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with 30:1 dichloromethane/methanol to afford 116a as yellow solid (150 mg, 68%). MS: [M+H]+ 738.3

Example 116

2-(3-{5-[5-((2S,5R)-2,5-Dimethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-7,7-dimethyl-3,4,7,8-tetrahydro-2H,6H-cyclopenta[4,5]pyrrolo[1,2-a]pyrazin-1-one 116

A mixture of 116a (150 mg, 0.20 mmol) and lithium hydroxide (48 mg, 2.0 mmol) in i-propanol/THF (1:1, 4 mL) and water (1 mL) was stirred at 30° C. for 1 h. The mixture was evaporated under reduced pressure. The resulting residue was extracted with ethyl acetate (2×10 mL). The combined organic layer was concentrated under reduced pressure and the residue was purified by reverse-phase prep-HPLC to afford 116 (57 mg, 41%) as white solid. MS: [M+H]+ 696.3. $^1$H NMR (500 MHz, CDCl$_3$) δ 8.60 (dd, J=2.0, 6.5 Hz, 1H), 8.02 (d, J=2.5 Hz, 1H), 7.88 (s, 1H), 7.50-7.49 (m, 1H), 7.37 (d, J=8.5 Hz, 1H), 7.16 (d, J=9.0 Hz, 1H), 6.96 (dd, J=2.5, 9.0 Hz, 1H), 6.83-6.81 (m, 2H), 4.77-4.74 (m, 2H), 4.66-4.62 (m, 2H), 4.57-4.55 (m, 1H), 4.33-4.31 (m, 1H), 4.23-4.14 (m, 3H), 3.92-3.89 (m, 1H), 3.78-3.76 (m, 1H), 3.71 (s, 3H), 3.22-3.20 (m, 1H), 2.93-2.91 (m, 1H), 2.75-2.73 (m, 2H), 2.58 (s, 2H), 2.52 (s, 3H), 1.97-1.90 (m, 2H), 1.28 (s, 6H), 0.91 (d, J=5.5 Hz, 6H).

Example 117a

N-tert-Butyl-4,5,6,7-tetrahydrobenzo[b]thiophene-2-carboxamide 117a

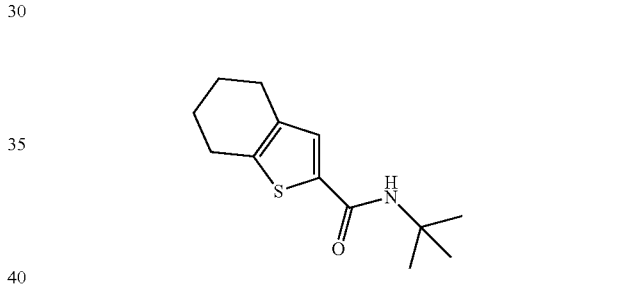

A mixture of 4,5,6,7-tetrahydrobenzo[b]thiophene-2-carboxylic acid (500 g, 2.75 mol, 1.0 equiv) and thionyl chloride (655 g, 5.5 mol, 2.0 equiv) was boiled under reflux for 3 h. Excess thionyl chloride was removed by distillation under reduced pressure. The residue was taken up in dichloromethane (1.0 L) and a solution of tert-butylamine (402 g, 5.5 mol, 2.0 equiv) in dichloromethane (500 mL) was added with stirring while the temperature of the mixture was kept below 10° C. The resulting solution was stirred at 25° C. for 16 h. Most of the solvent was removed under reduced pressure. The residue was chilled in an ice-bath and 2M KOH solution was introduced slowly to adjust the pH to 11 with stirring. The suspension was filtered and the solid was collected, washed three times with water, and dried in vacuo to afford 117a as a white solid (580 g, 80%, over two steps). MS: [M+H]+ 238. $^1$H NMR (500 MHz, CDCl$_3$) δ 7.02 (s, 1H), 5.77 (s, 1H), 2.65 (t, J=6.0 Hz, 1H), 2.47 (t, J=6.0 Hz, 1H), 1.74-1.70 (m, 4H), 1.35 (s, 9H).

Example 117b

N-tert-Butyl-3-(diazenylmethyl)-4,5,6,7-tetrahydrobenzo[b]thiophene-2-carboxamide 117b To a solution of 117a (100 g, 0.42 mol, 1.0 equiv) in THF (500 mL) was slowly added n-BuLi (672 mL, 2.5M in THF, 1.68 mol, 4.0 equiv) at −78° C. under argon. The mixture was stirred for 2 h. DMF (306 g, 4.2 mol, 10.0 equiv) was added to the mixture while the temperature was maintained at −78° C.

After another 2.0 h, the reaction was quenched with methanol (500 mL) at −78° C. It was stirred for 0.50 h at room temperature. 80% aqueous hydrate hydrazine (131 g, 2.1 mol) was added and the mixture was refluxed at 65° C. overnight. The organic solvent was removed under reduced pressure. The residue was filtered and the yellow solid collected was washed with water. The solid was dried in vacuo to afford crude 117b, which was used in the next step without further purification. MS: [M+H]$^+$ 280.

Example 117c

8-Thia-4,5-diazatricyclo[7.4.0.0$^{2,7}$]trideca-(9),2(7),3-trien-6-one 117c

A mixture of 117b (40 g, 144 mmol) in $H_2SO_4$ (30% aqueous, 3 L) was refluxed at 105° C. for 24 h. It was then filtered and the filtrate was extracted by dichloromethane (3×1 L). The combined extract was dried over $Na_2SO_4$ and evaporated under reduced pressure. The residue was purified by silica-gel column chromatography eluting with 100:1 dichloromethane/methanol to afford 117c as a white solid (9.0 g, 31%). MS: [M+H]$^+$ 207. $^1$H NMR (500 MHz, CDCl$_3$) δ 8.15 (s, 1H), 2.96-2.94 (m, 2H), 2.86-2.84 (m, 2H), 1.96-1.94 (m, 4H).

Example 117d (2-Bromo-4-fluoro-6-{6-oxo-8-thia-4,5-diazatricyclo [7.4.0.0$^{2,7}$]trideca-1(9),2(7),3-trien-5-yl}phenyl) methyl acetate 117d A 100-mL single-neck round-bottomed flask equipped with a magnetic stirrer was charged with 117c (1.0 g, 4.85 mmol), 2,6-dibromo-4-fluorobenzyl acetate 101c (4.8 g, 14.6 mmol), copper(I) iodide (553 mg, 2.9 mmol), N$^1$,N$^2$-dimethylethane-1,2-diamine (512 mg, 5.82 mmol), $Cs_2CO_3$ (3.2 g, 9.7 mmol), and 1,4-dioxane (50 mL). The system was evacuated and then refilled with $N_2$. A reflux condenser was attached to the flask, and the reaction mixture was heated at 100° C. for 16 h. It was then cooled to room temperature and filtered. The filtrate was concentrated under reduced pressure and the resulting residue was purified by silica-gel column chromatography eluting with 5:1 petroleum ether/ethyl acetate to afford 117d as a yellow solid (437 mg, 20%). MS: [M+H]$^+$ 451.

Example 117e (4-Fluoro-2-{6-oxo-8-thia-4,5-diazatricyclo[7.4.0.0$^{2,7}$]trideca-1(9),2(7),3-trien-5-yl}-6-(4,4,5,5-tetramethyl-1,3,2-dioxaborolan-2-yl)phenyl)methyl Acetate 117e Following the procedure in Example 104 and starting with 117d (400 mg 0.88 mmol) afforded 117e as a yellow solid (353 mg, 80%). MS: [M+H]$^+$ 499

Example 117f

{4-Fluoro-2-[1-methyl-5-({5-[(2R)-2-methyl-4-(oxetan-3-yl)piperazin-1-yl]pyridin-2-yl}amino)-6-oxopyridin-3-yl]-6-{6-oxo-8-thia-4,5-diazatricyclo [7.4.0.0$^{2,7}$]trideca-1(9),2(7),3-trien-5-yl}phenyl}methyl Acetate 117f

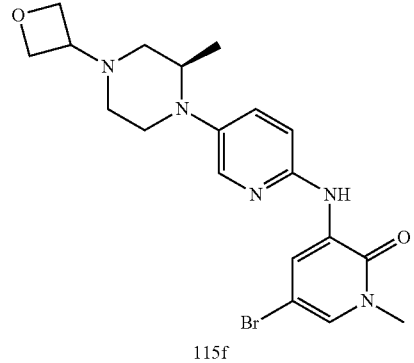

115f

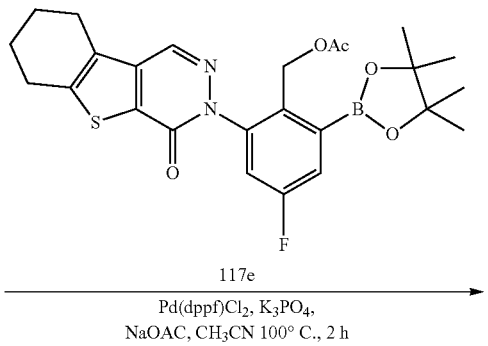

117e

Pd(dppf)Cl$_2$, K$_3$PO$_4$,
NaOAC, CH$_3$CN 100° C., 2 h

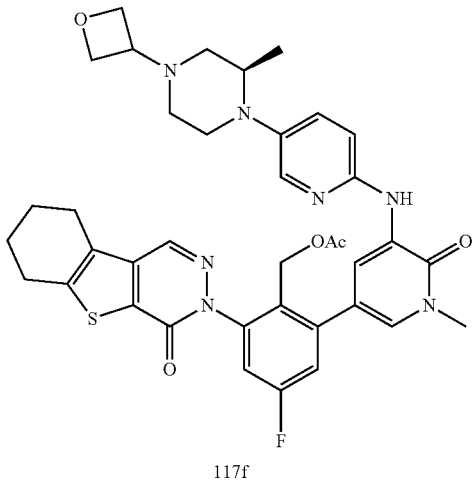

117f

Following the procedure in Example 102 and starting with (R)-5-bromo-1-methyl-3-(5-(2-methyl-4-(oxetan-3-yl)piperazin-1-yl)pyridin-2-ylamino)pyridin-2(1H)-one 115f (217 mg, 0.50 mmol) and 117e (249 mg, 0.50 mmol) afforded 117f as a yellow solid (174 mg, 48%). MS: [M+H]+ 726.

Example 117

3-(5-Fluoro-2-hydroxymethyl-3-{1-methyl-5-[5-((R)-2-methyl-4-oxetan-3-yl-piperazin-1-yl)-pyridin-2-ylamino]-6-oxo-1,6-dihydro-pyridin-3-yl}-phenyl)-6,7,8,9-tetrahydro-3H-benzo[4,5]thieno[2,3-d]pyridazin-4-one 117

Following the procedure in Example 102 and starting with 117f (72 mg, 0.10 mmol) afforded 117 as a yellow solid (35 mg, 51%). LCMS: [M+H]+ 684. $^1$H NMR (500 MHz, DMSO-$d_6$) δ 8.56 (d, J=2.0 Hz, 1H), 8.48 (s, 1H), 8.43 (s, 1H), 7.85 (d, J=2.5 Hz, 1H), 7.37-7.32 (m, 4H), 7.24 (d, J=9.0 Hz, 1H), 4.60 (t, J=5.5 Hz, 1H), 4.57-4.53 (m, 2H), 4.47-4.41 (m, 2H), 4.28-4.27 (d, J=4.0 Hz, 2H), 3.68-3.66 (m, 1H), 3.58 (s, 3H), 3.40-3.38 (m, 1H), 3.10-3.07 (m, 1H), 2.93-2.91 (m, 3H), 2.84-2.82 (m, 2H), 2.54-2.52 (m, 1H), 2.32-2.30 (m, 2H), 2.19-2.18 (m, 1H), 1.89-1.84 (m, 4H), 0.93 (t, J=6.5 Hz, 2H).

Example 118a

{2-[5-({5-[(2S,5R)-2,5-Dimethyl-4-(oxetan-3-yl)piperazin-1-yl]pyridin-2-yl}amino)-1-methyl-6-oxo-1,6-dihydropyridin-3-yl]-4-fluoro-6-{6-oxo-8-thia-4,5-diazatricyclo[7.4.0.0$^{2,7}$]trideca-1(9),2(7),3-trien-5-yl}phenyl}methyl Acetate 118a

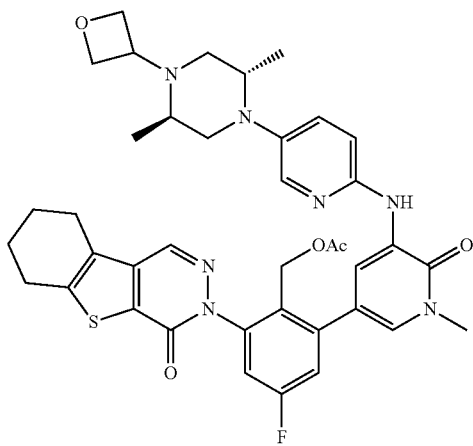

118a

A 25-mL single-neck round-bottomed flask equipped with a magnetic stirrer and a reflux condenser was charged with 5-bromo-3-(5-((2S,5R)-2,5-dimethyl-4-(oxetan-3-yl)piperazin-1-yl)pyridin-2-ylamino)-1-methylpyridin-2(1H)-one 104e (179 mg, 0.40 mmol), (4-fluoro-2-{6-oxo-8-thia-4,5-diazatricyclo[7.4.0.0$^{2,7}$]trideca-1(9),2(7),3-trien-5-yl}-6-(4,4,5,5-tetramethyl-1,3,2-dioxaborolan-2-yl)phenyl)methyl acetate 117d (200 mg, 0.40 mmol), Pd(dppf)Cl$_2$ (29 mg, 0.04 mmol), K$_3$PO$_4$ (170 mg, 0.8 mmol), sodium acetate (66 mg, 0.8 mmol), acetonitrile (5 mL), water (1.0 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with 30:1 dichloromethane/methanol to afford 118a as yellow solid (100 mg, 34%). MS: [M+H]+ 740.3

Example 118

3-(3-{5-[5-((2S,5R)-2,5-Dimethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-6,7,8,9-tetrahydro-3H-benzo[4,5]thieno[2,3-d]pyridazin-4-one 118

A mixture of 118a (100 mg, 0.135 mmol) and lithium hydroxide (33 mg, 1.35 mmol) in i-propanol/THF (1:1, 4 mL) and water (1 mL) was stirred at 30° C. for 1 h. The mixture was evaporated under reduced pressure. The resulting residue was extracted with ethyl acetate (2×10 mL). The combined organic layer was concentrated under reduced pressure and the residue was purified by reverse-phase prep-HPLC to afford 118 (36 mg, 38%) as a white solid. MS: [M+H]+ 698.3. $^1$H NMR (500 MHz, CDCl$_3$) δ 8.64 (d, J=2.0 Hz, 1H), 8.27 (s, 1H), 8.05 (d, J=2.0 Hz, 1H), 7.88 (s, 1H), 7.48 (d, J=2, 5 Hz, 1H), 7.37 (d, J=5.5 Hz, 1H), 7.30 (dd, J=2.5, 9.0 Hz, 1H), 7.11 (dd, J=2.5, 8.5 Hz, 1H), 6.82 (d, J=9.0 Hz, 1H), 4.79-4.73 (m, 2H), 4.67-4.61 (m, 2H), 4.31 (s, 2H), 3.77 (t, J=7.0 Hz, 1H), 3.72 (s, 3H), 3.21-3.19 (m, 1H), 2.99-2.98 (m, 2H), 2.94-2.91 (m, 1H), 2.88-2.86 (m, 2H), 2.78-2.71 (m, 2H), 2.51-2.49 (m, 1H), 1.99-1.96 (m, 6H), 0.92-0.90 (m, 6H).

Example 119a

2-Bromo-4-fluoro-6-(10-fluoro-1-oxo-3,4,6,7,8,9-hexahydropyrazino[1,2-a]indol-2(1H)-yl)benzyl Acetate 119a

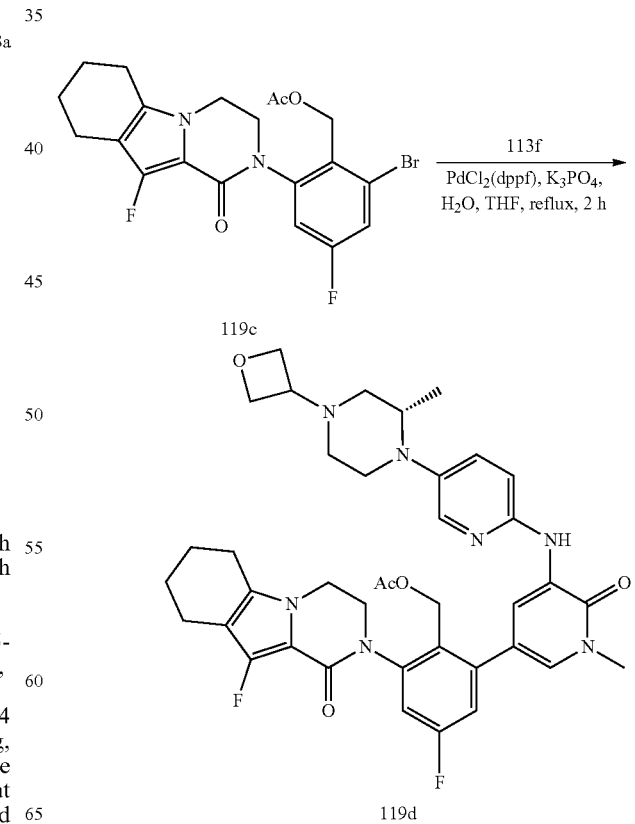

Example 119a

10-Bromo-1H,2H,3H,4H,6H,7H,8H,9H-pyrazino[1,2-a]indol-1-one 119a

Into a 250-mL 3-necked round-bottom flask was placed a solution of 1H,2H,3H,4H,6H,7H,8H,9H-pyrazino[1,2-a]indol-1-one 104j (9.5 g, 49.94 mmol, 1.00 equiv) in N,N-dimethylformamide (100 mL), followed by the addition of N-bromosuccinimide (9.8 g, 55.06 mmol, 1.10 equiv) in several batches at 0° C. The resulting solution was stirred at room temperature for 2 h and diluted with 500 mL of water. The precipitate was filtered and dried in a vacuum oven to afford 9.5 g (71%) of 119a as a light brown solid.

Example 119b

10-Fluoro-1H,2H,3H,4H,6H,7H,8H,9H-pyrazino[1,2-a]indol-1-one 119b

Into a 2-L 4-necked round-bottom flask purged and maintained with an inert atmosphere of nitrogen was placed a solution of 119a (40 g, 148.62 mmol, 1.00 equiv) in tetrahydrofuran (200 mL), followed by the addition of n-BuLi (2.4 M) (218 mL, 3.50 equiv) dropwise with stirring at −78° C. The resulting solution was stirred at −40° C. for 3 h. To this was added a solution of N-fluorobenzenesulfonimide (98.7 g, 313.33 mmol, 2.10 equiv) in tetrahydrofuran (200 mL) dropwise with stirring at −78° C. The resulting solution was stirred at room temperature for 3 h, quenched by the addition of 200 mL of water and extracted with 3×500 mL of ethyl acetate. The combined organic layers were dried over anhydrous sodium sulfate and concentrated under vacuum. The crude product (30 g) was purified by Prep-HPLC with the following conditions (mobile phase, A: 0.05% trifluoroacetic acid/water; B: CH$_3$CN; gradient: 10% B-25% B) to afford 5.05 g (16%) of 119b as a white solid. MS: [M+H]$^+$ 209. 1H NMR (300 MHz, CDCl$_3$) δ 6.16 (br, 1H), 3.90-3.86 (m, 2H), 3.65-3.62 (m, 2H), 2.53-2.47 (m, 4H), 1.88-1.80 (m, 2H), 1.77-1.72 (m, 2H).

Example 119c

2-Bromo-4-fluoro-6-(10-fluoro-1-oxo-3,4,6,7,8,9-hexahydropyrazino[1,2-a]indol-2(1H)-yl)benzyl Acetate 119c A 100-mL single-neck round-bottomed flask equipped with a magnetic stirrer and reflux condenser was charged with 1,4-dioxane (60 mL), 2,6-dibromo-4-fluorobenzyl acetate 101C (2.34 g, 7.2 mmol), 119b (500 mg, 2.4 mmol), and cesium carbonate (1.6 g, 4.8 mmol). After bubbling nitrogen through the resulting mixture for 30 minutes, Xantphos (140 mg, 0.24 mmol) and tris(dibenzylideneacetone)dipalladium (0) (220 mg, 0.24 mmol) were added and the reaction mixture was heated at 100° C. for 12 h. After this time the reaction was cooled to room temperature and filtered. The filtrate was partitioned between ethyl acetate (40 mL) and water (40 mL). The aqueous layer was separated and extracted with ethyl acetate (3×70 mL). The combined organic layer was washed with brine (30 mL) and dried over sodium sulfate. The drying agent was removed by filtration and the filtrate was concentrated under reduced pressure. The residue was purified by silica-gel column eluting with 3:1 petroleum ether/ethyl acetate to afford 119c (632 mg, 58%) as a yellow solid. MS: [M+H]$^+$ 453.2

Example 119d (S)-4-Fluoro-2-(10-fluoro-1-oxo-3,4,6,7,8,9-hexahydropyrazino[1,2-a]indol-2(1H)-yl)-6-(1-methyl-5-(5-(2-methyl-4-(oxetan-3-yl)piperazin-1-yl)pyridin-2-ylamino)-6-oxo-1,6-dihydropyridin-3-yl)benzyl Acetate 119d A 50-mL single-neck round-bottomed flask equipped with a magnetic stirrer and a reflux condenser was charged with 119c (150 mg, 1.0 eq., 0.33 mmol), (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 113f (160 mg, 1.0 eq., 0.33 mmol), K$_3$PO$_4$ (210 mg, 3.0 eq., 0.99 mmol), PdCl$_2$(dppf) (27.0 mg, 0.10 eq., 0.033 mmol), THF (20 mL), and water (0.1 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with 40:1 dichloromethane/methanol to afford 119d as a yellow solid (90 mg, 37%). MS: [M+H]$^+$ 728.3.

Example 119

(S)-10-fluoro-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one 119

A 50-mL single-neck round-bottomed flask was charged with 119d (90 mg, 1.0 eq., 0.12 mmol), lithium hydroxide (9.0 mg, 3.0 eq., 0.37 mmol), i-propanol (3 mL), THF (3 mL), and water (2 mL). The mixture was stirred at room temperature for 1 h. It was then filtered and concentrated. The residue was purified by reverse-phase prep-HPLC to afford 119 (42 mg, 49%). MS: [M+H]$^+$ 686.3. $^1$H NMR (500 MHz, CDCl$_3$) δ 8.54 (dd, J=2.0 Hz, 9.0, 1H), 7.94-7.93 (m, 1H), 7.81 (d, J=4.0 Hz, 1H), 7.45-7.44 (m, 1H), 7.31 (dd, J=3.0, 9.0 Hz, 1H), 7.15-7.14 (m, 1H), 6.94 (dd, J=2.0, 9.0 Hz, 1H), 6.81 (d, J=8.5 Hz, 1H), 4.71-4.61 (m, 4H), 4.53 (d, J=9.5 Hz, 1H), 4.32-4.31 (m, 2H), 4.15-4.08 (m, 3H), 3.89-3.86 (m, 1H), 3.69 (s, 3H), 3.55-3.43 (m, 2H), 3.07 (m, 2H), 2.57-2.46 (m, 7H), 2.20-2.16 (m, 1H), 1.88-1.76 (m, 4H), 0.98-096 (m, 3H).

Example 120a

{2-[5-({5-[(2S)-2-Ethyl-4-(oxetan-3-yl)piperazin-1-yl]pyridin-2-yl}amino)-1-methyl-6-oxo-1,6-dihydropyridin-3-yl]-4-fluoro-6-{6-oxo-8-thia-4,5-diazatricyclo[7.4.0.0$^{2,7}$]trideca-1(9),2(7),3-trien-5-yl}phenyl}methyl Acetate 120a

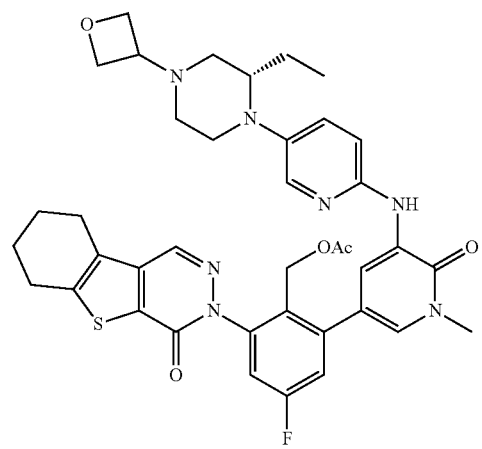

A 25-mL single-neck round-bottomed flask equipped with a magnetic stirrer and a reflux condenser was charged with (S)-5-bromo-3-(5-(2-ethyl-4-(oxetan-3-yl)piperazin-1-yl) pyridin-2-ylamino)-1-methylpyridin-2(1H)-one 114e (179 mg, 0.40 mmol), (4-fluoro-2-{6-oxo-8-thia-4,5-diazatricyclo [7.4.0.0²,⁷]trideca-1(9),2(7),3-trien-5-yl}-6-(4,4,5,5-tetramethyl-1,3,2-dioxaborolan-2-yl)phenyl)methyl acetate 117e (200 mg, 0.40 mmol), Pd(dppf)Cl$_2$ (29 mg, 0.04 mmol), K$_3$PO$_4$ (170 mg, 0.8 mmol), sodium acetate (66 mg, 0.8 mmol), acetonitrile (5 mL), and water (1.0 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with 30:1 dichloromethane/methanol to afford 120a as a yellow solid (120 mg, 41%). MS: [M+H]$^+$ 740.3

Example 120

3-(3-{5-[5-((S)-2-Ethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-6,7,8,9-tetrahydro-3H-benzo[4,5]thieno[2,3-d]pyridazin-4-one 120

A mixture of 120a (120 mg, 0.16 mmol) and lithium hydroxide (38 mg, 1.6 mmol) in i-propanol/THF (1:1, 4 mL) and water (1 mL) was stirred at 30° C. for 1 h. The mixture was evaporated under reduced pressure. The resulting residue was extracted with ethyl acetate (2×10 mL). The combined organic layer was concentrated under reduced pressure and the residue was purified by reverse-phase prep-HPLC to afford 120 (73 mg, 65%) as a white solid. MS: [M+H]$^+$ 698.3. $^1$H NMR (500 MHz, CDCl$_3$) δ 8.58 (d, J=1.5 Hz, 1H), 8.26 (s, 1H), 7.94 (d, J=2.5 Hz, 1H), 7.80 (s, 1H), 7.45 (d, J=2.5 Hz, 1H), 7.30 (d, J=9.0 Hz, 1H), 7.27 (d, J=9.0 Hz, 1H), 7.11 (dd, J=2.5, 8.0 Hz, 1H), 6.82 (d, J=9.0 Hz, 1H), 4.72-4.62 (m, 4H), 4.31 (s, 2H), 4.01 (bs, 1H), 3.71 (s, 3H), 3.53 (t, J=6.0 Hz, 1H), 3.34-3.32 (m, 1H), 3.13 (t, J=6.0 Hz, 2H), 2.99 (t, J=5.0 Hz, 2H), 2.87 (t, J=5.0 Hz, 2H), 2.60-2.56 (m, 1H), 2.46-2.44 (m, 2H), 2.36-2.34 (m, 1H), 2.01-1.96 (m, 4H), 1.71-1.68 (m, 1H), 1.44-1.36 (m, 1H), 0.83 (t, J=7.5 Hz, 3H).

Example 121a

Ethyl 4,5,6,7-Tetrahydro-1H-indole-2-carboxylate 121a

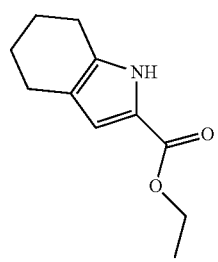

To a mixture of ethyl 3-(2-chlorocyclohex-1-enyl)acrylate (21.4 g, 100 mmol) in DMSO (100 mL) was added sodium azide (9.75 g, 150 mmol). The reaction mixture was heated at 105° C. for 4 h. After cooling to room temperature, the mixture was poured into ice water. The resulting precipitate was collected by filtration to afford 121a (18.0 g, 93.3%). MS-ESI: [M+H]$^+$ 194.

Example 121b

Ethyl 1-(2,2-Diethoxyethyl)-4,5,6,7-tetrahydro-1H-indole-2-carboxylate 121b

To a suspension of NaH (1.44 g, 60.2 mmol) in N,N-dimethylformamide (DMF)(30 mL) was slowly added 121a (5.80 g, 30.1 mmol) at 0° C. The resulting mixture was stirred at room temperature for 0.5 h, followed by the addition of 2-bromo-1,1-diethoxyethane (11.9 g, 60.2 mmol). The reaction was heated at 70° C. for 30 h and quenched with water (100 mL). The mixture was then extracted with ethyl acetate (3×100 mL). The combined organic phase was concentrated under reduced pressure and the residue was purified with silica-gel column chromatography eluting with 40:1 petroleum ether/ethyl acetate to afford 121b (4.7 g, 51%). MS-ESI: [M-ethanol+H]$^+$ 264. $^1$H NMR (500 MHz, DMSO-d$_6$) δ 6.65 (s, 1H), 4.59 (t, J=5.0 Hz, 1H), 4.17-4.16 (m, 4H), 3.59-3.57 (m, 2H), 3.27-3.26 (m, 2H), 2.61 (t, J=6.0 Hz, 2H), 2.51 (t, J=6.0 Hz, 2H), 1.73-1.71 (m, 2H), 1.63-1.61 (m, 2H), 1.25 (t, J=7.0 Hz, 3H), 1.02 (t, J=7.0 Hz, 6H).

Example 121c 1-(2,2-Diethoxyethyl)-4,5,6,7-tetrahydro-1H-indole-2-carboxylic Acid 121c To a mixture of 121b (4.7 g, 15.2 mmol) in a mixed solvent of ethanol (20 mL), tetrahydrofuran (20 mL), and water (30 mL) was added sodium hydroxide (3.0 g, 75.0 mmol). The reaction was heated at 75° C. for two days and concentrated under reduced pressure. The residue was suspended in water and neutralized with diluted aqueous citric acid solution. The mixture was extracted with ethyl acetate (3×100 mL) and the combined organic phase was concentrated under reduced pressure to afford 121c (3.32 g, 78%). MS-ESI: [M-ethanol+H]$^+$ 236.

Example 121d 1-(2,2-Diethoxyethyl)-4,5,6,7-tetrahydro-1H-indole-2-carboxamide 121d To a mixture of 121c (2.8 g, 10.0 mmol) in N,N-dimethylformamide (30 mL) was added O-(7-azabenzotriazol-1-yl)-N,N,N',N'-tetramethyluronium hexafluorophosphate (HATU) (5.7 g, 15.0 mmol), triethylamine (1.5 g, 15.0 mmol), and DMAP (128 mg, 1.0 mmol). The reaction mixture was stirred at room temperature overnight. Saturated ammonium hydroxide (30 mL) was added and the resulting mixture was further stirred for 2 h. It was then diluted with water (100 mL) and extracted with ethyl acetate (3×100 mL). The combined organic phase was concentrated under reduced pressure and the residue was purified by silica-gel column chromatography eluting with petroleum ether/ethyl acetate (6:1 to 3:1) to afford 121d (2.7 g, 96%). MS-ESI: [M-ethanol+H]$^+$ 235. $^1$H NMR (500 MHz, DMSO) δ 7.35 (bs, 1H), 6.70 (bs, 1H), 6.60 (s, 1H), 4.60 (t, J=5.5 Hz, 1H), 4.18 (d, J=4.0 Hz, 2H), 3.57-3.56 (m, 2H), 3.25 (m, 2H), 2.57 (t, J=6.0 Hz, 2H), 2.40 (t, J=6.0 Hz, 2H), 1.71 (t, J=5.0 Hz, 2H), 1.64 (t, J=5.0 Hz, 2H), 1.01 (t, J=7.0 Hz, 6H).

Example 121e

6,7,8,9-Tetrahydropyrazino[1,2-a]indol-1(2H)-one 121e

A mixture of 121d (2.7 g, 9.6 mmol) and acetic acid (10 mL) was heated at 110° C. for 2 h. The mixture was cooled to room temperature and neutralized with aqueous sodium carbonate solution and extracted with ethyl acetate (3×30 mL). The combined organic phase was concentrated under reduced pressure to afford 121e as a yellow solid (1.6 g, 88%). MS-ESI: [M+H]$^+$ 189.3. $^1$H NMR (500 MHz, DMSO-d$_6$) δ 10.28 (s, 1H), 7.02 (d, J=5.5 Hz, 1H), 6.63 (s, 1H), 6.52 (pt, J=5.5 Hz, 1H), 2.66 (t, J=6.0 Hz, 2H), 2.57 (t, J=6.0 Hz, 2H), 1.83-1.82 (m, 2H), 1.73-1.72 (m, 2H).

Example 121f

2-Bromo-4-fluoro-6-(1-oxo-6,7,8,9-tetrahydropyrazino[1,2-a]indol-2(1H)-yl)benzaldehyde 121f A 100-mL single-neck round-bottomed flask equipped with a magnetic stirrer and a reflux condenser was charged with 121e (500 mg, 2.66 mmol), 2,6-dibromo-4-fluorobenzaldehyde (1.50 g, 5.32 mmol), and potassium acetate (521 mg, 5.32 mmol). After bubbling argon through the suspension for 30 minutes, 4,7-dimethoxy-1,10-phenanthroline (638.4 mg, 2.66 mmol) and cuprous iodide (506 mg, 2.66 mmol) were added. The system was subjected to three cycles of vacuum/argon flush and then heated at 100° C. for 16 h. It was then cooled to room temperature and filtered. The solid was washed with dichloromethane (2×100 ml). The combined filtrate was concentrated under reduced pressure and the residue was purified by silica-gel column chromatography eluting with petroleum ether/ethyl acetate (10:1 to 3:1) to afford 121f (510 mg, 49%) as a yellow solid. MS: [M+H]$^+$ 389.

Example 121g

3-(5-((2S,5R)-2,5-Dimethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 121g

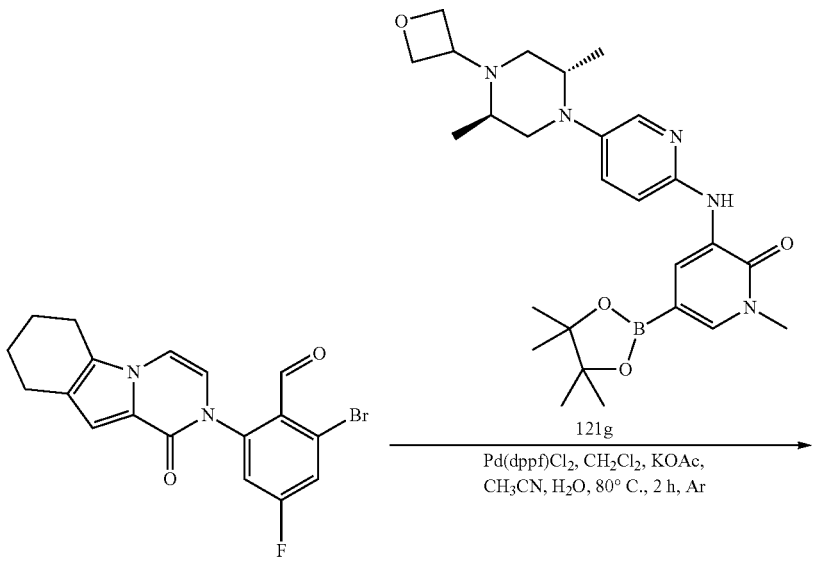

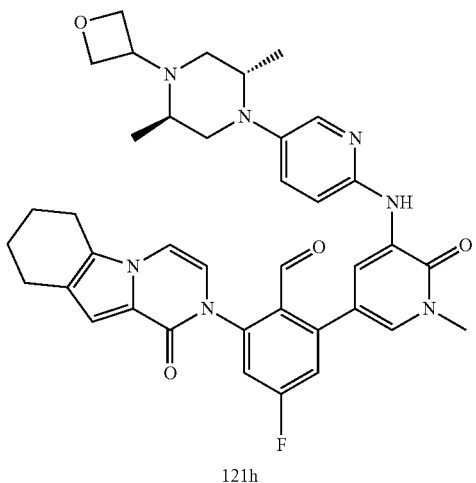

A 100-mL single-neck round-bottomed flask equipped with a magnetic stirrer and a reflux condenser was charged with 5-bromo-3-(5-((2S,5R)-2,5-dimethyl-4-(oxetan-3-yl)piperazin-1-yl)pyridin-2-ylamino)-1-methylpyridin-2(1H)-one 104e (3.0 g, 6.70 mmol), Pin$_2$B$_2$ (8442 mg, 33.5 mmol), Pd$_2$(dba)$_3$ (311 mg, 0.34 mmol), X-phos (319 mg, 0.67 mmol), potassium acetate (1970 mg, 20.1 mmol), and dioxane (50 mL). After three cycles of vacuum/argon flush, the mixture was heated at 60° C. for 16 h. It was then cooled to room temperature and filtered. The filtrate was concentrated under reduced pressure. The resulting residue was washed with 8:1 petroleum ether/ethyl acetate (80 mL) to afford 121g as a yellow solid (3 g, 90%). MS: [M+H]$^+$ 496.4.

Example 121h 2-(5-(5-((2S,5R)-2,5-Dimethyl-4-(oxetan-3-yl)piperazin-1-yl)-pyridin-2-ylamino)-1-methyl-6-oxo-1,6-dihydropyridin-3-yl)-4-fluoro-6-(1-oxo-6,7,8,9-tetrahydropyrazino[1,2-a]indol-2(1H)-yl)benzaldehyde 121h A 50-mL round-bottomed flask was charged with 121f (194 mg, 0.5 mmol), 121g (347.0 mg, 0.7 mmol), potassium acetate (98.0 mg, 1.0 mmol), 1,1'-bis(diphenylphosphino)ferrocene-dichloropalladium(II) (20.4 mg, 0.025 mmol), water (0.5 mL), and acetonitrile (20 mL). The system was subjected to 3 cycles of vacuum/argon flush and heated at 100° C. under argon atmosphere and for 3h. Analysis of the reaction mixture by LCMS showed little start materials remained. The reaction mixture was cooled to room temperature and filtered. The filtrate was diluted with dichloromethane (50 mL) and water (50 mL). The aqueous layer was separated and extracted with dichloromethane (3×20 mL). The combined organic layer was dried over Na$_2$SO$_4$, filtered, and concentrated under reduced pressure. The dark residue was purified by silica-gel column chromatography eluting with dichloromethane/methanol (80/1 to 30/1) to afford 121g (182 mg, 54%) as yellow solid. MS: [M+H]$^+$ 678.

Example 121

2-(3-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-6,7,8,9-tetrahydropyrazino[1,2-a]indol-1(2H)-one 121

To a solution of 121h (150 mg, 0.22 mmol) in methanol (10 mL) was added NaBH$_4$ (41.8 mg, 1.1 mmol) at room temperature. After the reaction was stirred for 1 h, LCMS indicated the reaction was complete. The mixture was poured into water (30 mL) and concentrated under reduced pressure. The residue was extracted with dichloromethane (3×30 mL). The combined organic layer was washed with brine (30 mL), dried over Na$_2$SO$_4$, filtered, and concentrated under reduced pressure. The residue solid was purified by prep-HPLC to afford 121 (60.3 mg, 40%) as white solid. MS: [M+H]$^+$ 680. $^1$H NMR (500 MHz, DMSO-d$_6$) δ 8.63 (d, J=2.0 Hz, 1H), 8.51 (s, 1H), 7.90 (d, J=3.0 Hz, 1H), 7.41 (m, 2H), 7.31-7.23 (m, 4H), 6.78 (d, J=1.0 Hz, 2H), 4.80 (m, 1H), 4.55-4.54 (m, 2H), 4.49-4.4.48 (m, 2H), 4.28-4.20 (m, 2H), 3.69-3.64 (m, 1H), 3.60 (s, 3H), 3.29-3.27 (m, 2H), 2.89-2.88 (m, 1H), 2.75-2.67 (m, 4H), 2.61 (m, 2H), 1.93-1.86 (m, 3H), 1.59 (m, 2H), 0.85-0.81 (m, 6H).

Example 122a (S)-3-(5-(2-Ethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 122a

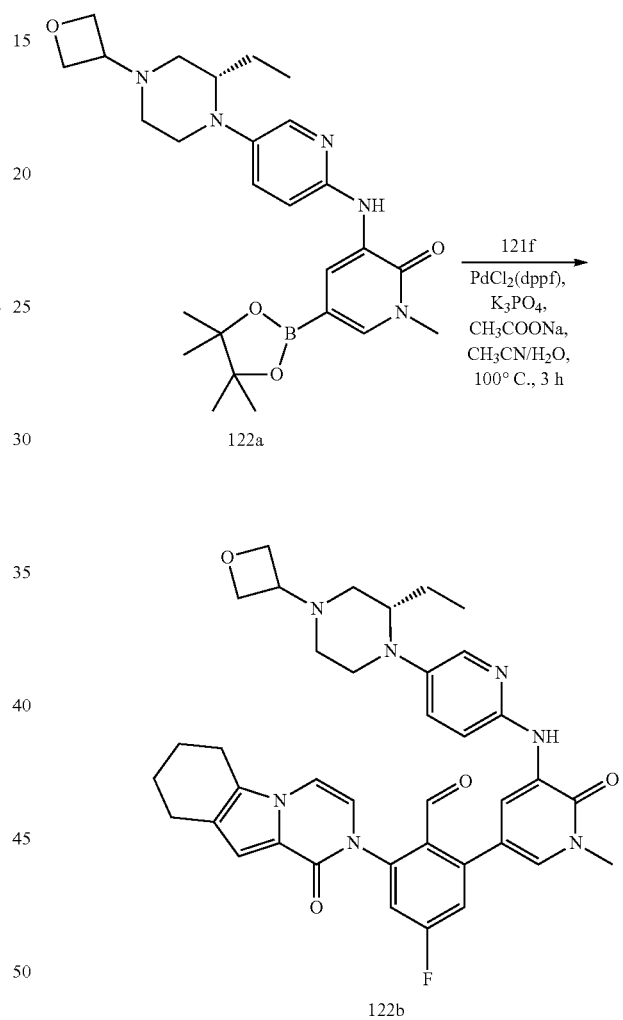

A 100-mL single-neck round-bottomed flask equipped with a magnetic stirrer and a reflux condenser was charged with (S)-5-bromo-3-(5-(2-ethyl-4-(oxetan-3-yl)piperazin-1-yl)pyridine-2-ylamino)-1-methylpyridin-2(1H)-one 114e (3219 mg, 7.20 mmol), Pin$_2$B$_2$ (9072 mg, 36.0 mmol), Pd$_2$(dba)$_3$ (329 mg, 0.36 mmol), X-phos (302 mg, 0.72 mmol), potassium acetate (2117 mg, 21.6 mmol), and dioxane (50 mL). After three cycles of vacuum/argon flush, the mixture was heated at 60° C. for 16 h. It was then cooled to room temperature and filtered. The filtrate was concentrated under reduced pressure and the resulting residue was washed with 8:1 petroleum ether/ethyl acetate (80 mL) to afford 122a as a yellow solid (3.0 g, 84%).

Example 122b (S)-2-(5-(5-(2-Ethyl-4-(oxetan-3-yl)piperazin-1-yl)pyridin-2-ylamino)-1-methyl-6-oxo-1,6-dihydropyridin-3-yl)-4-fluoro-6-(1-oxo-6,7,8,9-tetrahydropyrazino[1,2-a]indol-2(1H)-yl)benzaldehyde 122b A round-bottomed flask was charged with 2-bromo-4-fluoro-6-(1-oxo-6,7,8,9-tetrahydropyrazino[1,2-a]indol-2(1H)-yl)benzaldehyde 121f (159 mg, 0.41 mmol), 122a (213 mg, 0.43 mmol), PdCl$_2$(dppf) (29 mg, 0.04 mmol), K$_3$PO$_4$ (182 mg, 0.86 mmol), sodium acetate (71 mg, 0.86 mmol), acetonitrile (15 mL), and water (1.5 mL). After three cycles of vacuum/argon flush, the mixture was heated at 80° C. for 3 h. It was then filtered and the filtrate was evaporated under reduced pressure. The residue was purified by silica-gel column chromatography eluting with 1:20 methanol/dichloromethane to afford 122b as a red solid (120 mg, 43%). MS: [M+H]$^+$ 678.3

Example 122

(S)-2-(3-(5-(5-(2-ethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-6,7,8,9-tetrahydropyrazino[1,2-a]indol-1(2H)-one 122

A mixture of 122b (100 mg, 0.15 mmol), NaBH$_4$ (22 mg, 0.60), and methanol (10 mL) was stirred at 25° C. for 1 h. It was then quenched with water (5 mL) and concentrated under reduced pressure. The residue was extracted with dichloromethane (2×10 mL) and the combined organic layer was concentrated under reduced pressure. The residue was purified by reverse-phase prep-HPLC to afford 122 (32 mg, 31%). MS: [M+H]$^+$ 680.3. $^1$H NMR (500 MHz, CDCl$_3$) δ 8.56 (s, 1H), 7.91 (s, 1H), 7.80 (s, 1H), 7.53 (s, 1H), 7.28-7.26 (m, 2H), 7.05 (s, 1H), 6.97-6.93 (m, 2H), 6.81 (d, J=8.5 Hz, 1H), 6.45 (d, J=5.5 Hz, 1H), 4.71-4.61 (m, 4H), 4.38 (d, J=12.0 Hz, 1H), 4.36 (d, J=11.5 Hz, 1H), 3.70 (s, 3H), 3.52 (bs, 1H), 3.31 (d, J=5.5 Hz, 1H), 3.13-3.10 (m, 2H), 2.75-2.70 (m, 4H), 2.56-2.43 (m, 4H), 1.98-1.96 (m, 2H), 1.85-1.84 (m, 2H), 1.39-1.36 (m, 2H), 0.82 (t, J=7.0 Hz, 3H).

Example 123a 2-(5-(5-(2-Ethyl-4-(oxetan-3-yl)piperazin-1-yl)pyridin-2-ylamino)-1-methyl-6-oxo-1,6-dihydropyridin-3-yl)-4-fluoro-6-(1-oxo-3,4,6,7,8,9-hexahydropyrido[3,4-b]indolizin-2(1H)-yl)benzyl Acetate 123a

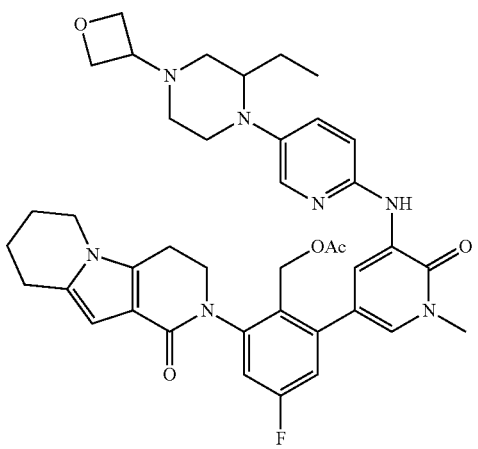

A 100-mL single-neck round-bottomed flask was charged with 2-bromo-4-fluoro-6-(1-oxo-3,4,6,7,8,9-hexahydropyrido[3,4-b]indolizin-2(1H)-yl)benzyl acetate 101h (120 mg, 0.27 mmol), (S)-3-(5-(2-ethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 122a (158.4 mg, 0.32 mmol), Pd(dppf)Cl$_2$ (24.5 mg, 0.03 mmol), K$_3$PO$_4$ (114.5 mg, 0.54 mmol), sodium acetate.trihydrate (73.4 mg, 0.54 mmol), water (0.5 mL), and acetonitrile (20 mL). The system was evacuated and refilled with N$_2$. The reaction mixture was heated at 100° C. for 2 h. It was then cooled to room temperature and filtered. The filtrate was concentrated under reduced pressure and the resulting residue was purified by silica-gel column chromatography eluting with 25:1 dichloromethane/methanol to afford 123a (105 mg, 53%) as a yellow brown solid. MS: [M+H]$^+$ 724.3.

Example 123

(S)-2-(3-(5-(5-(2-ethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrido[3,4-b]indolizin-1(2H)-one 123

A mixture of 123a (105 mg, 0.15 mmol) and lithium hydroxide (36 mg, 1.5 mmol) in i-propanol/THF (1:1, 4 mL) and water (1 mL) was stirred at 30° C. for 1 h. The mixture was evaporated under reduced pressure and the residue was extracted with ethyl acetate (2×10 mL). The combined ethyl acetate extract was concentrated under reduced pressure and the residue was purified by reverse-phase prep-HPLC to afford 123 (40 mg, 40%) as a pale pink solid. MS: [M+H]$^+$ 682.3. $^1$H NMR (500 M, CHCl$_3$) δ 8.55 (s, 1H), 7.93 (s, 1H), 7.82 (s, 1H), 7.51 (s, 1H), 7.29 (d, J=3.5 Hz, 1H), 7.15-7.12 (m, 1H), 6.94 (dd, J=3.5 Hz, 10.5, 1H), 6.81 (d, J=10.0 Hz, 1H), 6.30 (s, 1H), 4.77-4.74 (m, 4H), 4.72-4.70 (m, 1H), 4.57-4.55 (m, 1H), 4.29-4.24 (m, 1H), 4.12-4.05 (m, 1H), 3.90-3.78 (m, 4H), 3.70 (s, 3H), 3.52-3.50 (m, 1H), 3.32-3.30 (m, 1H), 3.12-3.10 (m, 2H), 3.04-2.83 (m, 2H), 2.81 (m, 2H), 2.57-2.50 (m, 1H), 2.43-2.33 (m, 2H), 2.05-2.00 (m, 2H), 1.87-1.85 (m, 2H), 1.49-1.35 (m, 2H), 0.81 (t, J=8.5 Hz, 3H).

Example 124a (2-{4,4-Dimethyl-9-oxo-1,10-diazatricyclo[6.4.0.0$^{2,6}$]dodeca-2(6),7-dien-10-yl}-4-fluoro-6-[1-methyl-5-({5-[(2R)-2-methyl-4-(oxetan-3-yl)piperazin-1-yl]pyridin-2-yl}amino)-6-oxo-1,6-dihydropyridin-3-yl]phenyl)methyl Acetate 124a

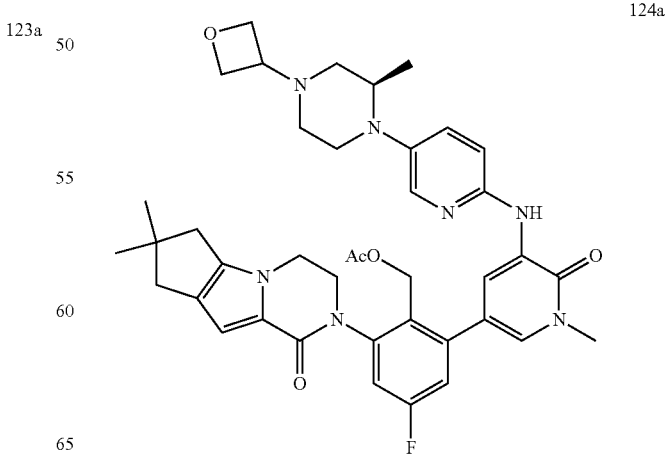

A round-bottomed flask equipped with a magnetic stirrer and a reflux condenser was charged with (R)-5-bromo-1-methyl-3-(5-(2-methyl-4-(oxetan-3-yl)piperazin-1-yl)pyridin-2-ylamino)pyridin-2(1H)-one 115f (152 mg, 0.35 mmol), (2-{4,4-dimethyl-9-oxo-1,10-diazatricyclo[6.4.0.0$^{2,6}$]dodeca-2(6),7-dien-10-yl}-4-fluoro-6-(4,4,5,5-tetramethyl-1,3,2-dioxaborolan-2-yl)phenyl)methyl acetate 103g (206 mg, 0.415 mmol), PdCl$_2$(dppf) (28 mg, 0.04 mmol), K$_3$PO$_4$ (147 mg, 0.69 mmol), sodium acetate (57 mg, 0.69 mmol), acetonitrile (20 mL), and water (2 mL). After three cycles of vacuum/argon flush, the mixture was heated at 100° C. for 3 h. It was then filtered and the filtrate was evaporated under reduced pressure. The residue was purified on silica-gel column chromatography eluting with 1:20 methanol/dichloromethane to afford 124a as red solid (70 mg, 28%). MS: [M+H]$^+$ 724.2

Example 124

2-(5-Fluoro-2-hydroxymethyl-3-{1-methyl-5-[5-((R)-2-methyl-4-oxetan-3-yl-piperazin-1-yl)-pyridin-2-ylamino]-6-oxo-1,6-dihydro-pyridin-3-yl}-phenyl)-7,7-dimethyl-3,4,7,8-tetrahydro-2H,6H-cyclopenta[4,5]pyrrolo[1,2-a]pyrazin-1-one 124

A mixture of 124a (59 mg, 0.080 mmol), lithium hydroxide (19 mg, 0.80 mmol), THF (10 mL), i-propanol (8 mL), and water (10 mL) was stirred at room temperature for 1.5 h. It was then concentrated under reduced pressure and the residue was extracted with dichloromethane (2×10 mL). The combined dichloromethane extract was concentrated under reduced pressure. The residue was purified with reverse-phase prep-HPLC to afford 124 (43 mg, 79%). MS: [M+H]$^+$ 682.3. $^1$H NMR (500 MHz, DMSO-d$_6$) δ 8.58-8.57 (m, 1H), 8.41 (s, 1H), 7.84 (d, J=3.0 Hz, 1H), 7.37-7.31 (m, 3H), 7.22 (d, J=9.5 Hz, 1H), 7.19-7.16 (m, 1H), 6.50 (s, 1H), 4.87 (d, J=2.0 Hz, 1H), 4.57-4.53 (m, 2H), 4.46 (t, J=6.0 Hz, 1H), 4.41 (t, J=6.0 Hz, 1H), 4.31 (d, J=3.0 Hz, 2H), 4.21-4.18 (m, 2H), 4.15-4.10 (m, 1H), 3.88-3.85 (m, 1H), 3.67 (d, J=2.0 Hz, 1H), 3.58 (s, 3H), 3.41-3.37 (m, 2H), 3.10-3.07 (m, 1H), 2.95-2.91 (m, 1H), 2.56 (d, J=1.5 Hz, 2H), 2.41 (s, 2H), 2.32-2.28 (m, 2H), 2.17-2.15 (m, 1H), 1.21 (s, 6H), 0.91 (d, J=6.5 Hz, 3H)

Example 125a tert-Butyl 3,3-Dimethyl-4-(6-nitropyridin-3-yl)piperazine-1-carboxylate 125a A 100-mL single-neck round-bottomed flask equipped with a magnetic stirrer and a reflux condenser was charged with 5-bromo-2-nitropyridine (5.6 g, 28.0 mmol), tert-butyl 3,3-dimethyl-piperazine-1-carboxylate (3.0 g, 14.0 mmol), cesium carbonate (9.1 g, 28 mmol), and 1,4-dioxane (50 mL). After bubbling nitrogen through the resulting solution for 30 min, Binap (870 mg, 1.4 mmol) and tris(dibenzylideneacetone)dipalladium(0) (1.2 g, 1.4 mmol) were added. The reaction mixture was subjected to three cycles of vacuum/argon flush and stirred at 120° C. for 24 h. After this time the reaction was cooled to room temperature it was filtered and the filtrate was partitioned between ethyl acetate (200 mL) and water (50 mL). The aqueous layer was separated and extracted with ethyl acetate (3×50 mL). The combined organic layer was washed with brine (50 mL) and dried over sodium sulfate. The drying agent was removed by filtration and the filtrate was concentrated under reduced pressure. The residue was purified by silica-gel column chromatography eluting with 5:1 petroleum ether/ethyl acetate to afford 125a (1.27 g, 27%). LCMS: [M+H]$^+$ 337.2.

Example 125b tert-Butyl 4-(6-Aminopyridin-3-yl)-3,3-dimethylpiperazine-1-carboxylate 125b A 50-mL round-bottomed flask was purged with nitrogen and charged with 125a (1100 mg, 3.2 mmol), 10% palladium on carbon (10% wet, 110 mg), and methanol (20 mL). It was then evacuated, charged with hydrogen gas, and stirred at room temperature for 5 h. The hydrogen was evacuated and nitrogen was charged into the flask. The catalyst was removed by filtration through a pad of Celite and the filtrate was concentrated under reduced pressure to afford 125b (950 mg, 94%). LCMS: [M+H]$^+$ 307.3

Example 125c tert-Butyl 4-(6-(5-Bromo-1-methyl-2-oxo-1,2-dihydropyridin-3-ylamino) pyridin-3-yl)-3,3-dimethylpiperazine-1-carboxylate 125c A 100-mL single-neck round-bottomed flask equipped with a magnetic stirrer and a reflux condenser was charged with 125b (950 mg, 3.1 mmol), 3,5-dibromo-1-methylpyridin-2(1H)-one (1240 mg, 4.6 mmol), 1,4-dioxane (30 mL), and cesium carbonate (2015 mg, 6.2 mmol). After bubbling nitrogen through the resulting solution for 5 min, Xantphos (179 mg, 0.31 mmol) and tris(dibenzylideneacetone)dipalladium(0) (283 mg, 0.31 mmol) were added. The reaction mixture was subjected to three cycles of vacuum/argon flush and heated at reflux for 10 h. After this time the reaction was cooled to room temperature and filtered. The filtrate was partitioned between ethyl acetate (50 mL) and water (10 mL). The aqueous layer was separated and extracted with ethyl acetate (3×20 mL). The combined organic layer was washed with brine (30 mL) and dried over sodium sulfate. The drying agent was removed by filtration and the filtrate was concentrated under reduced pressure. The residue was purified by silica-gel column chromatography eluting with 4:1 petroleum ether/ethyl acetate to afford 125c (1.21 g, 79%). LCMS: [M+H]$^+$ 492.1.

Example 125d

5-Bromo-3-(5-(2,2-dimethylpiperazin-1-yl)pyridin-2-ylamino)-1-methylpyridin-2(1H)-one 125d To the solution of 125c (1.19 g, 1.9 mmol) in dichloromethane (20 mL) was added 3M HCl in diethyl ether (15 mL). The reaction mixture was stirred at room temperature for 4 h. It was then concentrated under reduced pressure to afford 125d (900 mg, 95%). LCMS: [M+H]$^+$ 392.1.

Example 125e

5-Bromo-3-(5-(2,2-dimethyl-4-(oxetan-3-yl)piperazin-1-yl)pyridin-2-ylamino)-1-methylpyridin-2(1H)-one 125e A mixture of 125d (900 mg, 2.3 mmol), oxetan-3-one (497 mg, 6.9 mmol), NaBH$_3$CN (435 mg, 6.9 mmol), and zinc chloride (311 mg, 2.3 mmol) in methanol (30 mL) was stirred at 50° C. for 4 hours. It was then concentrated under reduced pressure. water (10 mL) was added to the residue and the mixture was extracted with CHCl₃ 3×50 mL). The combined organic layer was concentrated under reduced pressure. The residue was purified by silica-gel column-chromatography eluting with 50:1 dichloromethane/methanol to afford 125e (800 mg, 78%). LCMS: [M+H]⁺ 448.1. ¹H NMR (500 MHz, CDCl₃) δ 8.65 (d, J=2.0 Hz, 1H), 8.11 (d, J=2.5 Hz, 1H), 7.85 (s, 1H), 7.37-7.34 (m, 1H), 6.96 (d, J=2.5 Hz, 1H), 6.72 (d, J=8.5 Hz, 1H), 4.69-4.61 (m, 4H), 3.60 (s, 3H), 3.50-3.14 (m, 3H), 2.43-2.17 (m, 4H), 1.06 (s, 6H).

Example 125f 2-(5-(5-(2,2-Dimethyl-4-(oxetan-3-yl)piperazin-1-yl)pyridin-2-ylamino)-1-methyl-6-oxo-1,6-dihydropyridin-3-yl)-4-fluoro-6-(1-oxo-3,4,6,7,8,9-hexahydropyrazino[1,2-a]indol-2(1H)-yl)benzyl Acetate 125f

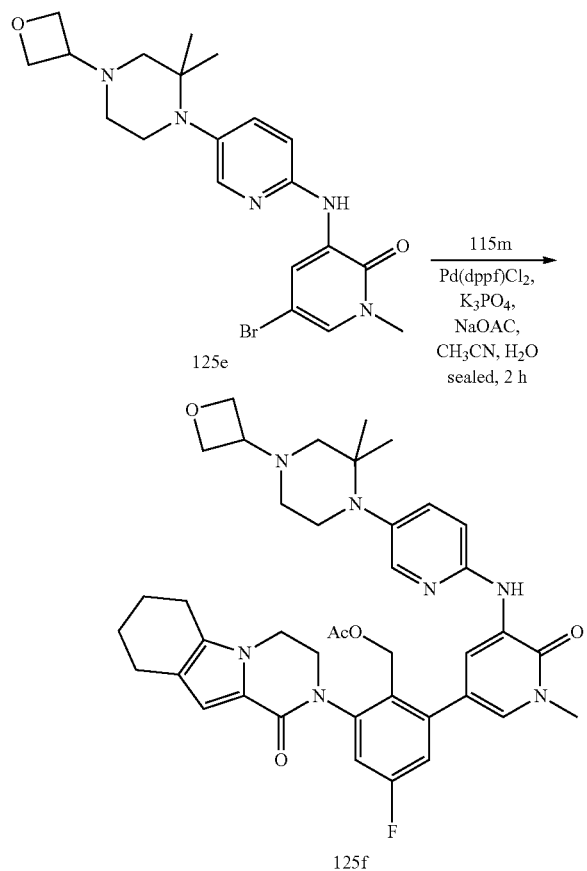

A 50-mL single-neck round-bottomed flask equipped with a magnetic stirrer and a reflux condenser was charged with 125e (190 mg, 1.0 eq., 0.42 mmol), 4-fluoro-2-(1-oxo-3,4,6,7,8,9-hexahydropyrazino[1,2-a]indol-2(1H)-yl)-6-(4,4,5,5-tetra-methyl-1,3,2-dioxaborolan-2-yl)benzyl acetate 115m (405 mg, 2.0 eq., 0.84 mmol), PdCl₂(dppf) (33 mg, 0.10 eq., 0.040 mmol), K₃PO₄ (178 mg, 2.0 eq., 0.84 mmol), sodium acetate (69 mg, 2.0 eq., 0.84 mmol), acetonitrile (20 mL), and water (0.1 mL). After three cycles of vacuum/argon flush, the mixture was heated at 90° C. for 2 h. It was then cooled to room temperature and filtered. The filtrate was concentrated under reduced pressure and the resulting residue was purified by silica-gel column chromatography eluting with 50:1 dichloromethane/ethanol to afford 125f (90 mg, 29%) as yellow solid. MS: [M+H]⁺ 724.3.

Example 125

2-(3-(5-(5-(2,2-dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one 125

A 50-mL single-neck round-bottomed flask equipped with a magnetic stirrer and was charged with 125f (85 mg, 1 eq., 0.11 mmol), lithium hydroxide (14 mg, 5 eq., 0.55 mmol), i-propanol (3 mL), THF (3 mL) and water (2 mL). The mixture was stirred at 30° C. for 1 h. It was then filtered and the residue was concentrated under reduced pressure. The residue was purified by reverse-phase prep-HPLC to afford 125 (43 mg, 57%). MS: [M+H]⁺ 682.4. ¹H NMR (500 MHz, DMSO) δ 8.62 (d, J=2.0 Hz, 1H), 8.55 (s, 1H), 7.94 (d, J=2.5 Hz, 1H), 7.41-7.39 (m, 2H), 7.33-7.31 (m, 1H), 7.23-7.17 (m, 2H), 6.52 (s, 1H), 4.86 (brs, 1H), 4.54 (t, J=6.5 Hz, 2H), 4.42 (t, J=6.0 Hz, 2H), 4.30 (s, 2H), 4.17-4.11 (m, 3H), 3.89-3.86 (m, 1H), 3.58 (m, 3H), 3.39-3.36 (m, 1H), 3.08-2.98 (m, 2H), 2.63-2.56 (m, 2H), 2.46 (t, J=6.0 Hz, 2H), 2.33-2.12 (m, 4H), 1.80-1.67 (m, 4H), 0.96 (s, 6H).

Example 126a 2-(5-(5-((2S,5R)-2,5-Dimethyl-4-(oxetan-3-yl)piperazin-1-yl)pyridin-2-ylamino)-1-methyl-6-oxo-1,6-dihydropyridin-3-yl)-4-fluoro-6-(1-oxo-3,4,6,7,8,9-hexahydropyrido[3,4-b]indolizin-2(1H)-yl)benzyl Acetate 126a

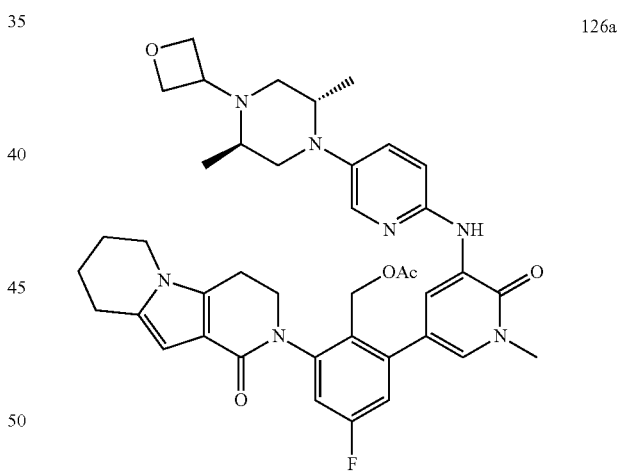

A 100-mL single-neck round-bottomed flask was charged with 2-bromo-4-fluoro-6-(1-oxo-3,4,6,7,8,9-hexahydropyrido[3,4-b]indolizin-2(1H)-yl)benzyl acetate 101h (347 mg, 0.80 mmol), 3-(5-((2S,5R)-2,5-dimethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 121g (792 mg, 1.6 mmol), Pd(dppf)Cl₂ (32.7 mg, 0.040 mmol), K₃PO₄ (340.0 mg, 1.6 mmol), sodium acetate trihydrate (217.6 mg, 1.6 mmol), water (0.5 mL), and acetonitrile (50 mL). The system was evacuated and refilled with N₂. The reaction mixture was heated at 100° C. for 2 h. It was then cooled to room temperature and filtered. The filtrate was concentrated under reduced pressure and the resulting residue was purified by silica-gel column chromatography eluting with 25:1 dichloromethane/methanol to afford 126a (200 mg, 34.6%) as a yellow brown solid. MS: [M+H]⁺ 724.5.

Example 126

2-[3-[5-[[5-[(2S,5R)-2,5-dimethyl-4-(oxetan-3-yl)piperazin-1-yl]-2-pyridyl]amino]-1-methyl-6-oxo-3-pyridyl]-5-fluoro-2-(hydroxymethyl)phenyl]-3,4,6,7,8,9-hexahydropyrido[3,4-b]indolizin-1-one 126

A mixture of 126a (150 mg, 0.20 mmol) and lithium hydroxide (72 mg, 3.0 mmol) in i-propanol/THF (5:3, 8.0 mL) and water (2.0 mL) was stirred at 30° C. for 1 h. The mixture was evaporated under reduced pressure and the residue was extracted with ethyl acetate (2×20 mL). The combined ethyl acetate extract was concentrated under reduced pressure and the residue was purified by prep-HPLC to afford 126 (45 mg, 33%) as a white solid. MS: [M+H]⁺ 682.9. ¹H NMR (500 MHz, CHCl₃) δ 8.60 (dd, J=2, 5 Hz, 1H), 8.03 (s, 1H), 7.87 (s, 1H), 7.54 (s, 1H), 7.37-7.35 (m, 1H), 7.14-7.12 (m, 1H), 6.96-6.94 (m, 1H), 6.82-6.80 (m, 1H), 6.31 (s, 1H), 4.77-4.71 (m, 2H), 4.67-4.62 (m, 2H), 4.58-4.55 (m, 1H), 4.41-4.40 (m, 1H), 4.29-4.25 (m, 1H), 4.13-4.09 (m, 1H), 3.91-3.80 (m, 3H), 3.77-3.74 (m, 1H), 3.70 (s, 3H), 3.18 (d, J=5.0 Hz, 1H), 3.06-3.01 (m, 1H), 2.98-2.90 (m, 2H), 2.83 (m, 2H), 2.77-2.70 (m, 2H), 2.47 (m, 1H), 2.06-2.01 (m, 2H), 1.97-1.93 (m, 1H), 1.88-1.87 (m, 2H), 0.91-0.89 (m, 6H).

Example 127a

Methyl 2-(Hydroxy(pyridin-2-yl)methyl)acrylate 127a

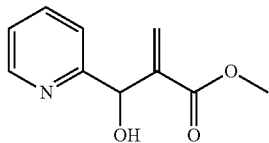

A 250-mL single-neck round-bottomed flask was charged with chloroform (100 mL), picolinaldehyde (10.7 g, 0.10 mol), methyl acrylate (8.60 g, 0.10 mol), and 1,4-diazabicyclo[2.2.2]octane (0.560 g, 5.00 mmol). The reaction mixture stirred at room temperature for 48 h. After this time the reaction was concentrated under reduced pressure and the residue was purified by silica-gel column chromatography eluting with 3:1 petroleum ether/ethyl acetate to afford 127a as a dark yellow oil (11.6 g, 60%). MS-ESI: (M+H)⁺ 194.2. ¹H NMR (500 MHz, CDCl₃) δ 8.54 (d, J=5.0 Hz, 1H), 7.69-7.66 (m, 1H), 7.42 (d, J=8.0 Hz, 1H), 7.22-7.20 (m, 1H), 6.36 (s, 1H), 5.97 (s, 1H), 5.62 (s, 1H), 4.85 (s, 1H), 3.74 (s, 3H).

Example 127b

Methyl Indolizine-2-carboxylate 127b

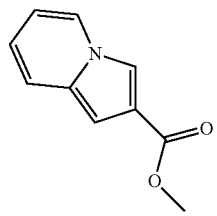

A 250-mL single-neck round-bottomed flask equipped with a magnetic stirrer and a reflux condenser was charged with acetic anhydride (80 mL) and 127a (6.68 g, 34.6 mmol). The reaction mixture was heated at reflux under nitrogen for 4 h. After this time the reaction was cooled to room temperature, poured onto the mixture of ice (100 g) and saturated aqueous sodium bicarbonate solution (200 mL), and stirred for 1 h. The resulting solution was neutralized with saturated aqueous sodium bicarbonate and extracted with methylene chloride (3×200 mL). The combined organic extract was dried over sodium sulfate and concentrated under reduced pressure. The residue was purified by silica-gel column chromatography eluting with 10:1 petroleum ether/ethyl acetate (10:1) to afford 127b as a white solid (2.1 g, 35%). MS-ESI: (M+H)⁺ 176.2. ¹H NMR (500 MHz, CDCl₃) δ 7.86-7.84 (m, 1H), 7.79 (d, J=1.0 Hz, 1H), 7.36-7.34 (m, 1H), 6.82 (s, 1H), 6.70-6.66 (m, 1H), 6.55-6.51 (m, 1H), 3.88 (s, 3H).

Example 127c

Methyl 5,6,7,8-Tetrahydroindolizine-2-carboxylate 127c

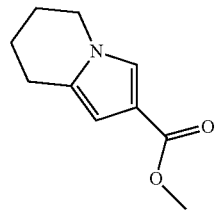

A 250-mL round-bottomed flask was purged with nitrogen and charged with 127b (2.0 g, 11.4 mmol), 10% palladium on carbon (50% wet, 200 mg), and methanol (50 mL). It was evacuated, charged with hydrogen gas, and stirred under 5 atm hydrogen at room temperature for 8 h. The hydrogen was then evacuated and nitrogen was charged into the flask. The catalyst was removed by filtration through a pad of CELITE® and the filtrate concentrated under reduced pressure to afford 127c as a white solid (1.1 g, 81%). MS-ESI: [M+H]⁺ 180.3. ¹H NMR (500 MHz, DMSO-d₆) δ 7.25 (d, J=2.0 Hz, 1H), 6.09 (s, 1H), 3.93 (t, J=6.0 Hz, 2H), 3.66 (s, 3H), 2.67 (t, J=6.0 Hz, 2H), 1.87-1.83 (m, 2H), 1.75-1.70 (m, 2H).

Example 127d

Methyl 3-Formyl-5,6,7,8-tetrahydroindolizine-2-carboxylate 127d

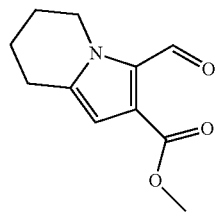

A 100-mL round-bottomed flask equipped with a magnetic stirrer was purged with nitrogen and charged with anhydrous dichloroethane (20 mL) and anhydrous DMF (0.70 mL, 9.0 mmol). To the mixture cooled at 0° C. was added phosphorus oxychloride (0.70 mL, 7.3 mmol) over a period of 2 min, while maintaining the reaction temperature between 0 and 10° C. The cooling bath was removed and the reaction was stirred at room temperature for 1 hour. A solution of methyl 5,6,7,8-tetrahydroindolizine-2-carboxylate (127c) (1.0 g, 5.6 mmol) in acetonitrile (10 mL) was added and the reaction mixture was stirred at room temperature for 3 hours. After this time, it was concentrated under reduced pressure. The oily residue was taken up with saturated aqueous NaHCO₃ (20 mL) and extracted with ethyl acetate (3×50 mL). The combined organic layer was washed with water (50 mL), dried over Na₂SO₄, and evaporated under reduced pressure. The residue was purified by silica-gel column chromatography eluting with 1:5 ethyl acetate/petroleum ether to afford 127d as a white solid (703 mg, 58%). MS-ESI: (M+H)⁺ 208.3. ¹H NMR (500 MHz, DMSO-d₆) δ 10.14 (s, 1H), 6.40 (s, 1H), 4.27 (t, J=6.0 Hz, 2H), 3.78 (s, 3H), 2.78 (t, J=6.0 Hz, 2H), 1.94-1.85 (m, 2H), 1.78-1.69 (m, 2H).

Example 127e 6,7,8,9-Tetrahydropyridazino[4,5-b]indolizin-1(2H)-one 127e

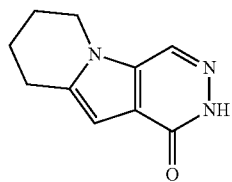 [SMILES: O=c1[nH]ncc2c1cc1n2CCCC1]

A 100-mL single-neck round-bottomed flask equipped with a reflux condenser was charged with methyl 3-formyl-5,6,7,8-tetrahydroindolizine-2-carboxylate (127d) (600 mg, 2.9 mmol) and hydrazinium hydroxide (20 mL). The reaction mixture was heated at 100° C. for 4 hours. After this time the reaction was cooled to room temperature and filtered to afford 127e as a yellow solid (413 mg, 75%). MS-ESI: (M+H)⁺ 190.1. ¹H NMR (500 MHz, DMSO-d₆) δ 12.17 (s, 1H), 8.24 (s, 1H), 6.33 (s, 1H), 4.16 (t, J=6.0 Hz, 2H), 2.88 (t, J=6.5 Hz, 2H), 2.00-1.96 (m, 2H), 1.84-1.79 (m, 2H).

Example 127f

2-Bromo-4-fluoro-6-(1-oxo-6,7,8,9-tetrahydropyridazino[4,5-b]indolizin-2(1H)-yl)benzaldehyde 127f

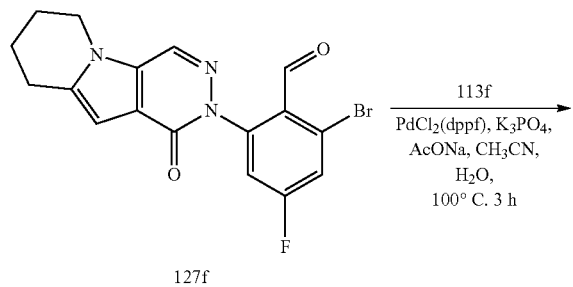

A 100-mL single-neck round-bottomed flask equipped with a magnetic stirrer and a reflux condenser was charged with 127e (450 mg, 2.4 mmol), 2,6-dibromo-4-fluorobenzaldehyde (2.0 g, 7.2 mmol), cesium carbonate (1.6 g, 4.8 mmol), and 1,4-dioxane (50 mL). After bubbling nitrogen through the resulting mixture for 10 minutes, copper(I) iodide (450 mg, 2.4 mmol) and 4,7-dimethoxy-1,10-phenanthroline (571 mg, 2.4 mmol) were added, and the reaction mixture was heated at 90° C. for 12 h. After this time the reaction was cooled to room temperature and filtered. The filtrate was partitioned between methylene chloride (40 mL) and water (40 mL). The aqueous layer was separated and extracted with methylene chloride (3×30 mL). The combined organic layer was washed with brine (50 mL) and dried over sodium sulfate. The drying agent was removed by filtration and the filtrate was concentrated under reduced pressure. The residue was purified by silica-gel column chromatography eluting with 1:2 ethyl acetate/petroleum ether to afford 127f as a brown solid (251 mg, 31%). MS-ESI: (M+H)⁺ 390.0.

Example 127g

4-Fluoro-2-(1-methyl-5-(5-(2-methyl-4-(oxetan-3-yl)piperazin-1-yl)pyridin-2-ylamino)-6-oxo-1,6-dihydropyridin-3-yl)-6-(1-oxo-6,7,8,9-tetrahydropyridazino[4,5-b]indolizin-2(1H)-yl)benzaldehyde 127g

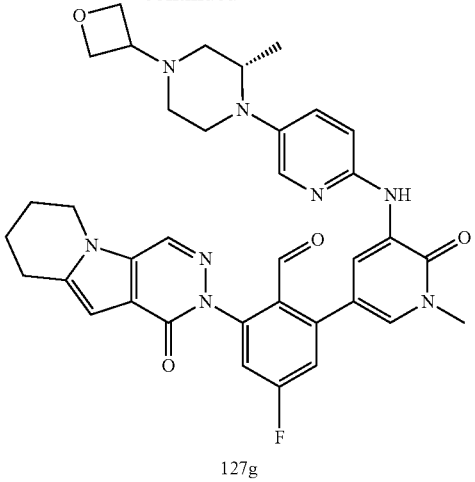

A 100-mL round-bottomed flask equipped with a magnetic stirrer and a reflux condenser was charged with 127f (125.0 mg, 0.32 mmol), 1-methyl-3-(5-(2-methyl-4-(oxetan-3-yl)piperazin-1-yl)pyridin-2-ylamino)-5-(4,4,5,5-tetra-methyl-1,3,2-dioxaborolan-2-yl)pyridin-2(1H)-one 113f (155.0 mg, 0.32 mmol), sodium acetate (53.0 mg, 0.64 mmol), K₃PO₄ (135.7.0 mg, 0.64 mmol), PdCl₂(dppf) (50.0 mg, 0.06 mmol), acetonitrile (25 mL), and water (1 mL). The system was subjected to 3 cycles of vacuum/argon flush and heated at 100° C. for 3 hours. It was then evaporated under reduced pressure and the residue was purified by silica-gel column chromatography eluting with 30:1 methylene chloride/methanol to afforded 127g compound (108 mg, 51%) as a brown solid. MS: [M+H]⁺ 665.4.

Example 127

2-[5-fluoro-2-(hydroxymethyl)-3-[1-methyl-5-[[5-[(2S)-2-methyl-4-(oxetan-3-yl)piperazin-1-yl]-2-pyridyl]amino]-6-oxo-3-pyridyl]phenyl]-6,7,8,9-tetrahydropyridazino[4,5-b]indolizin-1-one 127

A solution of 127g (100.0 mg, 0.15 mmol) in methanol (20 mL) was added NaBH₄ (17.0 mg, 0.45 mmol). The mixture was stirred at room temperature for 2 h. It was then quenched with water (1 mL) and the mixture was evaporated under reduced pressure. The residue was purified by reverse-phase prep-HPLC to afford 127 (56 mg, yield 56%) as a white solid. MS: [M+H]$^+$ 667.4. $^1$H NMR (500 MHz, DMSO-d$_6$) δ 8.58 (d, J=2.0, 1H), 8.47 (s, 1H), 8.40 (s, 1H), 7.85 (d, J=2.5, 1H), 7.39 (d, J=2.0, 1H), 7.37-7.34 (m, 1H), 7.30-7.28 (m, 1H), 7.25-7.22 (m, 2H), 6.48 (s, 1H), 4.57-4.53 (m, 2H), 4.46 (m, 2H), 4.41 (m, 1H), 4.25 (m, 2H), 4.20 (s, 2H), 3.69-3.64 (m, 1H), 3.58 (s, 3H), 3.41-3.36 (m, 1H), 3.10-3.07 (m, 1H), 2.96-2.92 (m, 3H), 2.54-2.50 (m, 1H), 2.35-2.28 (m, 2H), 2.18 (m, 1H), 2.04-2.00 (m, 2H), 1.87-1.82 (m, 2H), 0.92 (d, J=6.0, 3H).

Example 128a

2-Bromo-6-{4,4-dimethyl-9-oxo-1,10-diazatricyclo[6.4.0.0$^{2,6}$]dodeca-2(6),7-dien-10-yl}-4-fluorobenzaldehyde 128a

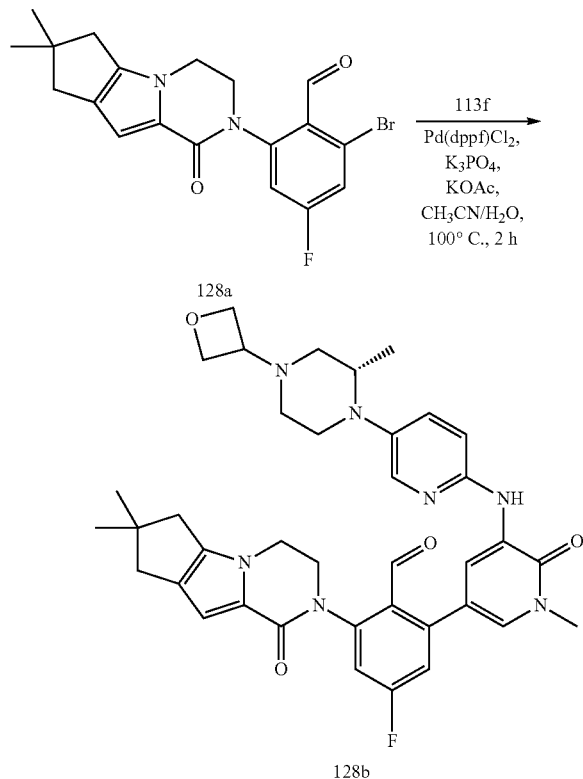

A 100-mL round-bottomed flask equipped with a reflux condenser was charged with 4,4-dimethyl-1,10-diazatricyclo[6.4.0.0$^{2,6}$]dodeca-2(6),7-dien-9-one 103e (1.0 g, 4.90 mmol, 1.0 eq.), 2-bromo-6-chloro-4-fluorobenzaldehyde (2.76 g, 9.8 mmol, 2.0 eq.), Pd$_2$(dba)$_3$ (224 mg, 0.24 mmol, 0.050 eq.), Xantphos (283 mg, 0.49 mmol, 0.10 eq.), potassium acetate (1.44 g, 14.7 mmol, 3.0 eq.), and 1,4-dioxane (50 mL). The system was evacuated and refilled with N$_2$. The reaction mixture was heated at 80° C. for 5 h. After this time the reaction was cooled to room temperature and filtered. The filtrate was concentrated under reduced pressure and the residue was purified on silica-gel column eluting with 80:1 dichloromethane/methanol to afford 128a as a yellow solid (992 mg, 50%). MS: [M+H]$^+$ 405.1

Example 128b

2-{4,4-Dimethyl-9-oxo-1,10-diazatricyclo[6.4.0.0$^{2,6}$]dodeca-2(6),7-dien-10-yl}-4-fluoro-6-[1-methyl-5-({5-[(2S)-2-methyl-4-(oxetan-3-yl)piperazin-1-yl]pyridin-2-yl}amino)-6-oxo-1,6-dihydropyridin-3-yl]benzaldehyde 128b A 50-mL round-bottomed flask equipped with a magnetic stirrer and a reflux condenser was charged with 128a (303 mg, 0.75 mmol), 1-methyl-3-({5-[(2S)-2-methyl-4-(oxetan-3-yl)piperazin-1-yl]pyridin-2-yl}amino)-5-(4,4,5,5-tetramethyl-1,3,2-dioxa-borolan-2-yl)-1,2-dihydropyridin-2-one 113f (385 mg, 0.80 mmol), Pd(dppf)Cl$_2$ (68.6 mg, 0.075 mmol), potassium acetate (147 mg, 1.50 mmol), K$_3$PO$_4$ (327 mg, 1.50 mmol), acetonitrile (15 mL), and water (6 drops). After three cycles of vacuum/argon flush, the mixture was heated at 100° C. for 2 h. After this time the reaction was cooled to room temperature. It was then filtered and the filtrate was evaporated under reduced pressure. The residue was purified by silica-gel column chromatography eluting with 15:1 ethyl acetate/methanol to afford 128b (382 mg, 77%) as a black solid. MS-ESI: [M+H]$^+$ 680.3

Example 128

2-(7,7-dimethyl-4-oxo-1,2,6,8-tetrahydrocyclopenta[3,4]pyrrolo[3,5-b]pyrazin-3-yl)-4-fluoro-6-[1-methyl-5-[[5-[(2S)-2-methyl-4-(oxetan-3-yl)piperazin-1-yl]-2-pyridyl]amino]-6-oxo-3-pyridyl]benzoic acid 128

To a mixture of 128b (190 mg, 0.28 mmol), tert-butyl alcohol (7 mL), and dichloromethane (0.5 mL) was added 2-methyl-2-butene (9.0 mL, 107 mmol). An aqueous solution (2 mL) of NaClO$_2$ (53 mg, 0.59 mmol) and NaH$_2$PO$_4$.2water (135.7 mg, 0.87 mmol) was added drop-wise at −10° C. The mixture was stirred at −10° C. for 1 h. It was then treated with water (20 mL) and extracted with ethyl acetate (4×50 mL). The combined organic extract was dried over MgSO$_4$, filtered, and evaporated under reduced pressure. The residue was purified with reverse-phase prep-HPLC to afford 128 (33 mg, 17%) as a pale yellow solid. MS-ESI: [M+H]$^+$ 696.2. $^1$H NMR (500 MHz, DMSO-d$_6$) δ 13.19-13.17 (m, 1H), 8.60 (s, 1H), 8.36 (s, 1H), 7.86 (d, J=2.5 Hz, 1H), 7.37-7.35 (m, 2H), 7.24-7.22 (m, 3H), 6.46 (s, 1H), 4.57-4.54 (m, 2H), 4.48-4.47 (m, 1H), 4.42-4.41 (m, 1H), 4.10-4.09 (m, 2H), 3.95-3.92 (m, 1H), 3.68-3.67 (m, 1H), 3.56 (s, 3H), 3.42-3.39 (m, 2H), 3.09-3.07 (m, 1H), 2.96-2.94 (m, 1H), 2.92 (s, 3H), 2.41-2.40 (m, 2H), 2.35-2.31 (m, 2H), 2.20-2.17 (m, 1H), 1.21-1.20 (m, 6H), 0.93 (d, J=6.5 Hz, 3H).

Example 129a

2-Bromo-6-{4,4-dimethyl-9-oxo-1,10-diazatricyclo[6.4.0.0$^{2,6}$]dodeca-2(6),7-dien-10-yl}-4-fluorobenzoic Acid 129a

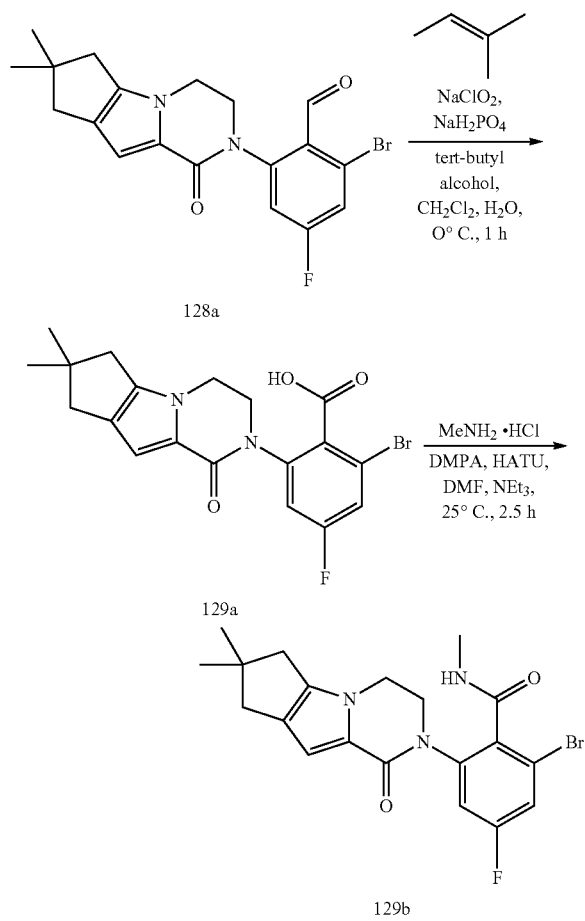

To a mixture of 2-bromo-6-{4,4-dimethyl-9-oxo-1,10-diazatricyclo[6.4.0.0$^{2,6}$]dodeca-2(6),7-dien-10-yl}-4-fluorobenzaldehyde 128a (810 mg, 2.0 mmol), tert-butyl alcohol (50 mL), and dichloromethane (3 mL) was added 2-methyl-2-butene (22 mL, 262 mmol). An aqueous solution (20 mL) of NaClO$_2$ (1.8 g, 20.0 mmol) and NaH$_2$PO$_4$ dihydrate (2.2 g, 14.0 mmol) was added dropwise at 0° C. The mixture was stirred at 0° C. for 1 h. It was then treated with water (30 mL) and extracted with ethyl acetate (4×90 mL). The combined organic extract was dried over MgSO$_4$ and concentrated under reduced pressure to afford 129a (930 mg, 84%) as a yellow solid. MS-ESI: [M+H]$^+$ 421.1

Example 129b

2-Bromo-6-{4,4-dimethyl-9-oxo-1,10-diazatricyclo[6.4.0.0$^{2,6}$]dodeca-2(6), 7-dien-10-yl}-4-fluoro-N-methylbenzamide 129b A 25-mL single-neck round-bottomed flask equipped with a magnetic stirrer was charged with DMF (8 mL), 129a (160 mg, 0.38 mmol), HATU (505 mg, 1.33 mmol), DMAP (46 mg, 0.38 mmol), and triethylamine (1.0 mL). The mixture was heated at 25° C. for 0.5 h. Then MeNH$_2$.HCl (266 mg, 3.8 mmol) was added and resulting mixture was stirred at 25° C. for 2.5 h. After this time the reaction was cooled to room temperature. It was then filtered and the filtrate was evaporated under reduced pressure. The residue was purified by prep-TLC developing with 1:20 methanol/dichloromethane to afford 129b (116 mg, 70%) as a black solid. MS-ESI: [M+H]$^+$ 434.0

Example 129

2-(7,7-dimethyl-4-oxo-1,2,6,8-tetrahydrocyclopenta[3,4]pyrrolo[3,5-b]pyrazin-3-yl)-4-fluoro-N-methyl-6-[1-methyl-5-[[5-[(2S)-2-methyl-4-(oxetan-3-yl)piperazin-1-yl]-2-pyridyl]amino]-6-oxo-3-pyridyl]benzamide 129

A 25-mL single-neck round-bottomed flask equipped with a magnetic stirrer and a reflux condenser was charged with 129b (116 mg, 0.27 mmol), 1-methyl-3-({5-[(2S)-2-methyl-4-(oxetan-3-yl)piperazin-1-yl]pyridin-2-yl}amino)-5-(4,4,5,5-tetramethyl-1,3,2-dioxaborolan-2-yl)-1,2-dihydropyridin-2-one 113f (260 mg, 0.54 mmol), Pd(dppf)Cl$_2$ (26 mg, 0.030 mmol), potassium acetate (53 mg, 0.54 mmol), K$_3$PO$_4$ (117 mg, 0.54 mmol), acetonitrile (5 mL), and water (0.50 mL). After three cycles of vacuum/argon flush, the mixture was heated at reflux for 2 h. After this time the reaction was cooled to room temperature. It was then filtered and the filtrate was evaporated under reduced pressure. The residue was purified with reverse-phase prep-HPLC to afford 129 (80 mg, 42%) as a pale yellow solid. MS-ESI: [M+H]$^+$ 709.5. $^1$H NMR (500 MHz, DMSO-d$_6$) δ 8.69 (d, J=2.0 Hz, 1H), 8.39 (s, 1H), 8.11 (d, J=4.5 Hz, 1H), 7.89 (d, J=2.5 Hz, 1H), 7.38-7.36 (m, 1H), 7.32-7.30 (m, 2H), 7.28-7.26 (m, 1H), 7.23-7.21 (m, 1H), 6.47 (s, 1H), 4.58-4.54 (m, 2H), 4.48-4.46 (m, 1H), 4.43-4.41 (m, 1H), 4.05-3.91 (m, 4H), 3.67-3.66 (m, 1H), 3.57 (s, 3H), 3.41-3.38 (m, 1H), 3.10-3.08 (m, 1H), 2.97-2.94 (m, 1H), 2.55-2.54 (m, 3H), 2.48-2.47 (m, 3H), 2.40-2.39 (m, 2H), 2.36-2.28 (m, 2H), 2.22-2.19 (m, 1H), 1.21-1.20 (m, 6H), 0.93 (d, J=6.5 Hz, 3H).

Example 130a

2-Bromo-6-{6-oxo-8-thia-4,5-diazatricyclo[7.4.0.0$^{2,7}$]trideca-1(9),2(7),3-trien-5-yl}benzaldehyde 130a A 25-mL single-neck round-bottomed flask equipped with a magnetic stirrer and a reflux condenser was charged with 1,4-dioxane (20 mL), 8-thia-4,5-diazatricyclo[7.4.0.0$^{2,7}$]trideca-1(9),2(7),3-trien-6-one 117c (618 mg, 3.0 mmol), 2,6-dibromobenzaldehyde (1980 mg, 7.5 mmol), CuBr (215 mg, 1.5 mmol), sarcosine (267 mg, 3.0 mmol), and K$_2$CO$_3$ (828 mg, 6.0 mmol). After three cycles of vacuum/argon flush, the mixture was heated at 100° C. for 16 h. After this time the reaction was cooled to room temperature. It was then filtered and the filtrate was evaporated under reduced pressure. The residue was purified by silica-gel column chromatography eluting with 30:1 dichloromethane/methanol to afford 130a (702 mg, 60%) as a yellow solid. MS: [M+H]$^+$ 389.0

Example 130b

2-[1-Methyl-5-({5-[(2S)-2-methyl-4-(oxetan-3-yl)piperazin-1-yl]pyridin-2-yl}amino)-6-oxopyridin-3-yl]-6-{6-oxo-8-thia-4,5-diazatricyclo[7.4.0.0$^{2,7}$]trideca-1(9),2(7),3-trien-5-yl}benzaldehyde 130b

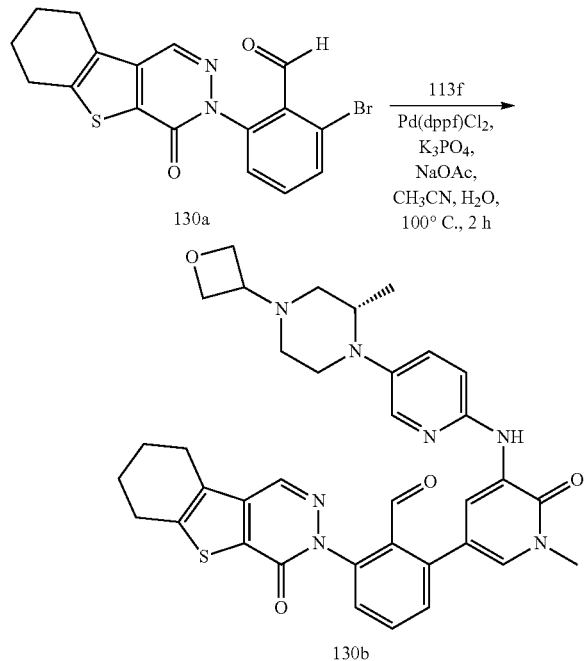

A sealed tube equipped with a magnetic stirrer was charged with 130a (160 mg, 0.40 mmol), (S)-1-methyl-5-(5-(2-methyl-4-(oxetan-3-yl)piperazin-1-yl)pyridin-2-ylamino)-6-oxo-1,6-dihydropyridin-3-ylboronic acid 113f (160 mg, 0.40 mmol), Pd(dppf)Cl$_2$ (32 mg, 0.040 mmol), sodium acetate (66 mg, 0.80 mmol), K$_3$PO$_4$ (170 mg, 0.80 mmol), and acetonitrile (6 mL). After three cycles of vacuum/argon flush, the mixture was heated at 100° C. for 2 h. It was then filtered and the filtrate was evaporated under reduced pressure. The residue was purified by silica-gel column chromatography eluting with 30:1 dichloromethane/methanol to afford 130b (123 mg, 46%) as a yellow solid. LCMS: [M+H]$^+$ 664.3

Example 130

3-[2-(hydroxymethyl)-3-[1-methyl-5-[[5-[(2S)-2-methyl-4-(oxetan-3-yl)piperazin-1-yl]-2-pyridyl]amino]-6-oxo-3-pyridyl]phenyl]-6,7,8,9-tetrahydrobenzothiopheno[2,3-d]pyridazin-4-one 130

At 0° C., to a solution of 130b (120 mg, 0.18 mmol) in methanol (5 mL) was added sodium borohydride (20 mg, 0.54 mmol). The reaction was stirred for 30 minutes. It was then quenched with water (1 mL) and concentrated under reduced pressure. The residue was purified by reverse-phase prep-HPLC to afford 130 (70 mg, 59%). LCMS: [M+H]$^+$ 666.3. $^1$H NMR (500 MHz, CDCl$_3$) δ 8.62 (d, J=2.0 Hz, 1H), 8.26 (s, 1H), 7.98 (s, 1H), 7.84 (s, 1H), 7.56-7.54 (m, 2H), 7.42 (d, J=2.5 Hz, 1H), 7.37 (dd, J=2.0, 7.0 Hz, 1H), 7.31 (d, J=8.0 Hz, 1H), 6.83 (d, J=8.5 Hz, 1H), 4.72-4.66 (m, 4H), 4.36 (d, J=5.0 Hz, 2H), 4.05 (t, J=5.5 Hz, 1H), 3.72 (s, 3H), 3.55-3.54 (m, 1H), 3.46-3.45 (m, 1H), 3.08-3.06 (m, 2H), 2.99 (t, J=5.0 Hz, 2H), 2.87 (t, J=5.0 Hz, 2H), 2.60-2.59 (m, 1H), 2.49-2.48 (m, 2H), 2.20-2.19 (m, 1H), 2.02-1.96 (m, 4H), 0.99 (d, J=6.0 Hz, 3H).

Example 131a 3,3-Dimethylcyclopentanone 131a

Figure 15:
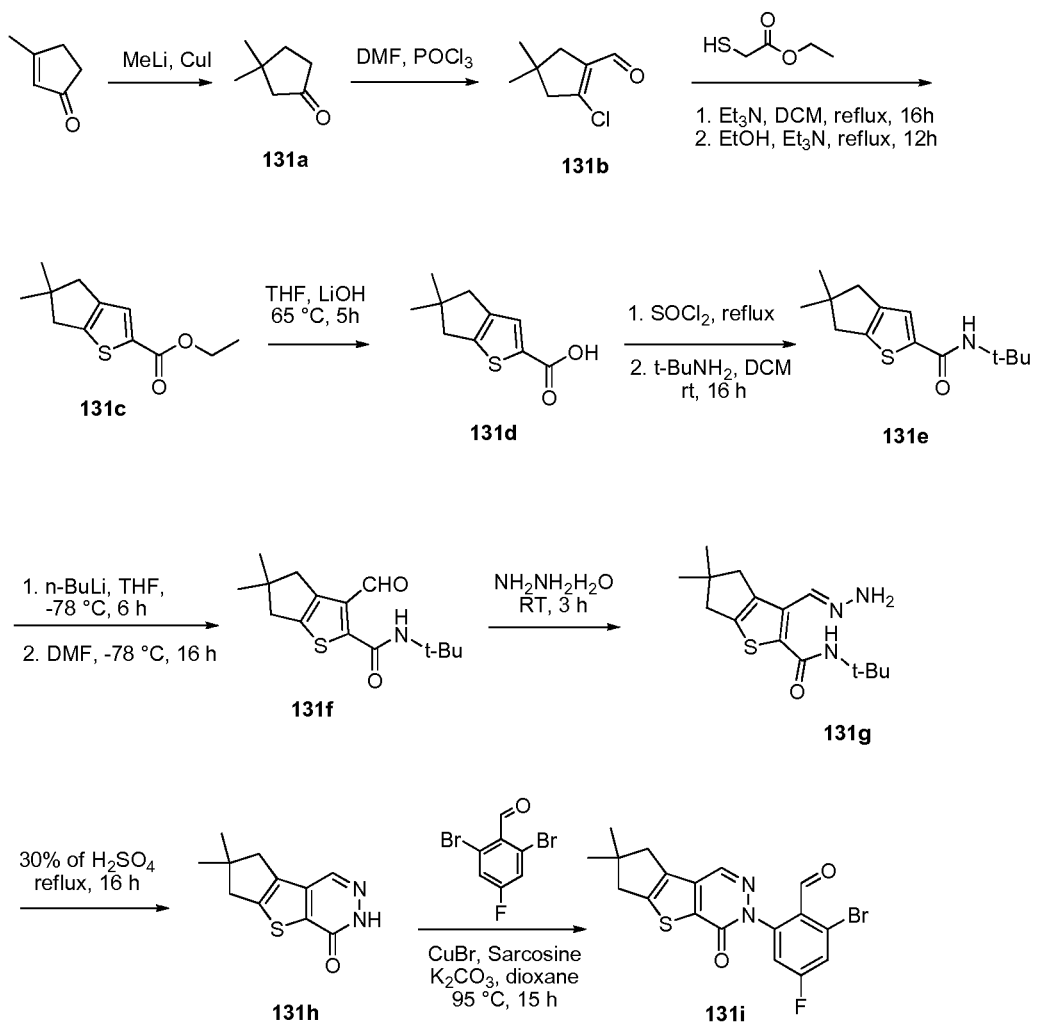
FIG. 15 shows the preparation of 2-Bromo-6-{4,4-dimethyl-9-oxo-7-thia-10,11-diazatricyclo[6.4.0.0$^{2,6}$]dodeca-1(8),2(6), 11-trien-10-yl}-4-fluorobenzaldehyde 131i from intermediate 3-methylcyclopent-2-enone.

To a suspension of CuI (81.0 g, 420 mmol) in anhydrous ethyl ether (500 mL) cooled to 0° C. was added a solution of methyllithium in ethyl ether (430 mL, 860 mmol, 2.0M) over a period of 30 minutes. See FIG. 15. The mixture was stirred at 0° C. for 2 h. To the above mixture was added 3-methylcyclopent-2-enone (33.6 g, 350 mmol) dropwise over a period of 1 h at 0° C. The resulting mixture was stirred at 0° C. for another 2 h. It was then quenched with saturated NH$_4$Cl (300 mL) and filtered. The filtrate was extracted with ethyl ether (2×200 mL). The combined organic layer was dried over anhydrous Mg$_2$SO$_4$ and filtered. The filtrate was evaporated under reduced pressure to afford 131a as a colorless oil (28 g, 71%). $^1$H NMR (500 MHz, DMSO-d$_6$) δ 2.31 (t, J=8.0 Hz, 2H), 2.05 (s, 2H), 1.79 (t, J=8.0 Hz, 2H), 1.12 (s, 6H).

Example 131b

2-Chloro-4,4-dimethylcyclopent-1-enecarbaldehyde 131b

To a solution of DMF (18.3 g, 250 mmol) in dichloromethane (300 mL) cooled at 0° C. was added POCl$_3$ (40.5 g, 250 mmol) over a period of 10 minutes. See FIG. 15. The mixture was stirred at 20° C. for 1 h. To the above mixture was added 131a (28.0 g, 250 mmol) dropwise over a period of 20 minutes. The resulting mixture was heated at reflux for 20 h. The reaction mixture was cooled to room temperature and poured into a solution of sodium acetate (60 g) in ice-water (400 g). The mixture was extracted with dichloromethane (2×300 mL). The combined organic layer was washed with water (2×200 mL), dried over anhydrous Mg$_2$SO$_4$ and filtered. The filtrate was evaporated under reduced pressure to afford 131b as a colorless oil (33.0 g, crude). $^1$H NMR (500 MHz, DMSO-d$_6$) δ 9.99 (s, 1H), 2.62 (d, J=2.0 Hz, 2H), 2.38 (d, J=2.0 Hz, 2H), 1.15 (s, 6H).

Example 131c

Ethyl 5,5-Dimethyl-5,6-dihydro-4H-cyclopenta[b]thiophene-2-carboxylate 131c

To a solution of 131b (33.0 g, crude) in dichloromethane (400 mL) and triethylamine (60 g, 600 mmol) was added ethyl 2-mercaptoacetate (19.2 g, 160 mmol). See FIG. 15. The reaction mixture was heated at reflux for 6 h. It was then concentrated under reduced pressure. The residue was dissolved in ethanol (400 mL) and triethylamine (60 g, 600 mmol). The mixture was heated at reflux for 12 h. It was concentrated again under reduced pressure and the residue was purified by silica-gel column chromatography eluting with 40:1 petroleum ether/ethyl acetate to 131c as a yellow solid (18.0 g, 32%, over two steps). MS-ESI: [M+H]$^+$ 225.3. $^1$H NMR (500 MHz, DMSO-d$_6$) δ 7.49 (s, 1H), 4.32 (q, J=7.0 Hz, 2H), 2.72 (s, 2H), 2.56 (s, 2H), 1.35 (t, J=7.0 Hz, 3H), 1.22 (s, 6H).

Example 131d

5,5-Dimethyl-5,6-dihydro-4H-cyclopenta[b]thiophene-2-carboxylic Acid 131d

To a solution of 131c (16.0 g, 71.0 mmol) in propan-2-ol (200 mL), tetrahydrofuran (200 mL), and water (200 mL) was added lithium hydroxide (6.82 g, 284 mmol). See FIG. 15. The reaction mixture was heated at 65° C. for 5 h. The organic solvents were removed under reduced pressure. The pH of the residue was adjusted to 1.0 with hydrochloride acid (12M). The precipitate was collected by filtration and dried in vacuo to afford 131d (12.0 g, 86%) as a white solid. MS-ESI: [M+H]$^+$ 196.9

Example 131e

N-tert-Butyl-5,5-dimethyl-5,6-dihydro-4H-cyclopenta[b]thiophene-2-carboxamide 131e

A suspension of 131d (12.0 g, 61.0 mmol) in SOCl$_2$ (80 mL) was heated at 65° C. for 2 h. The reaction mixture was concentrated under reduced pressure. See FIG. 15. The residue was diluted with dichloromethane (20 mL), which was added to the solution of 2-methylpropan-2-amine (4.45 g, 61.0 mmol) and triethylamine (18.0 g, 180 mmol) in dichloromethane (180 mL). The resulting mixture was stirred for 16 h and diluted with dichloromethane (200 mL). It was washed with water (3×50 mL), dried over anhydrous Mg$_2$SO$_4$, filtered, and evaporated under reduced pressure to afford 131e (15.0 g, 97%) as a yellow solid. MS-ESI: [M+H]$^+$ 252.0

Example 131f

N-tert-Butyl-3-formyl-5,5-dimethyl-5,6-dihydro-4H-cyclopenta[b]thiophene-2-carboxamide 131f

To a solution of 131e (1.5 g, 6.0 mmol) in anhydrous THF (60 mL) cooled to −70° C. was added the solution of n-butyllithium (10.0 mL, 25 mmol, 2.5 M in hexane) over a period of five minutes. See FIG. 15. It was stirred at −70° C. for 6 h. DMF (1.3 g, 18.0 mmol) was added over a period of five minutes and the result mixture was stirred at room temperature overnight. It was then quenched with saturated NH$_4$Cl (40 mL) and concentrated under reduced pressure. The residue was extracted with ethyl acetate (2×30 mL). The combined organic layer was dried over anhydrous Mg$_2$SO$_4$ and filtered. The filtrate was evaporated under reduced pressure to afford 131f as a yellow solid (1.34 g, 80%). MS-ESI: [M+H]$^+$ 280.3

Example 131g

N-tert-Butyl-3-(hydrazonomethyl)-5,5-dimethyl-5,6-dihydro-4H-cyclopenta[b]thiophene-2-carboxamide 131g

To a solution of 85% aqueous hydrazine (10 mL) in THF (180 mL) was added 131f (5.6 g, 20.0 mmol) in anhydrous THF (20 mL) over a period of 5 minutes. See FIG. 15. It was stirred at 20° C. for 3 h. The reaction mixture was concentrated under reduced pressure to afford 131g as a black solid (6.0 g, yield: 95%, purity: 95%). MS-ESI: [M+H]$^+$ 294.0

Example 131h

4,4-Dimethyl-7-thia-10,11-diazatricyclo[6.4.0.0$^{2,6}$]dodeca-1(8),2(6),11-trien-9-one 131h

A solution of 131g (3.8 g, 13.0 mmol) in 30% H$_2$SO$_4$ (100 mL) was heated at reflux for 16 h. See FIG. 15. The reaction mixture was cooled to room temperature and extracted with dichloromethane (3×200 mL). The combined organic layer was concentrated under reduced pressure and the residue was purified by silica-gel column chromatography eluting with 100:1 dichloromethane/methanol to afford 131h as a yellow solid (1.72 g, 60%). MS-ESI: [M+H]$^+$ 221.0

Example 131i

2-Bromo-6-{4,4-dimethyl-9-oxo-7-thia-10,11-diazatricyclo[6.4.0.0$^{2,6}$]dodeca-1(8),2(6),11-trien-10-yl}-4-fluorobenzaldehyde 131i

A 100-mL round bottom flask equipped with a magnetic stirrer and a reflux condenser was charged with 131h (330 mg, 1.5 mmol), 2,6-dibromo-4-fluorobenzaldehyde (1.26 g, 4.5 mmol), CuBr (113 mg, 0.8 mmol), sarcosine (142 mg, 1.6 mmol), K$_2$CO$_3$ (420 mg, 3.0 mmol), and dioxane (20 mL). See FIG. 15. After three cycles of vacuum/argon flush, the mixture was heated at 95° C. for 15 h. It was then cooled to room temperature and filtered. The filtrate was concentrated under reduced pressure and the resulting residue was purified by silica-gel column chromatography 5:1 eluting with petroleum ether/ethyl acetate to 131i as a white solid (380 mg, 60%). MS-ESI: [M+H]$^+$ 420.6

Example 131j

2-{4,4-Dimethyl-9-oxo-7-thia-10,11-diazatricyclo[6.4.0.0$^{2,6}$]dodeca-1(8),2(6),11-trien-10-yl}-4-fluoro-6-[1-methyl-5-({5-[(2S)-2-methyl-4-(oxetan-3-yl)piperazin-1-yl]pyridin-2-yl}amino)-6-oxo-1,6-dihydropyridin-3-yl]benzaldehyde 131j

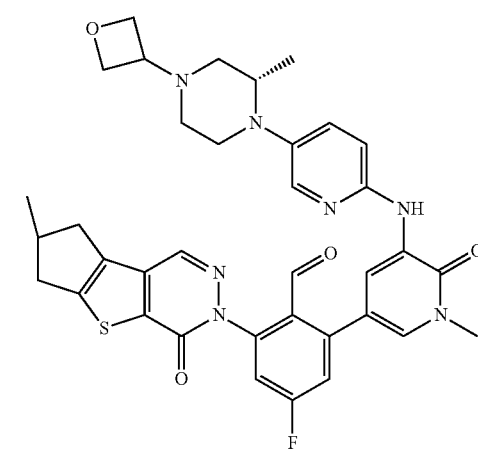

131j

A 50-mL round bottom flask equipped with a magnetic stirrer and a reflux condenser was charged with 131i (421 mg, 1.0 mmol), (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 113f (580 mg, 1.2 mmol), Pd(dppf)Cl$_2$ (59 mg, 0.080 mmol), K$_3$PO$_4$.trihydrate (360 mg, 1.6 mmol), water (6 drops), and tetrahydrofuran (20 mL). After three cycles of vacuum/argon flush, the mixture was heated at reflux for 6 h. It was then cooled to room temperature and filtered. The filtrate was concentrated under reduced pressure and the residue was washed with 1:1 petroleum ether/ethyl acetate (20 mL) to afford 131j as a white solid (556 mg, 80%). MS-ESI: [M+H]$^+$ 696.3

Example 131

3-[5-fluoro-2-(hydroxymethyl)-3-[1-methyl-5-[[5-[(2S)-2-methyl-4-(oxetan-3-yl)piperazin-1-yl]-2-pyridyl]amino]-6-oxo-3-pyridyl]phenyl]-7,7-dimethyl-6,8-dihydrocyclopenta[3,4]thieno[1,3-d]pyridazin-4-one 131

To a solution of 131j (520 mg, 0.75 mmol) in methanol (10 mL) was added sodium borohydride (110 mg, 3.0 mmol) at 20° C. The reaction mixture was stirred for 30 minutes and quenched with water (3 mL). It was then concentrated under reduced pressure and the residue was purified with reverse phase prep-HPLC to afford 131 (340 mg, 65%). MS-ESI: [M+H]$^+$ 698.3. $^1$H NMR (500 MHz, DMSO-d$_6$) δ 8.55 (d, J=2.5 Hz, 1H), 8.46 (s, 1H), 8.41 (s, 1H), 7.85 (d, J=2.5 Hz, 1H), 7.40-7.30 (m, 4H), 7.23 (d, J=9.0 Hz, 1H), 4.60 (t, J=5.0 Hz, 1H), 4.57-4.53 (m, 2H), 4.46 (t, J=6.0 Hz, 1H), 4.41 (t, J=6.0 Hz, 1H), 4.30-4.29 (m, 2H), 3.68-3.65 (m, 1H), 3.58 (s, 3H), 3.40-3.38 (m, 1H), 3.10-3.07 (m, 1H), 2.95-2.94 (m, 1H), 2.91-2.89 (m, 2H), 2.80-2.78 (m, 2H), 2.54-2.52 (m, 1H), 2.34-2.30 (m, 2H), 2.20-2.16 (m, 1H), 1.27 (s, 6H), 0.93 (d, J=6.5 Hz, 3H).

Example 901

Biochemical Btk Assay

A generalized procedure for a standard biochemical Btk Kinase Assay that can be used to test Formula I compounds is as follows. A master mix minus Btk enzyme is prepared containing 1× Cell Signaling kinase buffer (25 mM Tris-HCl, pH 7.5, 5 mM beta-glycerophosphate, 2 mM dithiothreitol, 0.1 mM Na$_3$VO$_4$, 10 mM MgCl$_2$), 0.5 µM Promega PTK Biotinylated peptide substrate 2, and 0.01% BSA. A master mix plus Btk enzyme is prepared containing 1× Cell Signaling kinase buffer, 0.5 µM PTK Biotinylated peptide substrate 2, 0.01% BSA, and 100 ng/well (0.06 mU/well) Btk enzyme. Btk enzyme is prepared as follows: full length human wild-type Btk (accession number NM-000061) with a C-terminal V5 and 6× His tag was subcloned into pFastBac vector for making baculovirus carrying this epitope-tagged Btk. Generation of baculovirus is done based on Invitrogen's instructions detailed in its published protocol "Bac-to-Bac Baculovirus Expression Systems" (Cat. Nos. 10359-016 and 10608-016). Passage 3 virus is used to infect Sf9 cells to overexpress the recombinant Btk protein. The Btk protein is then purified to homogeneity using Ni-NTA column. The purity of the final protein preparation is greater than 95% based on the sensitive Sypro-Ruby staining A solution of 200 µM ATP is prepared in water and adjusted to pH7.4 with 1N NaOH. A quantity of 1.25 µL of compounds in 5% DMSO is transferred to a 96-well ½ area Costar polystyrene plate. Compounds are tested singly and with an 11-point dose-responsive curve (starting concentration is 10 µM; 1:2 dilution). A quantity of 18.75 µL of master mix minus enzyme (as a negative control) and master mix plus enzyme is transferred to appropriate wells in 96-well ½ area costar polystyrene plate. 5 µL of 200 µM ATP is added to that mixture in the 96-well ½ area Costar polystyrene plate for final ATP concentration of 40 µM. The reaction is allowed to incubate for 1 hour at room temperature. The reaction is stopped with Perkin Elmer 1× detection buffer containing 30 mM EDTA, 20 nM SA-APC, and 1 nM PT66 Ab. The plate is read using time-resolved fluorescence with a Perkin Elmer Envision using excitation filter 330 nm, emission filter 665 nm, and 2$^{nd}$ emission filter 615 nm. IC$_{50}$ values are subsequently calculated. Alternatively, the Lanthascreen assay can be used to evaluate Btk activity through quantification of its phosphorylated peptide product. The FRET (Fluorescence Resonance Energy Transfer) that occurs between the fluorescein on the peptide product and the terbium on the detection antibody decreases with the addition of inhibitors of Btk that reduce the phosphorylation of the peptide. In a final reaction volume of 25 µL, Btk (h) (0.1 ng/25 ul reaction) is incubated with 50 mM Hepes pH 7.5, 10 mM MgCl2, 2 mM MnCl$_2$, 2 mM DTT, 0.2 mM NaVO4, 0.01% BSA, and 0.4 uM fluorescein poly-GAT. The reaction is initiated by the addition of ATP to 25 uM (Km of ATP). After incubation for 60 minutes at room temperature, the reaction is stopped by the addition of a final concentration of 2 nM Tb-PY20 detection antibody in 60 mM EDTA for 30 minutes at room temperature. Detection is determined on a Perkin Elmer Envision with 340 nM excitation and emission at 495 nm and 520 nm. Exemplary Btk inhibition IC50 values are in Tables 1, 2, and 3.

Example 902

Ramos Cell Btk Assay

Another generalized procedure for a standard cellular Btk Kinase Assay that can be used to test Formula I compounds is as follows. Ramos cells are incubated at a density of 0.5×10$^7$ cells/ml in the presence of test compound for 1 hr at 37° C. Cells are then stimulated by incubating with 10 µg/ml anti-human IgM F(ab)$_2$ for 5 minutes at 37° C. Cells are pelleted, lysed, and a protein assay is performed on the cleared lysate. Equal protein amounts of each sample are subject to SDS-PAGE and western blotting with either anti-phosphoBtk (Tyr223) antibody (Cell Signaling Technology #3531; Epitomics, cat. #2207-1) or phosphoBtk(Tyr551) antibody (BD Transduction Labs #558034) to assess Btk autophosphorylation or an anti-Btk antibody (BD Transduction Labs #611116) to control for total amounts of Btk in each lysate.

Example 903

B-Cell Proliferation Assay

A generalized procedure for a standard cellular B-cell proliferation assay that can be used to test Formula I compounds is as follows. B-cells are purified from spleens of 8-16 week old Balb/c mice using a B-cell isolation kit (Miltenyi Biotech, Cat #130-090-862). Testing compounds are diluted in 0.25% DMSO and incubated with 2.5×10$^5$ purified mouse splenic B-cells for 30 min prior to addition of 10 µg/ml of an anti-mouse IgM antibody (Southern Biotechnology Associates Cat #1022-01) in a final volume of 100 µl. Following 24 hr incubation, 1 µCi $^3$H-thymidine is added and plates are incubated an additional 36 hr prior to harvest using the manufacturer's protocol for SPA[$^3$H] thymidine uptake assay system (Amersham Biosciences #RPNQ 0130). SPA-bead based fluorescence is counted in a microbeta counter (Wallace Triplex 1450, Perkin Elmer).

Example 904

T Cell Proliferation Assay

A generalized procedure for a standard T cell proliferation assay that can be used to test Formula I compounds is as follows. T cells are purified from spleens of 8-16 week old Balb/c mice using a Pan T cell isolation kit (Miltenyi Biotech, Cat #130-090-861). Testing compounds are diluted in 0.25% DMSO and incubated with $2.5 \times 10^5$ purified mouse splenic T cells in a final volume of 100 µl in flat clear bottom plates precoated for 90 min at 37° C. with 10 µg/ml each of anti-CD3 (BD #553057) and anti-CD28 (BD #553294) antibodies. Following 24 hr incubation, 1 µCi $^3$H-thymidine is added and plates incubated an additional 36 hr prior to harvest using the manufacturer's protocol for SPA[$^3$H] thymidine uptake assay system (Amersham Biosciences # RPNQ 0130). SPA-bead based fluorescence was counted in a microbeta counter (Wallace Triplex 1450, Perkin Elmer).

Example 905

CD86 Inhibition Assay

A generalized procedure for a standard assay for the inhibition of B cell activity that can be used to test Formula I compounds is as follows. Total mouse splenocytes are purified from spleens of 8-16 week old Balb/c mice by red blood cell lysis (BD Pharmingen #555899). Testing compounds are diluted to 0.5% DMSO and incubated with $1.25 \times 10^6$ splenocytes in a final volume of 200 µl in flat clear bottom plates (Falcon 353072) for 60 min at 37° C. Cells are then stimulated with the addition of 15 µg/ml IgM (Jackson ImmunoResearch 115-006-020), and incubated for 24 hr at 37° C., 5% $CO_2$. Following the 24 hr incubation, cells are transferred to conical bottom clear 96-well plates and pelleted by centrifugation at $1200 \times g \times 5$ min. Cells are preblocked by CD16/CD32 (BD Pharmingen #553142), followed by triple staining with CD19-FITC (BD Pharmingen #553785), CD86-PE (BD Pharmingen #553692), and 7AAD (BD Pharmingen #51-68981E). Cells are sorted on a BD FACSCalibur and gated on the CD19$^+$/7AAD$^-$ population. The levels of CD86 surface expression on the gated population is measured versus test compound concentration.

Example 906

B-ALL Cell Survival Assay

The following is a procedure for a standard B-ALL (acute lymphoblastic leukemia) cell survival study using an XTT readout to measure the number of viable cells. This assay can be used to test Formula I compounds for their ability to inhibit the survival of B-ALL cells in culture. One human B-cell acute lymphoblastic leukemia line that can be used is SUP-B15, a human Pre-B-cell ALL line that is available from the ATCC.

SUP-B15 pre-B-ALL cells are plated in multiple 96-well microtiter plates in 100 µl of Iscove's media+20% FBS at a concentration of $5 \times 10^5$ cells/ml. Test compounds are then added with a final conc. of 0.4% DMSO. Cells are incubated at 37° C. with 5% $CO_2$ for up to 3 days. After 3 days cells are split 1:3 into fresh 96-well plates containing the test compound and allowed to grow up to an additional 3 days. After each 24h period, 50 ul of an XTT solution is added to one of the replicate 96-well plates and absorbance readings are taken at 2, 4 and 20 hours following manufacturer's directions. The reading taken with an OD for DMSO only treated cells within the linear range of the assay (0.5-1.5) is then taken and the percentage of viable cells in the compound treated wells are measured versus the DMSO only treated cells.

Example 907

CD69 Whole Blood Assay

Human blood is obtained from healthy volunteers, with the following restrictions: 1 week drug-free, non-smokers. Blood (approximately 20 mls to test 8 compounds) is collected by venipuncture into Vacutainer® (Becton, Dickinson and Co.) tubes with sodium heparin.

Solutions of Formula I compounds at 10 mM in DMSO are diluted 1:10 in 100% DMSO, then are diluted by three-fold serial dilutions in 100% DMSO for a ten point dose-response curve. The compounds are further diluted 1:10 in PBS and then an aliquot of 5.5 µl of each compound is added in duplicate to a 2 ml 96-well plate; 5.5 µl of 10% DMSO in PBS is added as control and no-stimulus wells. Human whole blood—HWB (100 µl) is added to each well. After mixing the plates are incubated at 37° C., 5% $CO_2$, 100% humidity for 30 minutes. Goat F(ab')2 anti-human IgM (10 µl of a 500 µg/ml solution, 50 µg/ml final) is added to each well (except the no-stimulus wells) with mixing and the plates are incubated for an additional 20 hours. At the end of the 20 hour incubation, samples are incubated with fluorescent labeled antibodies for 30 minutes, at 37° C., 5% $CO_2$, 100% humidity. Include induced control, unstained and single stains for compensation adjustments and initial voltage settings. Samples are then lysed with PharM Lyse™ (BD Biosciences Pharmingen) according to the manufacturer's instructions. Samples are then transferred to a 96 well plate suitable to be run on the BD Biosciences HTS 96 well system on the LSRII machine. Data acquired and Mean Fluorescence Intensity values were obtained using BD Biosciences DIVA Software. Results are initially analyzed by FACS analysis software (Flow Jo). The inhibitory concentrations (IC50, IC70, IC90, etc.) for test compounds is defined as the concentration which decreases by, for example 50%, the percent positive of CD69 cells that are also CD20 positive stimulated by anti-IgM (average of 8 control wells, after subtraction of the average of 8 wells for the no-stimulus background). The IC70 values are calculated by Prism version 5, using a nonlinear regression curve fit and are shown in Tables 1 and 2.

Example 908

In Vitro Cell Proliferation Assay

Efficacy of Formula I compounds are measured by a cell proliferation assay employing the following protocol (Mendoza et al (2002) Cancer Res. 62:5485-5488). The CellTiter-Glo® Luminescent Cell Viability Assay, including reagents and protocol are commercially available (Promega Corp., Madison, Wis., Technical Bulletin TB288). The assay assesses the ability of compounds to enter cells and inhibit cell proliferation. The assay principle is based on the determination of the number of viable cells present by quantitating the ATP present in a homogenous assay where addition of the Cell-Titer Glo reagent results in cell lysis and generation of a luminescent signal through the luciferase reaction. The luminescent signal is proportional to the amount of ATP present.

A panel of B-cell lymphoma cell lines (BJAB, SUDHL-4, TMD8, OCI-Ly10, OCI-Ly3, WSU-DLCL2) are plated into 384-well plate in normal growth medium, and serially diluted BTK inhibitors or DMSO alone were added to each well. Cell viability is assessed after 96 hour incubation by CellTiter-Glo® (Promega). Data may be presented as Relative cell viability in BTK inhibitor-treated cells relative to DMSO-treated control cells. Data points are the mean of 4 replicates at each dose level. Error bars represent SD from the mean.

Procedure: Day 1—Seed Cell Plates (384-well black, clear bottom, microclear, TC plates with lid from Falcon #353962), Harvest cells, Seed cells at 1000 cells per 54 µl per well into 384 well Cell Plates for 3 days assay. Cell Culture Medium: RPMI or DMEM high glucose, 10% Fetal Bovine Serum, 2 mM L-Glutamine, P/S. Incubate 0/N at 37° C., 5% CO2.

Day 2—Add Drug to Cells, Compound Dilution, DMSO Plates (serial 1:2 for 9 points), Add 20 µl compounds at 10 mM in the 2nd column of 96 well plate. Perform serial 1:2 across the plate (10 µl+20 µl 100% DMSO) for a total of 9 points using Precision. Media Plates 96-well conical bottom polypropylene plates from Nunc (cat. #249946) (1:50 dilution) Add 147 µl of Media into all wells. Transfer 3 µl of DMSO+compound from each well in the DMSO Plate to each corresponding well on Media Plate using Rapidplate.

Drug Addition to Cells, Cell Plate (1:10 dilution), Add 6 µl of media+compound directly to cells (54 µl of media on the cells already). Incubate 3 days at 37 C, 5% CO2 in an incubator that will not be opened often.

Day 5—Develop Plates, Thaw Cell Titer Glo Buffer at room temperature. Remove Cell Plates from 37° C. and equilibrate to room temperature. for about 30 minutes. Add Cell Titer Glo Buffer to Cell Titer Glo Substrate (bottle to bottle). Add 30 µl Cell Titer Glo Reagent (Promega cat. #G7572) to each well of cells. Place on plate shaker for about 30 minutes. Read luminescence on Analyst HT Plate Reader (half second per well).

Cell viability assays and combination assays: Cells were seeded at 1000-2000 cells/well in 384-well plates for 16 h. On day two, nine serial 1:2 compound dilutions are made in DMSO in a 96 well plate. The compounds are further diluted into growth media using a Rapidplate robot (Zymark Corp., Hopkinton, Mass.). The diluted compounds are then added to quadruplicate wells in 384-well cell plates and incubated at 37° C. and 5% CO2. After 4 days, relative numbers of viable cells are measured by luminescence using Cell-Titer Glo (Promega) according to the manufacturer's instructions and read on a Wallac Multilabel Reader (PerkinElmer, Foster City). EC50 values are calculated using Prism® 4.0 software (GraphPad, San Diego). Formula I compounds and chemotherapeutic agents are added simultaneously or separated by 4 hours (one before the other) in all assays.

An additional exemplary in vitro cell proliferation assay includes the following steps:

1. An aliquot of 100 µl of cell culture containing about $10^4$ cells in medium is deposited in each well of a 384-well, opaque-walled plate.
2. Control wells are prepared containing medium and without cells.
3. The compound is added to the experimental wells and incubated for 3-5 days.
4. The plates are equilibrated to room temperature for approximately 30 minutes.
5. A volume of CellTiter-Glo Reagent equal to the volume of cell culture medium present in each well is added.
6. The contents are mixed for 2 minutes on an orbital shaker to induce cell lysis.
7. The plate is incubated at room temperature for 10 minutes to stabilize the luminescence signal.
8. Luminescence is recorded and reported in graphs as RLU=relative luminescence units.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

We claim:
1. A compound selected from:
(S)-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrido[3,4-b]indolizin-1(2H)-one;
(S)-5-[5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl]-8-thia-4,5-diazatricyclo[7.4.0.02,7]trideca-1(9),2(7),3-trien-6-one;
(2S)-10-[5-fluoro-2-(hydroxymethyl)-3-[1-methyl-5-({5-[2-methyl-4-(oxetan-3-yl)piperazin-1-yl]pyridine-2-yl}amino)-6-oxo-1,6-dihydropyridin-3-yl]phenyl]-4,4-dimethyl-1,10-diazatricyclo[6.4.0.02,6]dodeca-2(6),7-dien-9-one;
2-(3-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one;
(S)-2-(3-(5-(5-(2-ethyl-4-(oxetan-3-yl)piperazin-1-yl)pyridin-2-ylamino)-1-methyl-6-oxo-1,6-dihydropyridin-3-yl-5-fluoro-2-(hydroxymethyl)phenyl)-3,4,6,7,8,9-hexahydropyrazino[1,2-a]indol-1(2H)-one;
(S)-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one;
(S)-2-(3-(5-(5-(3,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one;
(R)-2-(3-(5-(5-(3,4-dimethylpiperazin-1-yl)pyridin-2-ylamino)-1-methyl-6-oxo-1,6-dihydropyridin-3-yl)-5-fluoro-2-(hydroxymethyl) phenyl)-3,4,6,7,8,9-hexahydropyrazino[1,2-α]indol-1(2H)-one;
(R)-2-(3-(5-(5-(2,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one;
(S)-2-(3-(5-(5-(2,4-dimethylpiperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1 (2H)-one;
(S)-7,7-difluoro-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1(2H)-one;
2-(3-{5-[5-((S)-2-Ethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-7,7-dimethyl-3,4,7,8-tetrahydro-2H,6H-cyclopenta[4,5]pyrrolo[1,2-a]pyrazin-1-one;

(R)-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7,8,9-hexahydropyrazino[1,2-a]indol-1 (2H)-one;

2-(3-{5-[5-((2S,5R)-2,5-Dimethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-7,7-dimethyl-3,4,7,8-tetrahydro-2H,6H-cyclopenta[4,5]pyrrolo[1,2-a]pyrazin-1-one;

3-(5-Fluoro-2-hydroxymethyl-3-{1-methyl-5-[5-((R)-2-methyl-4-oxetan-3-yl-piperazin-1-yl)-pyridin-2-ylamino]-6-oxo-1,6-dihydro-pyridin-3-yl}-phenyl)-6,7,8,9-tetrahydro-3H-benzo[4,5]thieno[2,3-d]pyridazin-4-one;

3-(3-{5-[5-((2S,5R)-2,5-Dimethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-6,7,8,9-tetrahydro-3H-benzo[4,5]thieno[2,3-d]pyridazin-4-one;

(S)-10-fluoro-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)-3,4,6,7, 8,9-hexahydropyrazino[1,2-a]indol-1 (2H)-one;

3-(3-{5-[5-((S)-2-Ethyl-4-oxetan-3-yl-piperazin-1-yl)-pyridin-2-ylamino]-1-methyl-6-oxo-1,6-dihydro-pyridin-3-yl}-5-fluoro-2-hydroxymethyl-phenyl)-6,7,8,9-tetrahydro-3H-benzo[4,5]thieno[2,3-d]pyridazin-4-one;

2-(3-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-6,7,8,9-tetrahydropyrazino[1,2-a]indol-1 (2H)-one;

(S)-2-(3-(5-(5-(2-ethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-6,7,8,9-tetrahydropyrazino[1,2-a]indol-1(2H)-one;

(S)-2-(3-(5-(5-(2-ethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrido[3,4-b]indolizin-1(2H)-one;

2-(5-Fluoro-2-hydroxymethyl-3-{1-methyl-5-[5-((R)-2-methyl-4-oxetan-3-yl-piperazin-1-yl)-pyridin-2-ylamino]-6-oxo-1,6-dihydro-pyridin-3-yl}-phenyl)-7,7-dimethyl-3,4,7,8-tetrahydro-2H,6H-cyclopenta[4,5]pyrrolo[1,2-a]pyrazin-1-one;

2-(3-(5-(5-(2,2-dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-3,4,6,7,8,9-hexahydropyrazino[1,2-a]indol-1(2H)-one;

2-[3-[5-[[5-[(2S,5R)-2,5-dimethyl-4-(oxetan-3-yl)piperazin-1-yl]-2-pyridyl]amino]-1-methyl-6-oxo-3-pyridyl]-5-fluoro-2-(hydroxymethyl)phenyl]-3,4,6,7,8,9-hexahydropyrido[3,4-b]indolizin-1-one;

2-[5-fluoro-2-(hydroxymethyl)-3-[1-methyl-5-[[5-[(2S)-2-methyl-4-(oxetan-3-yl)piperazin-1-yl]-2-pyridyl]amino]-6-oxo-3-pyridyl]phenyl]-6,7,8,9-tetrahydropyridazino[4,5-b]indolizin-1-one;

2-(7,7-dimethyl-4-oxo-1,2,6,8-tetrahydrocyclopenta[3,4]pyrrolo[3,5-b]pyrazin-3-yl)-4-fluoro-6-[1-methyl-5-[[5-[(2S)-2-methyl-4-(oxetan-3-yl)piperazin-1-yl]-2-pyridyl]amino]-6-oxo-3-pyridyl]benzoic acid;

2-(7,7-dimethyl-4-oxo-1,2,6,8-tetrahydrocyclopenta[3,4]pyrrolo[3,5-b]pyrazin-3-yl)-4-fluoro-N-methyl-6-[1-methyl-5-[[5-[(2S)-2-methyl-4-(oxetan-3-yl)piperazin-1-yl]-2-pyridyl]amino]-6-oxo-3-pyridyl]benzamide;

3-[2-(hydroxymethyl)-3-[1-methyl-5-[[5-[2S)-2-methyl-4-(oxetan-3-yl)piperazin-1-yl]-2-pyridyl]amino]-6-oxo-3-pyridyl]phenyl]-6,7,8,9-tetrahydrobenzothiopheno[2,3-d]pyridazin-4-one; and 3-[5-fluoro-2-(hydroxymethyl)-3-[1-methyl-5-[[5-[(2S)-2-methyl-4-(oxetan-3-yl)piperazin-1-yl]-2-pyridyl]amino]-6-oxo-3-pyridyl]phenyl]-7,7-dimethyl-6,8-dihydrocyclopenta[3,4]thieno[1,3-d]pyridazin-4-one.

2. A pharmaceutical composition comprised of a compound of claim 1 and a pharmaceutically acceptable carrier, glidant, diluent, or excipient.

3. The pharmaceutical composition according to claim 2, further comprising a therapeutic agent.

4. A process for making a pharmaceutical composition which comprises combining a compound of claim 1 with a pharmaceutically acceptable carrier.

\* \* \* \* \*